(12) United States Patent
Lee et al.

(10) Patent No.: US 10,927,085 B2
(45) Date of Patent: Feb. 23, 2021

(54) 1,2-NAPHTHOQUINONE BASED DERIVATIVE AND METHOD OF PREPARING THE SAME

(71) Applicant: HUEN Co., Ltd., Cheonan-si (KR)

(72) Inventors: Whee Seong Lee, Suwon-si (KR); Mi Jung Lee, Yongin-si (KR); Bo Jung Kim, Yongin-si (KR); Tae Cheul Roh, Suwon-si (KR); Seung Hoon Lee, Suwon-si (KR); Kyu Dae Lee, Seoul (KR); You-Hui Lee, Seoul (KR); Tae Hwan Kwak, Yongin-si (KR)

(73) Assignee: HUEN Co., Ltd., Cheonan-si (KR)

( * ) Notice: Subject to any disclaimer, the term of this patent is extended or adjusted under 35 U.S.C. 154(b) by 0 days.

(21) Appl. No.: 15/102,974

(22) PCT Filed: Dec. 30, 2014

(86) PCT No.: PCT/KR2014/013038
§ 371 (c)(1),
(2) Date: Jun. 9, 2016

(87) PCT Pub. No.: WO2015/102369
PCT Pub. Date: Jul. 9, 2015

(65) Prior Publication Data
US 2016/0376243 A1 Dec. 29, 2016

(30) Foreign Application Priority Data
Dec. 30, 2013 (KR) .......................... 10-2013-0166912

(51) Int. Cl.
C07D 263/60 (2006.01)
C07D 498/04 (2006.01)
A61K 31/423 (2006.01)
C07C 221/00 (2006.01)

(52) U.S. Cl.
CPC .......... *C07D 263/60* (2013.01); *C07C 221/00* (2013.01); *C07D 498/04* (2013.01); *C07C 2602/10* (2017.05)

(58) Field of Classification Search
CPC .......................... C07D 263/60; C07D 498/04
See application file for complete search history.

(56) References Cited

FOREIGN PATENT DOCUMENTS

| JP | 2010-525053 | 7/2010 |
| KR | 10-2008-0096419 | 10/2008 |
| WO | 2008-066294 | 6/2008 |

OTHER PUBLICATIONS

Carroll et al., Chemical Communications, 1969, pp. 923-924.*
Carroll et al., Chemical Communications, 923-924, 1969.*
Mohinder S. Chauhan et al, "Some reactions of ethyl azidoformate with quinones" Canadian Journal of Chemistry, 1977, vol. 55, pp. 2363-2372.
Michael P. Bova et al, "The oxidative mechanism of action of ortho-quinone inhibitors of protein-tyrosine phosphatase α is mediated by hydrogen peroxide" Biochemistry and Biophysics, vol. 429, No. 1, Sep. 1, 2004, pp. 30-41.
European Patent Office, European Search Report of Application No. 14877254.4, dated Apr. 19, 2017.

* cited by examiner

*Primary Examiner* — Samantha L Shterengarts
(74) *Attorney, Agent, or Firm* — Lex IP Meister, PLLC

(57) ABSTRACT

Disclosed are a compound represented by Formula (1) below, or a pharmaceutically acceptable salt, hydrate, solvate, prodrug, tautomer, enantiomer, or pharmaceutically acceptable diastereomer thereof, a method of preparing the same, and a pharmaceutical composition, which have effects for treatment or prevention of metabolic syndromes, comprising the same:

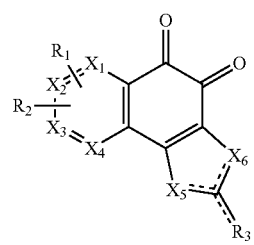

(1)

wherein $R_1$ to $R_3$, and $X_i$ to $X_6$ are the same as defined in claim 1.

24 Claims, 8 Drawing Sheets

1,2-NAPHTHOQUINONE BASED DERIVATIVE AND METHOD OF PREPARING THE SAME

TECHNICAL FIELD

The present invention relates to a 1,2-naphthoquinone based derivative, a method of preparing the same, and a composition, which has treatment and prevention effects for metabolic syndromes, including the same.

BACKGROUND ART

Metabolic syndromes represent risk factors such as hypertriglyceridemia, hypertension, abnormal glucose metabolism, abnormal blood coagulation, and obesity and may cause diseases such as heart attack, ischemic heart diseases, type 2 diabetes, hypercholesterolemia, cancers, gallstones, arthritis, arthralgia, respiratory diseases, sleep apnea, benign prostatic hyperplasia, menstrual irregularity, and the like. Therefore, metabolic syndromes pose a great threat to modern people. According to a National Cholesterol Education Program (NCEP) standard published in America, 2001, a patient is judged to have a metabolic syndrome when the patient presents with at least one of ① a waist size of 40 inches (102 cm) or more in men, a waist size of 35 inches (88 cm) or more in women, ② triglycerides of 150 mg/dL or more, ③ HDL cholesterol of 40 mg/dL or less in men and 50 mg/dL or less in women, ④ a blood pressure of 130/85 mmHg or more, ⑤ fasting glucose of 110 mg/dL. In Asians, when men have a waist size of 90 cm or more and women have a waist size of 80 cm or more, they are judged to have abdominal obesity. When such standards were applied to Koreans, it was recently reported that approximately 25% Koreans have metabolic syndromes.

Chronic and long-term high-calorie intake is considered as a major risk factor of such metabolic syndromes. Metabolic efficiency is reduced due to excessive energy intake, lack of exercise, life extension, aging, and the like, thereby causing obesity, diabetes, and metabolic syndromes due to excessive caloric intake.

As treatment methods, diet therapies, exercise therapies, behavioral control therapies, drug treatments, and the like are carried out. However, since exact causes of metabolic syndromes are not known, treatment effects are presently insignificant and symptoms are merely alleviated or progression of diseases is delayed. A variety of therapeutic targets have been identified but an excellent treatment target has yet to be reported.

Meanwhile, since NADH and NADPH are used in a fat biosynthesis process when ratios of $NAD^+/NADH$ and $NADP^+/NADPH$ are reduced and, thus, NADH and NADPH remain in vivo or in vitro, and NADH and NADPH are used as major substrates causing reactive oxygen species (ROS) when present in excess, ROS causes diseases such as inflammatory diseases. For these reasons, if in vivo or in vitro environment may be changed such that a state, in which ratios of $NAD^+/NADH$ and $NADP^+/NADPH$ are increased, is stably maintained, fat oxidation due to $NAD^+$ and $NADP^+$ and a variety of energy consumption metabolism may be activated. As a result, if an action mechanism to continuously keep the low concentration of NAD(P)H can be activated, a variety of diseases including obesity may be treated by inducing consumption of excessive calories.

To increase the concentration and a ratio of $NAD(P)^+$ which is a signal messenger known as performing a variety of functions as described above, methods below are considered: first, a method of controlling a salvage synthesis process as an $NAD(P)^+$ biosynthesis process; second, a method of increasing the concentration of $NAD(P)^+$ in vivo by activating genes or proteins of enzymes using NAD(P)H as a substrate or a coenzyme; third, a method of increasing the concentration of $NAD(P)^+$ by supplying $NAD(P)^+$ or an analogue, derivative, precursor, or prodrug thereof from the outside; and the like.

NAD(P)H:quinone oxidoreductase (EC1.6.99.2) is called DT-diaphorase, quinone reductase, menadione reductase, vitamin K reductase, azo-dye reductase, or the like. Such NQO exists in two isoforms, namely, NQO1 and NQO2 (ROM. J. INTERN. MED. 2000-2001, vol. 38-39, 33-50). NQO is a flavoprotein and facilitates removal of quinone or quinone derivatives through detoxification reaction. NQO uses NADH and NADPH as electron donors. Activation of NQO prevents formation of highly reactive quinone metabolites removes benzo (d)pyrene or quinone, and lowers toxicity of chrome. Although activation of NQO occurs in all tissues, activation thereof depends on tissue types. Generally, it was confirmed that expression of NQO was increased in cancer cells and tissues such as the liver, stomach, kidney, and the like. Expression of the NQO gene is induced by xenobiotics, antioxidants, oxidants, heavy metals, ultraviolet light, radiation, and the like. NQO is a part of lots of cellular defense mechanisms induced by oxidative stress. Combined expression of genes related to defense mechanisms including NQO protects cells against oxidative stress, free radicals, and neoplasia. NQO has very broad substrate specificity and, as substrates thereof, quinone, quinone-imines, and nitro and azo compounds may be used.

Thereamong, NQO1 is mainly expressed in epithelial cells and endothelial cells. This means that NQO1 may function as a defense mechanism against compounds absorbed through air, the throat, or blood vessels. Recently, it was reported that expression of an NQO1 gene greatly increased in adipose tissues of humans having metabolic syndrome and expression of NQO1 in larger adipose cells was statistically significantly high. When weight loss was induced through diet treatments, expression of NQO1 proportionally decreased with weight loss. It was confirmed that the amount of NQO1 mRNA is proportional to GOT and GPT known as indicators of fatty liver syndrome. Therefore, it is judged that NQO1 may play a role in metabolic syndromes related to obesity, when it is considered that expression of NQO1 in adipose tissues relates to adiposity, glucose tolerance, and liver function index (Journal of Clinical Endocrinology & Metabolism 92 (6):2346. 2352).

DISCLOSURE

Technical Problem

Therefore, the present invention has been made to solve the above and other technical problems that have yet to be resolved.

In particular, the present invention aims to provide a 1,2-naphthoquinone based derivative having a novel structure.

In accordance with another aspect of the present invention, there is provided such a novel compound.

In accordance with another aspect of the present invention, there is provided a composition for treatment and prevention of metabolic syndromes, the composition including such a novel compound in a therapeutically effective amount, as an active ingredient.

In accordance with yet another aspect of the present invention, there is provided a method for treatment and prevention of metabolic syndromes using such a novel compound as an active ingredient.

Technical Solution

In accordance with an aspect of the present invention, the above and other objects can be accomplished by the provision of a compound represented by Formula (1) below, or a pharmaceutically acceptable salt, hydrate, solvate, prodrug, tautomer, enantiomer, or pharmaceutically acceptable diastereomer thereof:

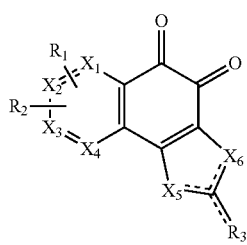

(1)

wherein $R_1$ and $R_2$ are each independently hydrogen, hydroxyl, a halogen, substituted or unsubstituted C1-C20 alkoxy, substituted or unsubstituted C1-C10 alkyl, substituted or unsubstituted C4-C10 aryl, substituted or unsubstituted C4-C10 aryloxy, substituted or unsubstituted C2-C10 heteroaryl, —$NO_2$, —$NR'_1R'_2$, —$NR'_1(CO(O)R'_2)$, —$NR'_1(C(O)NR'_1R'_2)$, —$CO(O)R'_1$, —$C(O)NR'_1R'_2$, —CN, —$SO(O)R'_1$, —$SO(O)NR'_1R'_2$, —$NR'_1(SO(O)R'_2)$, —$CSNR'_1R'_2$, or $R_1$ and $R_2$ may form a ring structure of substituted or unsubstituted C4-C10 aryl through coupling or a ring structure of substituted or unsubstituted C2-C10 heteroaryl, where $R'_1$ and $R'_2$ are each independently hydrogen, substituted or unsubstituted C1-C6 alkyl, substituted or unsubstituted C3-C8 cycloalkyl, substituted or unsubstituted C4-C10 aryl, substituted or unsubstituted C4-C10 aryloxy, substituted or unsubstituted C1-C8 heteroaryl, substituted or unsubstituted —$(CR''_1R''_2)m'$-C4-C10 aryl, substituted or unsubstituted —$(CR''_1R''_2)m'$-C4-C10 heteroaryl, or substituted or unsubstituted $NR''_1R''_2$; where $R''_1$ and $R''_2$ are each independently hydrogen or C1-C3 alkyl, or $R''_1$ and $R''_2$ may form a ring structure of substituted or unsubstituted C4-C10 aryl through coupling;

$R_3$ is hydrogen, oxygen, a halogen, substituted or unsubstituted C1-C10 alkyl, substituted or unsubstituted C2-C20 alkene, substituted or unsubstituted C1-C20 alkoxy, substituted or unsubstituted C3-C8 cycloalkyl, substituted or unsubstituted C2-C8 heterocycloalkyl, substituted or unsubstituted C4-C10 aryl, substituted or unsubstituted C4-C10 aryloxy, substituted or unsubstituted C1-C10 heteroaryl, substituted or unsubstituted —$(CR'_5R'_6)_m$-C4-C10 aryl, substituted or unsubstituted —$(CR'_5R'_6)_m$—C4-C10 aryloxy, substituted or unsubstituted —$(CR'_5R'_6)_m$—C1-C10 heteroaryl, substituted or unsubstituted —$(CR'_5R'_6)_m$—$NR'_3R'_4$, substituted or unsubstituted —$(CR'_5R'_6)_m$—C2-C10 heterocycloalkyl, substituted or unsubstituted —$(CR'_5R'_6)_m$—$OR'_3$, substituted or unsubstituted —$(CR'_5R'_6)_m$ $(O)COR'_3$, —$CO(O)R'_3$, —$CONR'_3R'_4$, —$NR'_3R'_4$, —$NR'_3(C(O)R'_4)$, —$CH_2A$ when the compound of Formula (1) is "A", or -A when the compound of Formula (1) is "A";

where $R'_3$ and $R'_4$ are each independently hydrogen, substituted or unsubstituted C1-C6 alkyl, substituted or unsubstituted C3-C8 cycloalkyl, substituted or unsubstituted C4-C10 aryl, substituted or unsubstituted —$(CR'_5R'_6)_m$—C4-C10 aryl, substituted or unsubstituted —$(CR'_5R'_6)_m$—C4-C10 aryloxy, substituted or unsubstituted —$(CR'_5R'_6)_m$—C1-C10 heteroaryl, —$CO(O)R'''_3$, or $R'_3$ and $R'_4$ may form a ring structure of substituted or unsubstituted C2-C10 heterocycloalkyl or a ring structure of substituted or unsubstituted C1-C10 heteroaryl through coupling;

$R'_5$, and $R'_6$ are each independently hydrogen or C1-C3 alkyl; and $R'''_3$ is C1-C6 alkyl;

wherein the substituted group is at least one selected from the group consisting of hydroxy, a nitro group, a halogen, C1-C10 alkyl, C2-C10 alkenyl, C2-C10 alkynyl, C1-C10 alkoxy, C1-C10 alkoxycarbonyl, C3-C8 cycloalkyl, C2-C8 heterocycloalkyl, C4-C10 aryl, and C2-C10 heteroaryl;

$X_1$, $X_2$, $X_3$ and $X_4$ are each independently C(H), CO, or $N(R''_3)$;

$X_6$ is O when $X_5$ is $N(R''_4)$ and $X_6$ is $N(R''_4)$ when $X_5$ is O;

where $R''_3$ and $R''_4$ are each independently hydrogen, substituted or unsubstituted C1-C6 alkyl, C1-C6 alkoxy, or substituted or unsubstituted —$(CH_2)_n$—C4-C6 aryl and a substituted group is at least one selected from the group consisting of hydroxy, a halogen, and C1-C5 alkyl;

m, m', and n are each independently a natural number of 1 to 4;

the heteroatom is at least one selected from N, O, and S;

" " means a single bond or a double bond; and $R_3$ is not a $CH_3$ or n-propyl structure when $X_1$, $X_2$, $X_3$ and $X_4$ are CH, $X_5$ is O, and $X_6$ is N.

Hereinafter, so long as not specified otherwise, the compound of Formula (1) as an active ingredient of a therapeutic agent includes any of a pharmaceutically acceptable salt, hydrate, solvate, prodrug, tautomer, enantiomer, or pharmaceutically acceptable diastereomer thereof and all thereof must be understood as being within the scope of the present invention. For convenience of description, they are simply called a compound of Formula (1).

The compound of Formula (1) according to the present invention has a novel structure which exhibits superior effects for treatment and prevention of metabolic diseases in vivo through exercise imitation effects as described in experimental examples below.

In particular, the compound of Formula (1) according to the present invention may increase a ratio of AMP/ATP by inducing that NAD(P)H:quinone oxidoreductase (NQO1) as an oxidation-reduction enzyme increases a ratio of NAD+/NADH in vivo. Increase of AMP in cells activates AMPK functioning as an energy gauge and, thus, lipometabolism is facilitated due to expression of PGC1a activating energy metabolism in mitochondria, thereby supplementing insufficient ATP energy. In addition, increased $NAD^+$ is used as a cofactor of glucose metabolism- and lipometabolism-related enzymes in vivo and, thus, facilitates metabolism. In addition, cADPR generated through decomposition of $NAD^+$ discharges $Ca^{2+}$ in the endoplasmic reticulum (ER) and, thus, synergistically activates mitochondria metabolism. Accordingly, exercise imitation effects may be induced in vivo.

Expressions used in the present invention will be simply described.

The expression "pharmaceutically acceptable salt" means a formulation of a compound that does not cause strong stimuli in an organism to which the compound is administered and does not destroy biological activity and properties thereof.

The expression "hydrate", "solvate", "prodrug", "tautomer", and "enantiomer or pharmaceutically acceptable diastereomer" has the same meaning as the above.

The pharmaceutical salt includes acids forming a nontoxic acid addition salt containing pharmaceutically acceptable anions, inorganic acids such as hydrochloric acid, sulfuric acid, nitric acid, phosphoric acid, hydrobromic acid, hydriodic acid, and the like, organic carboxylic acids such as tartaric acid, formic acid, citric acid, acetic acid, trichloroacetic acid, trifluoroacetic acid, gluconic acid, benzoic acid, lactic acid, fumaric acid, maleic acid, salicylic acid, and acid addition salts formed from sulfonic acids such as methanesulfonic acid, ethanesulfonic acid, benzenesulfonic acid, and p-toluenesulfonic acid, and the like. Examples of the pharmaceutically acceptable carboxylic acid salts include metal salts or alkaline earth metal salts formed from lithium, sodium, potassium, calcium, magnesium, and the like, amino acid salts such as lysine, arginine, guanidine, and the like, and organic salts such as dicyclohexylamine, N-methyl-D-glucamine, tris(hydroxymethyl)methylamine, diethanolamine, choline, triethylamine, and the like. The compound of Formula (1) according to the present invention may be transformed into salts thereof through a conventional method.

The expression "hydrate" means the compound according to the present invention including a stoichiometric or non-stoichiometric amount of water bound through non-covalent intermolecular forces or salts thereof.

The expression "solvate" means the compound according to the present invention including a stoichiometric or non-stoichiometric amount of solvent bound through non-covalent intermolecular forces or salts thereof. As preferable solvents therefor, there are volatile and/or non-toxic solvents which are suitable for administration to humans.

The expression "prodrug" means a drug modified into a parent drug in vivo. Since prodrugs may be more easily administered than parent drugs in some cases, they are often used. For example, a prodrug may be active upon oral administration while the corresponding parent drug is not. In addition, prodrugs may have better solubility than a parent drug in pharmaceutical compositions. For example, Although water solubility of a prodrug negatively affects mobility thereof, the prodrug may be a compound, which is hydrolyzed into carboxylic acid as an activator, administered as an ester ("prodrug") which facilitates membrane transport. As another example of the prodrug, there is a short peptide (polyamino acid), which is bound to an acid radical, converted into an active form through metabolism.

The expression "tautomer" means a structural isomer type having an identical chemical or molecular formula but different coupling between constituent atoms. For example, a keto-eno structure is changed due to continuous movement between isomers.

The expression "enantiomer or pharmaceutically acceptable diastereomer" means each of two or more compounds with the same formula but a different arrangement of atoms in the molecule and different properties. The expression "enantiomer" means each of a pair of molecules that are mirror images of each other, like a right hand and a left hand. In addition, the expression "diastereomer" means a stereoisomer, which is not a mirror image, like a trans form or a cis form and is limited to a pharmaceutically acceptable diastereomer in the present invention. All isomers thereof and mixtures thereof are also within the scope of the present invention.

The expression "alkyl" means aliphatic hydrocarbon groups. In the present invention, "alkyl" includes "saturated alkyl", which does not include alkene or alkyne portions, and "unsaturated alkyl", which includes at least one alkene or alkyne portion. In particular, "alkyl" according to the present invention may be "saturated alkyl" which does not include alkene or alkyne portions. The alkyl may include branched, linear, and circular types. In addition, since "alkyl" includes structural isomers, for example, C3 alkyl may mean propyl and isopropyl.

The expression "alkene" means hydrocarbons including at least one carbon-carbon double bond and the expression "alkyne" means hydrocarbons including at least two carbon atoms are combined at least one carbon-carbon triple bond.

The expression "heterocycloalkyl" means a substituent in which cyclic carbon is substituted with oxygen, nitrogen, sulfur, or the like.

The expression "aryl" means an aromatic substituent including at least one ring having a covalent it electron system. "Aryl" includes monocyclic or fused-ring polycyclic (that is, rings sharing neighboring pairs of carbon atoms) groups. When substituted, a substituted group may be properly bound to ortho (o), meta (m), or para (p) positions.

The expression "heteroaryl" means an aromatic group including at least one heterocyclic ring.

Examples of "aryl" or "heteroaryl" include phenyl, furan, pyran, pyridyl, pyrimidyl, triazyl, and the like, but the present invention is not limited thereto.

The expression "halogen" means elements belonging to Group 17 of the periodic table and may be particularly fluorine, chlorine, bromine, or iodine.

The expression "aryloxy" means a group in which an oxygen atom is bound to one carbon of an aromatic ring. For example, when oxygen binds to a phenyl group, —O—$C_6H_5$ and —$C_6H_4$—O— are possible.

Other expressions may be interpreted as meanings generally understood in the art.

In one embodiment according to the present invention, $X_1$ and $X_2$ may each independently be C(H), CO, or N($R_3$"), where $R_3$" may be hydrogen or C1-C3 alkyl, and $X_3$ and $X_4$ may each independently be C(H) or N.

In a more detailed embodiment, $X_1$ may be C(H), N, NH, or NCH$_3$; $X_2$ may be C(H) or CO; and $X_3$ and $X_4$ may each independently be C(H) or N.

In another embodiment of the present invention, $R_1$ and $R_2$ may each independently be hydrogen, a halogen, hydroxy, substituted or unsubstituted C1-C20 alkoxy, substituted or unsubstituted C1-C10 alkyl, substituted or unsubstituted C4-C10 aryl, substituted or unsubstituted C2-C10 heteroaryl, —NO$_2$, —NR'$_1$R'$_2$, —NR'$_1$ (C(O)R'$_2$), —NR'$_1$ (SO(O)R'$_2$), —NR'$_1$ (C(O)NR'$_1$R'$_2$), —CO(O)R'$_1$, —C(O)NR'$_1$R'$_2$, or —CN, or $R_1$ and $R_2$ may form a ring structure of substituted or unsubstituted C4-C10 aryl through coupling or a ring structure of substituted or unsubstituted C2-C10 heteroaryl, where R'$_1$ and R'$_2$ may each independently be hydrogen, substituted or unsubstituted C1-C6 alkyl, substituted or unsubstituted C3-C8 cycloalkyl, substituted or unsubstituted C4-C10 aryl, substituted or unsubstituted C1-C8 heteroaryl, or substituted or unsubstituted —(CH$_2$)$_m$—C4-C10 aryl.

In a more detailed embodiment, $R_1$ and $R_2$ may each independently be hydrogen, F, Cl, —OCH$_3$, —OCH$_2$CH$_3$, —O(CH$_2$)$_2$CH$_3$, —CH$_3$, —NO$_2$, —NH$_2$—, —N(CH$_3$)$_2$, —NHCOCH$_3$, —NHCOC$_3$H$_5$, —NHCOC$_3$H$_7$, or —CN or —OH.

In another embodiment of the present invention,

R$_3$ may be hydrogen, substituted or unsubstituted methyl, ethyl, n-propyl, isopropyl, butyl, isobutyl, t-butyl, pentyl, neopentyl, substituted or unsubstituted C4-C8 aryl, substituted or unsubstituted C4-C8 aryloxy, substituted or unsubstituted C1-C8 heteroaryl, substituted or unsubstituted —(CR'$_5$R'$_6$)$_m$—OR'$_3$, substituted or unsubstituted —(CR'$_5$R'$_6$)$_m$—OCOR'$_3$, or substituted or unsubstituted —(CR'$_5$R'$_6$)$_m$—NR'$_3$R'$_4$; where R'$_3$ and R'$_4$ may each independently be hydrogen, substituted or unsubstituted C1-C5 alkyl, or substituted or unsubstituted C4-C10 aryl, or R'$_3$ and R'$_4$ may form a ring structure of substituted or unsubstituted C4-C10 heterocycloalkyl through coupling or a ring structure of substituted or unsubstituted C1-C6 heteroaryl;

R'$_5$, and R'$_6$ may each independently be hydrogen or C1-C3 alkyl;

wherein the substituted group may be at least one selected from the group consisting of hydroxy, a halogen, C1-C10 alkyl, C2-C10 alkenyl, C2-C10 alkynyl, C1-C10 alkoxy, C1-C10 alkoxycarbonyl, C3-C8 cycloalkyl, C2-C8 heterocycloalkyl, C4-C10 aryl, and C5-C10 heteroaryl;

the heteroatom may be at least one selected from N, O, and S; and m may be a natural number of 1 to 4.

In a more detailed embodiment, R'$_6$ may be hydrogen.

In a more detailed embodiment,

R$_3$ may be methyl, ethyl, n-propyl, isopropyl, butyl, isobutyl, t-butyl, pentyl, neopentyl, substituted or unsubstituted phenyl, substituted or unsubstituted —(CR'$_5$R'$_6$)$_m$—OR'$_3$, or substituted or unsubstituted —(CHR'$_5$)$_m$—NR'$_3$R'$_4$, where R'$_3$ and R'$_4$ may be each independently hydrogen, methyl, ethyl, propyl, or substituted or unsubstituted C4-C10 aryl or R'$_3$ and R'$_4$ may form a ring structure of substituted or unsubstituted C4-C6 heterocycloalkyl through coupling;

R'$_5$ may be hydrogen or methyl;

a substituted group may be at least one selected from the group consisting of a halogen, C1-C3 alkyl, and C1-C3 alkoxy;

the heteroatom may be at least one selected from N, O, and S; and m may be a natural number of 1 to 2.

In a more detailed embodiment,

R$_3$ may be methyl, ethyl, isopropyl, t-butyl, phenyl, phenyl substituted with fluoro, —CH$_2$OCOCH$_3$—CH$_2$N(CH$_3$)$_2$, substituted or unsubstituted —CH$_2$NCH$_3$C$_6$H$_5$, substituted or unsubstituted —CH$_2$NHC$_6$H$_5$

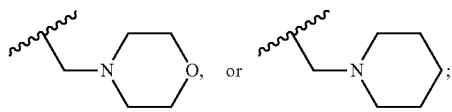 [SMILES: *CN1CCOCC1 ; *CN1CCCCC1]

and the substituted group may be at least one selected from the group consisting of a halogen, methyl, and methoxy.

In another embodiment of the present invention,

R''$_4$ may be hydrogen, C1-C3 alkyl, or substituted or unsubstituted —CH$_2$—C4-C6 aryl, wherein a substituted group may be a halogen.

The compound of Formula (1) may be exemplified by one of compounds below, but the present invention is not limited to compounds below.

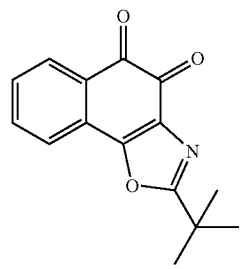

2

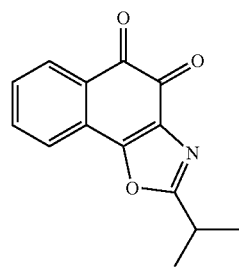

1

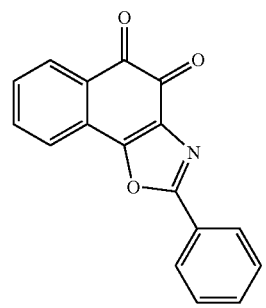

3

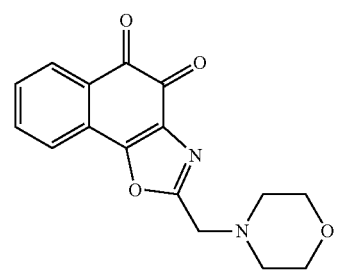

4

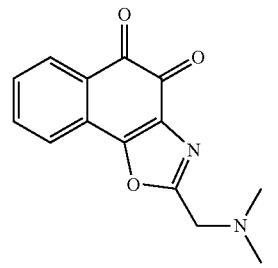

5

-continued

-continued
18
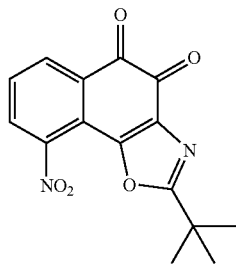
19
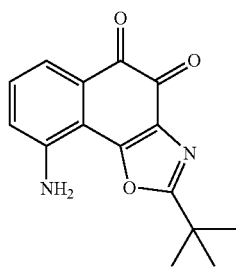
20
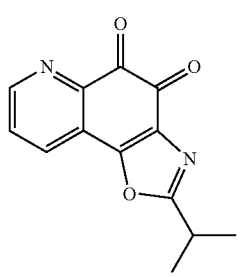
21
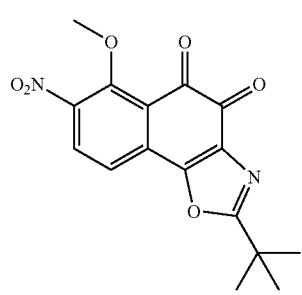
22
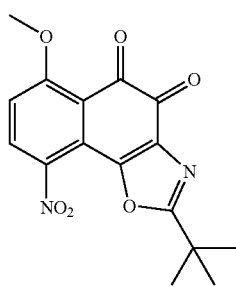
-continued
23
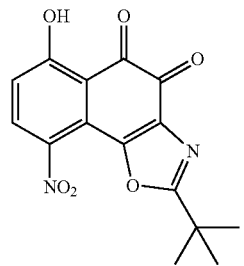
24
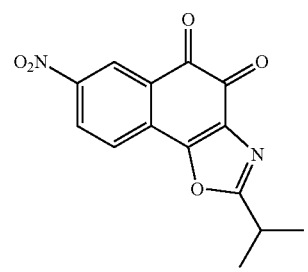
24
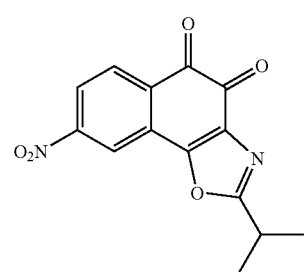
25
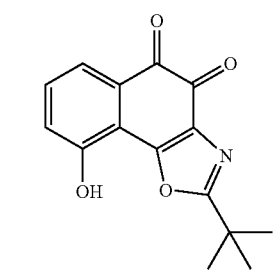
26
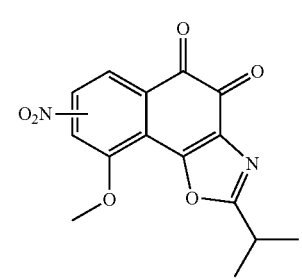

27
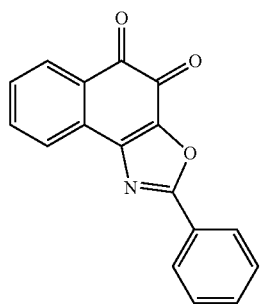
28
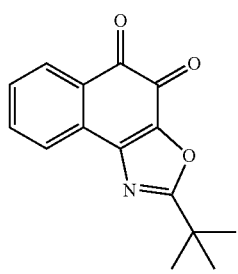
29
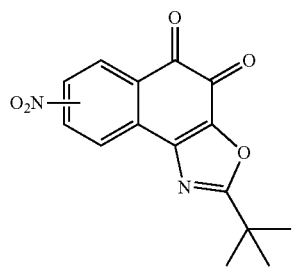
30
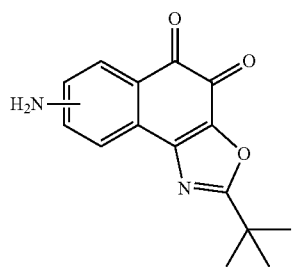
31
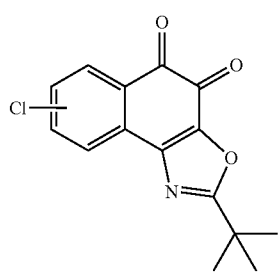
32
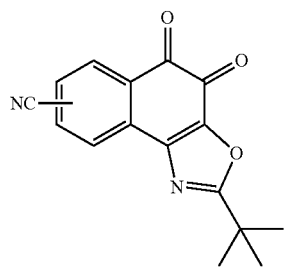
33
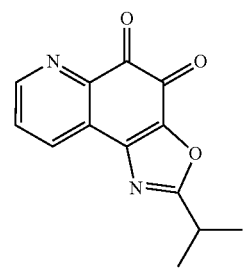
34
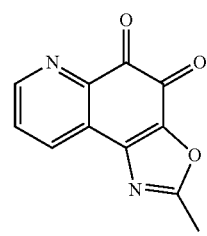
35
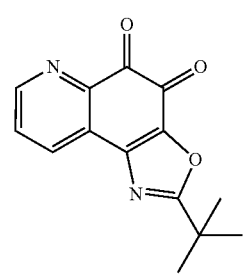
36
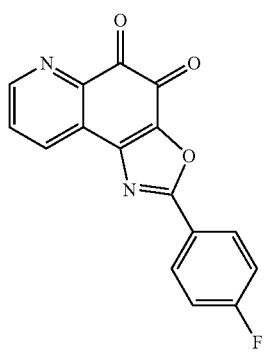

-continued
38
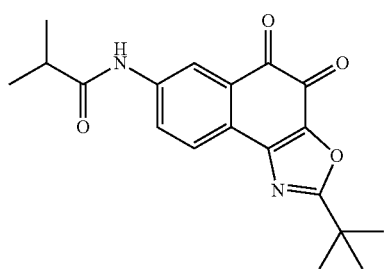
37
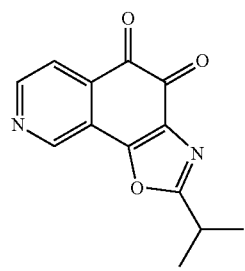
39
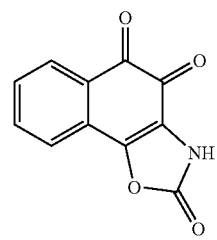
40
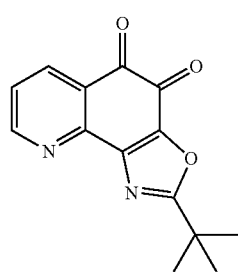
41
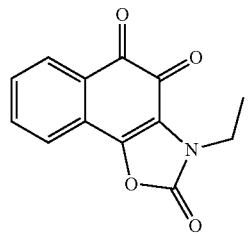
42
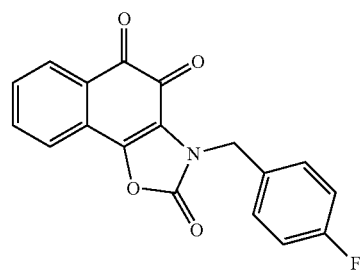
-continued
43
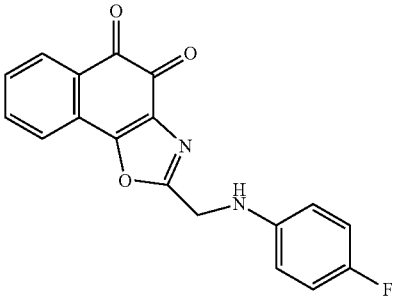
44
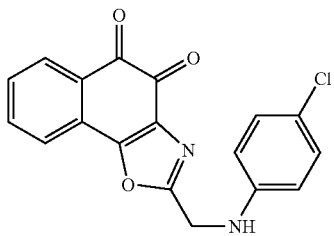
45
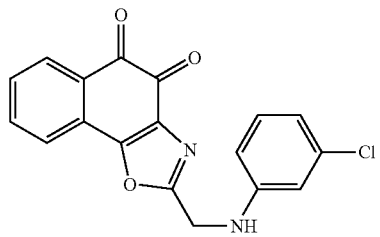
46
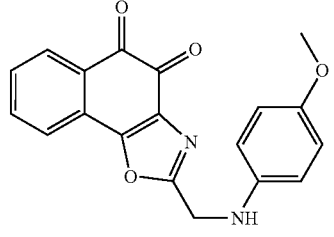
47
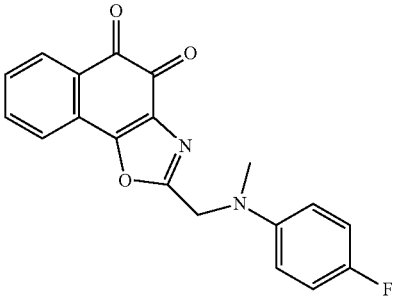
48
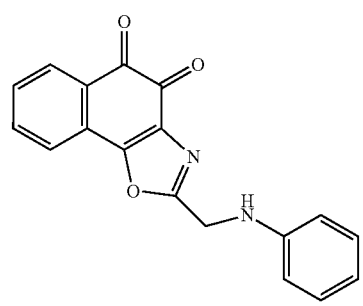

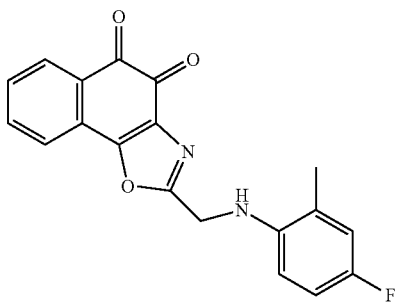
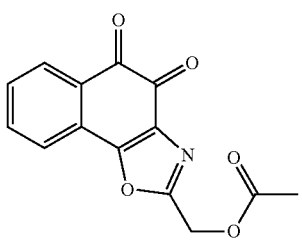
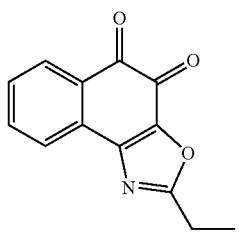
More preferably, the compound of Formula (1) may be one of compounds below:
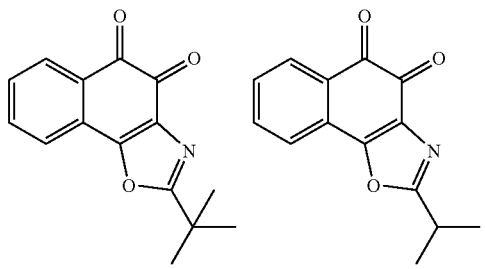
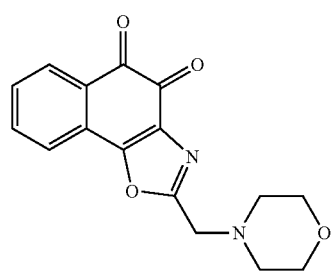
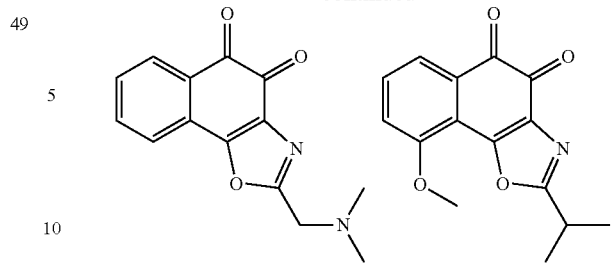
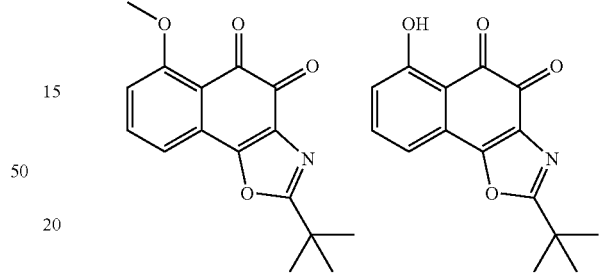
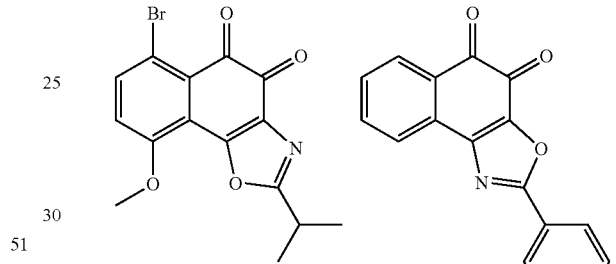
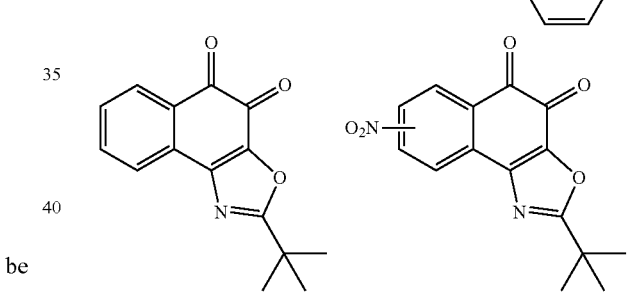
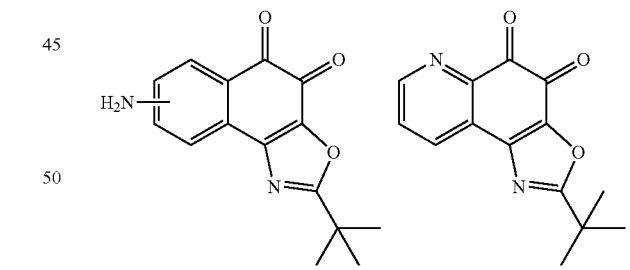
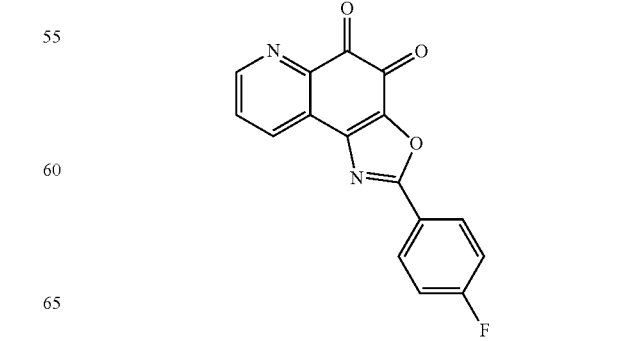

-continued

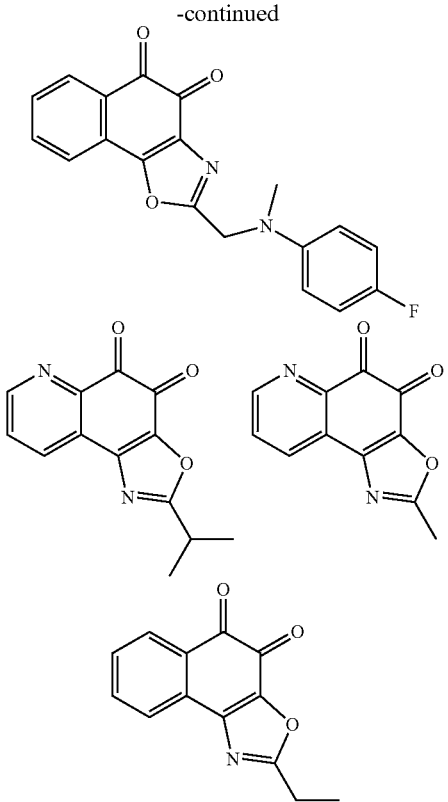

In addition, the present invention provides a method of preparing the compound of Formula (1).

Those skilled in the art ("a person skilled in the art") can prepare compounds based on the structure of Formula (1) according to a variety of methods. Thus, the present invention is intended to cover such methods. That is, the compound of Formula (1) may be prepared by randomly combining a variety of synthesis methods used in the prior art of the present invention. Therefore, the scope of the present invention is not limited thereto.

In one embodiment, a method of preparing the compound of Formula (1) may include, depending on a structure thereof:

A) introducing —NH$_2$ into a compound of Formula (2) below;

B) reacting the compound generated in the synthesizing (A) with R$_3$COH, R$_3$X or 4-nitrophenyl chloroformate under acidic conditions or with R$_3$COH or R$_3$X under acidic conditions after reacting MX; and C) oxidizing the compound generated in the introducing (B) or oxidizing after reacting under acidic conditions.

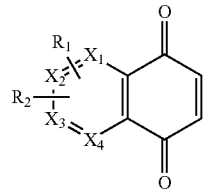

wherein X$_1$ to X$_4$ and R$_1$ to R$_3$ are the same as defined in Formula (1), M is Cu, Al, or B, and X is a halogen.

The acidic conditions of the present invention may be formed using nitric acid, sulfuric acid, acetic acid, or acetic acid anhydride, but the present invention is not limited thereto.

The 4-nitrophenyl chloroformate may be represented by Formula (3) below:

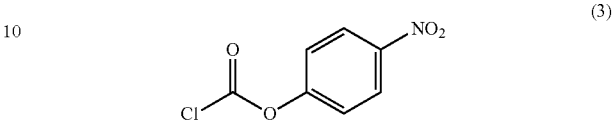

In particular, in the introducing (A), —NH$_2$ may be introduced by reacting the compound of Formula (2) and O-benzylhydroxylamine hydrochloride or NaN$_3$.

In addition, reacting the compound generated in the oxidizing (C) and MX' or R"$_4$X' may be additionally included. In the above formula, M is Cu, Al, or B; X' is a halogen; and R"$_4$ is the same as defined in Formula (1).

In addition, reacting the compound generated in the oxidizing (C) with HNO$_3$ to introduce —NO$_2$ (D) may be additionally included.

In another embodiment,
the present invention provides a method of preparing the compound of Formula (1), the method including:

a) introducing —NH$_2$ to the compound of Formula (2);

b) reacting the compound generated in the introducing (A) with (R$_8$O)$_2$CH(CH$_2$)$_n$X under acidic conditions; and c) oxidizing the compound generated in the reacting (B) and then reacting with R$_9$R$_{10}$NH, or reacting the compound generated in the reacting (B) with R$_9$R$_{10}$NH and then oxidizing, wherein R$_8$ is C1-C3 alkyl;

R$_9$ and R$_{10}$ may each independently be hydrogen, C1-C3 alkyl, or substituted or unsubstituted phenyl, or R$_9$ and R$_{10}$ may form a ring structure of C4-C6 heterocycloalkyl through coupling, wherein a heteroatom may be at least one selected from the group consisting of N, O, and S and a substituted group is at least one selected from a halogen, C1-C3 alkyl and C1-C3 alkoxy;

X is a halogen; and.

n' is an integer of 0 to 4.

In another embodiment of the present invention,
the method of preparing the compound of Formula (1) may further include:

A') introducing NO$_2$ to the compound of Formula (4) below through reaction with HNO$_3$;

B') reducing the compound generated in the introducing (A') or reducing after reacting with R$_6$X"; and C') reacting the compound generated in the reducing (B') and the compound generated in the introducing (A) with R$_3$COH under acidic conditions and oxidizing:

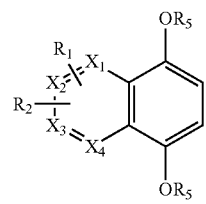

wherein $X_1$ to $X_4$ and $R_1$ to $R_3$ are the same as defined in Formula (1); $R_5$ and $R_6$ each are C1-C5 alkyl; and X" is a halogen.

The reduction in the present invention may be, for example, hydrogenation. Hydrogenation is a process in which hydrogen is reacted with a metal catalyst such as Pd/C or the like, which is widely known in the art. Therefore, detailed description thereof will be omitted.

In another embodiment, the method of preparing the compound of Formula (1) according to the present invention may include:

1) reacting a compound of Formula (5) below and $R_7NH_2$; and 2) oxidizing the compound generated in the reacting (1),

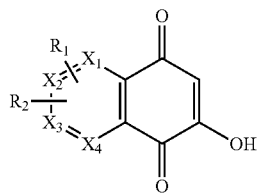

(5)

wherein $X_1$ to $X_4$ and $R_1$ to $R_3$ are the same as defined in Formula (1); and $R_7$ is C1-C5 alkyl or benzyl.

In addition, (3) introducing $NO_2$ to the compound generated in the oxidizing (2) may be additionally included.

In addition, (4) hydrogenating the compound generated in the introducing (3) may be additionally included.

In addition, (5) reacting the compound generated in the hydrogenating (4) with CuX''', where X''' is a halogen or CN, may be additionally included.

In addition, (4-1) reacting the compound generated in the hydrogenating (4) with $R_3COCl$, where $R_3$ is the same as defined in Formula (1), may be additionally included.

In another embodiment,
the method of preparing the compound of Formula (1) according to the present invention may include:

(1') reducing $NO_2$ to $NH_2$ through reduction after alkylating a compound of Formula (6) below, and introducing a halogenation group thereto; and (2') reacting the compound generated in the reducing (1') and $R_3COCl$;

(3') cyclizing the compound generated in the reacting (2') and then hydrogenating; and (4') oxidizing the compound generated in the cyclizing (3').

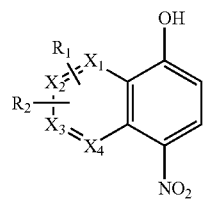

(6)

wherein $X_1$ to $X_4$ and $R_1$ to $R_3$ are the same as defined in Formula (1).

In the present invention, the expression "cyclizing" means that a ring is formed in the reaction product.

In addition, (2'-1) reacting the compound generated in the reacting (2') with a metal halide and alkylating may be additionally included between the reacting (2') and the cyclizing (3').

The present invention will be described in more detail through examples and experimental examples below.

In addition, the present invention provides a pharmaceutical composition for treatment and prevention of metabolic syndromes including (a) a therapeutically effective amount of the compound of Formula (1) according to claim 1 and/or a pharmaceutically acceptable salt, hydrate, solvate, tautomer, enantiomer, and/or pharmaceutically acceptable diastereomer thereof; and (b) a pharmaceutically acceptable carrier, diluent, or vehicle, or a combination thereof.

The expression "pharmaceutical composition" means a mixture of the compound according to the present invention and chemical ingredients such as a diluent, a carrier, and the like. A pharmaceutical composition aids in administration of a compound to organisms. As methods to administer a compound, there are oral, injection, aerosol, parenteral, and local administration, but the present invention is not limited thereto. A pharmaceutical composition may be obtained by reacting with acidic compounds such as hydrochloric acid, bromic acid, sulfuric acid, nitric acid, phosphoric acid, methanesulfonic acid, p-toluenesulfonic acid, salicylic acid, or the like.

The expression "therapeutically effective amount" means a therapeutically effective amount of active ingredient in a compound administered to alleviate or reduce one symptom or more of a target disorder or to delay initiation of clinical markers or symptoms of diseases requiring prevention. Therefore, "therapeutically effective amount" means an amount having (1) effects of slowing progression of a disease, (2) effects of partly stopping progression of a disease, and/or (3) effects of partly alleviating (preferably, eliminating) one symptom or more related to a disease. A therapeutically effective amount may be empirically determined by testing a compound in in vivo and in vitro model systems publicly known for a disease requiring treatment.

The expression "carrier" is defined as a compound aiding in application of a compound to cells or tissues. For example, dimethyl sulfoxide (DMSO) is a conventional carrier facilitating addition of a variety of organic compounds to cells or tissues of organisms.

The expression "diluent" is defined as a compound stabilizing biological activity of a subject compound and diluted in water including the compound. In the art, a buffer solution including a dissolved salt is used as a diluent. As a conventionally used buffer solution, there is a phosphate buffered solution imitating a salt concentration of the human body. Since a buffer salt may control pH of a solution at low concentration, a buffer diluent has little effect on biological activity of a compound.

The compounds used in the present invention may be administered alone or as a pharmaceutical composition including other active ingredients, or proper carriers or vehicles. In this regard, technologies related to formulations and administration methods of compounds may be found in "Remington's Pharmaceutical Sciences," Mack Publishing Co., Easton, Pa., 18th edition, 1990.

The pharmaceutical composition according to the present invention may be prepared by publicly known methods using conventional mixing, dissolution, granulation, conservation, pulverization, emulsification, encapsulation, trapping, freeze-drying, or the like.

Therefore, the pharmaceutical composition according to the present invention may be prepared by a conventional method using at least one therapeutically acceptable carrier including vehicles or additives helping to prepare an active compound into a pharmaceutically acceptable formulation. A suitable formulation is determined according to a selected administration manner. Publicly known technology and any carriers and vehicles may be suitably used according to methods known in the art, for example, methods described in Remington's Pharmaceutical Sciences. The compound of Formula (1) according to the present invention may be formulated into an injectable formulation, an oral formulation, or the like.

For injectable formulation, the ingredients according to the present invention may be formulated into a liquid, preferably a therapeutically proper buffer such as Hank's solution, Ringer's solution, or a saline solution. For mucosal penetration administration, a non-penetrative agent suitable for a penetrated barrier is used in a formulation. Such non-penetrative agents are publicly known in the art.

For oral administration, compounds may be easily formulated by combining therapeutically acceptable carriers publicly known in the art with active compounds. Such carriers help the compounds according to the present invention to be formulated into tablets, drugs, powders, granules, confectioneries, capsules, liquids, gels, syrups, slurries, suspensions, and the like, preferably capsules, tablets, pills, powders, and granules, more particularly capsules. Tablets and pills are preferably prepared in enteric coating. Drug preparation for oral administration may be performed by mixing one compound or more according to the present invention with one vehicle or more. In some cases, tablets or confection cores may be obtained by pulverizing a reaction product mixture and treating a granule mixture after selectively adding a proper additive. As proper vehicles, there are fillers such as lactose, sucrose, mannitol, or sorbitol, corn starch, wheat starch, rice starch, potato starch, gelatin, gum tragacanth, methylcellulose, hydroxypropyl methylcellulose, sodium carboxymethylcellulose, and/or a cellulose based material such as polyvinylpyrrolidone (PVP). As needed, a disintegrating agent such as crosslinked polyvinyl pyrrolidone, agar, or alginic acid or salts thereof such as alginic acid sodium, a lubricant such as magnesium stearate, or a carrier such as a binder may be added thereto.

Examples of pharmaceutical preparations used for oral administration include a smooth sealed capsule prepared from gelatin and a plasticizer such as glycol or sorbitol, and a hard-shelled capsule prepared from gelatin. The hard-shelled capsule is prepared from a mixture of a filler such as lactose, a binder such as starch, and/or a lubricant such as talc or magnesium stearate and may include active ingredients. In a soft capsule, active compounds may be dissolved or dispersed in proper solutions such as fatty acids, liquid paraffin, or liquid polyethylene glycol. In addition, a stabilizer may be included therein. All preparations for oral administration must have a content suitable for such administration.

The compounds may be formulated for parenteral administration by injection, e.g., by bolus injection or continuous infusion. A formulation for injection may be provided in a unit amount type using, for example, an ampoule including a preservative or a multi-dose container. A composition may be an oil or liquid vehicle-type suspension, a solution, or an emulsion and may include ingredients such as a suspension, a stabilizer and/or a dispersant for a formulation.

In addition, active ingredients may be powders for application of a proper vehicle such as water as a sterilized non-pyrogenic material such as water before application.

The compounds, for example, may be formulated into compositions for rectal administration such as suppositories or retention enema agents including conventional suppository substrates such as cocoa butter or other glycerides.

A pharmaceutical composition suitable for the present invention includes a composition containing active ingredients in effective amounts to accomplish an intended object thereof. More particularly, the expression "therapeutically effective amount" means an amount effective for preservation of a treated subject or prevention, reduction, or alleviation of disease symptoms. The therapeutically effective amount may be determined by a person skilled in the art.

When formulated in a unit amount, the compound of Formula (1) as an active ingredient is preferably included in a unit amount of approximately 0.1 to 1,000 mg. An administration amount of the compound of Formula (1) is determined according to prescription by a physician considering the weight and age of a patient, and characteristics and severity of a disease. However, a general administration amount required for adult treatment is approximately 1 to 1000 mg per day depending on a frequency and intensity of administration. In adults, a total administration amount intramuscularly or intravenously administered per day is approximately 1 to 500 mg and some patients are preferably administered a higher amount.

The metabolic diseases according to the present invention may be obesity, fatty liver syndrome, arteriosclerosis, stroke, myocardial infarction, cardiovascular disorders, ischemic heart diseases, diabetes, hyperlipidemia, hypertension, retinitis or renal failure, Huntington's disease, or inflammation, particularly fatty liver syndrome, diabetes, or Huntington's disease, but the present invention is not limited thereto.

In addition, the present invention provides a method of treating or preventing metabolic syndromes using a therapeutically effective amount of the compound of Formula (1) according to claim 1 or a pharmaceutically acceptable salt, hydrate, solvate, tautomer, enantiomer, or pharmaceutically acceptable diastereomer thereof. The expression "treating" means that progression of a disease is stopped or delayed when applied to a subject having disease symptoms and the expression "preventing" means that onset of a disease is stopped or delayed by applying to a subject having high disease onset risk although disease symptoms are not yet exhibited.

Advantageous Effects

As described above, a novel 1,2-naphthoquinone derivative according to the present invention causes system improvement through mitochondrial biosynthesis due to mitochondrial activation and change in motor muscle fiber related to endurance by inducing genetic changes typical of long-term calorie restriction and exercise such as activation of AMPK as an energy consumption mechanism according to energy environment change in cells, expression of PGC1a activating energy metabolism of mitochondria, and the like through increase in a ratio of NAD(P)+/NAD(P)H through NQO1 activity in vivo so as to exhibit exercise imitation effects. Therefore, a drug using the novel 1,2-naphthoquinone derivative as an effective ingredient may be usefully used to treat or prevent metabolic syndromes.

BRIEF DESCRIPTION OF THE DRAWINGS

The above and other objects, features and other advantages of the present invention will be more clearly understood from the following detailed description taken in conjunction with the accompanying drawing, in which.

MODE FOR INVENTION

Figure 1:
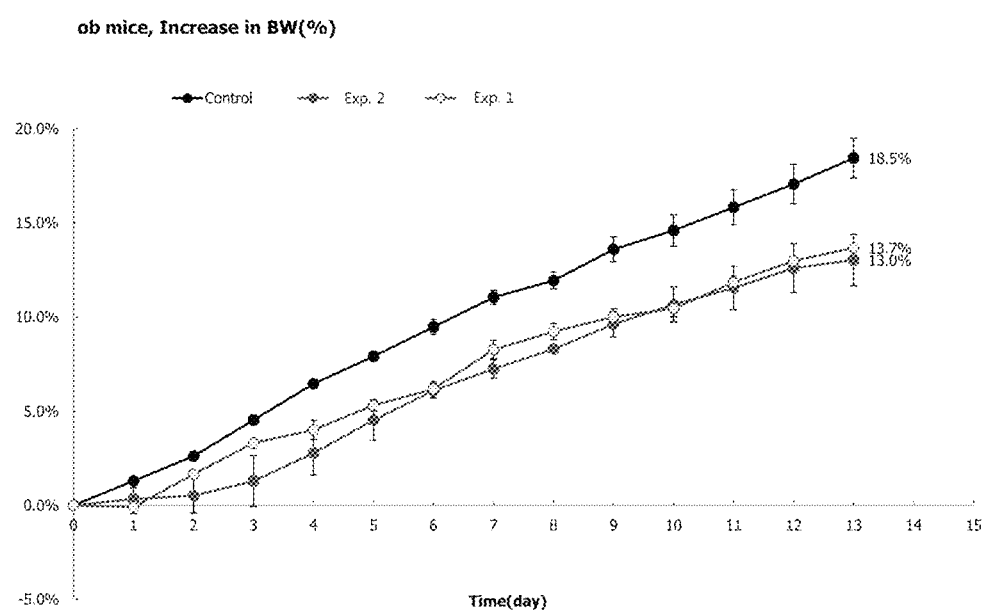
FIG. 1 illustrates graphs representing weight increase ratios in obese mice (ob/ob) administered a compound according to Example 1, a compound according to Example 2, and a control in Experimental Example 3-1.

Now, the present invention will be described in more detail with reference to the following examples. These examples are provided only for illustration of the present invention and should not be construed as limiting the scope and spirit of the present invention. In examples below, methods of preparing intermediates to prepare final compounds and methods of preparing final compounds using the intermediates will be describe.

Example 1. [Synthesis of Compound 1]

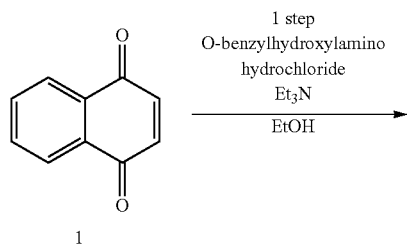

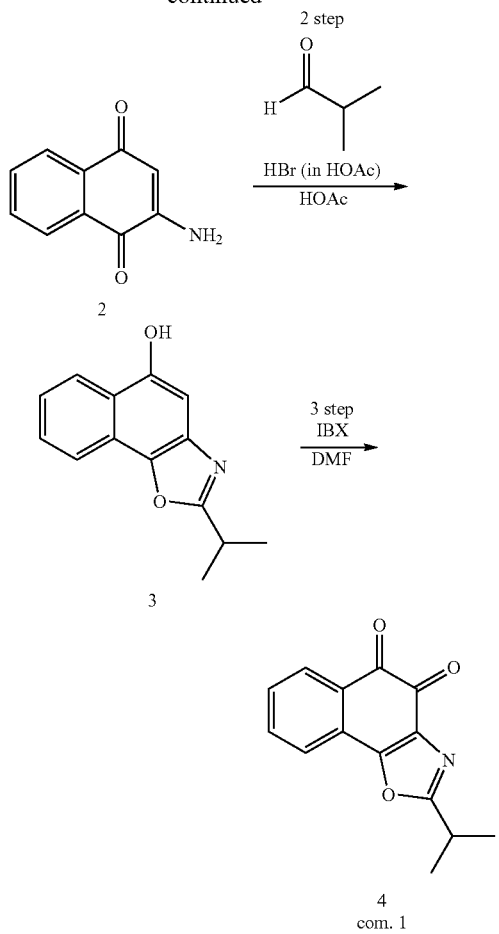

Step 1: 2-aminonaphthalene-1,4-dione 145 ml of ethanol was added to O-benzylhydroxylamine hydrochloride 8 g (50.12 mmol) and stirred at 0° C., thereby generating a white solid. 7 ml of triethylamine (50.12 mmol) was added thereto, followed by stirring until a solid was completely dissolved. 9.5 g of 1,4-naphthoquinone (60.15 mmol) was dissolved in 55 ml of ethanol and then added to the reaction product. Stirring was performed for 23 hours at room temperature. When ethanol was slightly evaporated, an orange solid was filtered out. The filtrate was subjected to column chromatography (hexane:ethyl acetate=3:1).

Orange Solid 7.16 g (82%)

(70% (filter)+12% (column chromatography))

Step 2: 2-isopropylnaphtho[2,1-d]oxazol-5-ol 58 ml of acetic acid was added to 3 g of 2-aminonaphthalene-1,4-dione (17.32 mmol) and stirred at room temperature. When 3 ml of HBr (33 wt % in acetic acid) was added thereto, a solid was dissolved and then an orange solid was generated again. When 8 ml of isobutyraldehyde (86.6 mmol) was slowly added thereto, the reaction product was changed into a purple solution. Stirring was performed for 16 hours at room temperature, and then aq. NaHCO$_3$ was added thereto and neutralization was performed. Extraction was performed using EA. Subsequently, vacuum evaporation and purification through recrystallization in Hex/EA were performed.

Light Pink Solid 2.3 g (58%)

$^1$H NMR (300 MHz, CDCl$_3$) δ 9.88 (s, 1H), 8.25 (d, J=8.4 Hz, 1H), 7.93 (d, J=8.0 Hz, 1H), 7.66-7.61 (m, 1H), 7.52-7.48 (m, 1H), 6.98 (s, 1H), 2.95-2.90 (m, 1H), 1.38 (s, 3H), 1.36 (s, 3H)

Step 3: 2-isopropylnaphtho[2,1-d]oxazole-4,5-dione 132 ml of DMF was added to 2-isopropylnaphtho[2,1-d]oxazol-5-ol 1.5 g (6.6 mmol) and stirred at room temperature. 2-iodoxybenzoic acid (IBX) (45 wt %) 4.9 g (7.9 mmol) was added thereto, followed by stirring for 4 hours at room temperature. EA was added thereto and washing was performed with H$_2$O several times. The organic layer was treated with MgSO$_4$ and then filtration was performed through silica gel (washing with ethyl acetate). The filtrate was vacuum evaporated and then recrystallization was performed using Hex/EA.

Shining Orange Solid 77%

$^1$H NMR (300 MHz, CDCl$_3$) δ 8.15 (d, J=7.9 Hz, 1H), 7.72-7.70 (m, 2H), 7.58-7.52 (m, 1H), 3.29-3.22 (m, 1H), 1.48 (s, 3H), 1.46 (s, 3H)

Example 2. [Synthesis of Compound 2]

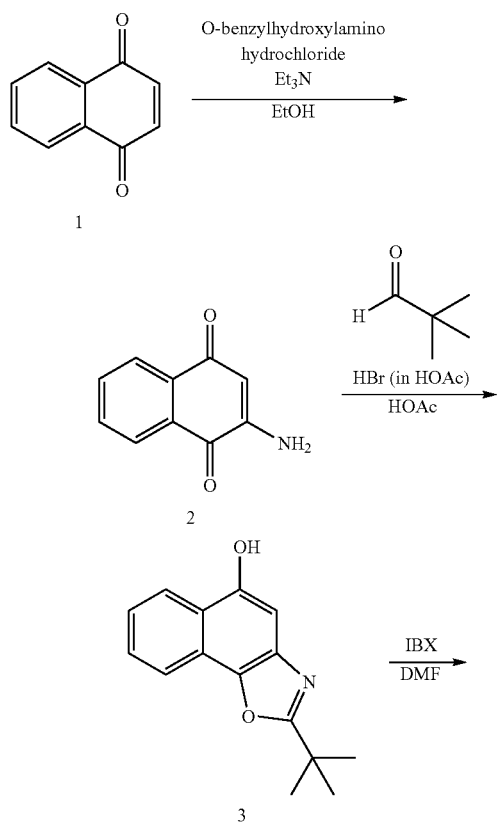

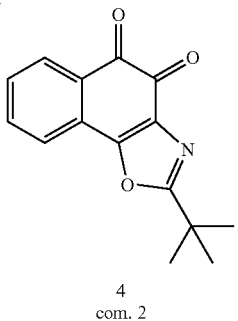

1→2

A synthesis method thereof was the same as that of Compound 1

2→3 (2-tert-butylnaphtho[2,1-d]oxazol-5-ol)

40 ml of acetic acid was added to 2 g of 2-aminonaphthalene-1,4-dione (11.55 mmol) and stirred at room temperature. 2 ml of HBr (33 wt % in acetic acid) was added thereto and then 3.8 ml of pivaldehyde (34.65 mmol) was slowly added thereto. Stirring was performed for 16 hours at room temperature, and then aq. NaHCO$_3$ was added thereto and neutralization was performed. Extraction was performed using EA. Sunsequently, vacuum evaporation using purification through recrystallization in Hex/EA were performed.

Opaque Pink Solid 59%

$^1$H NMR (300 MHz, CDCl$_3$) δ 8.50 (br, s, 1H), 8.24 (d, J=8.4 Hz, 1H), 7.92 (d, J=8.1 Hz, 1H), 7.61-7.56 (m, 1H), 7.50-7.45 (m, 1H), 7.05 (s, 1H), 1.50 (s, 9H)

3→4 (2-tert-butylnaphtho[2,1-d]oxazole-4,5-dione)

108 ml of DMF was added to 2-tert-butylnaphtho[2,1-d]oxazol-5-ol 1.3 g (5.39 mmol) and stirred at room temperature. 3.85 g of 2-iodoxybenzoic acid (IBX) (45 wt %) (6.46 mmol) was added thereto, followed by stirring for 4 hours at room temperature. When the reaction was completed, EA was added thereto and washing was performed with H$_2$O several times. The organic layer was treated with MgSO$_4$ and then filtration was performed through silica gel (washing with ethyl acetate). The filtrate was vacuum evaporated and then recrystallized in Hex/EA.

Light Orange Solid 68%

$^1$H NMR (300 MHz, CDCl$_3$) δ 8.14 (d, J=7.7 Hz, 1H), 7.73-7.69 (m, 2H), 7.58-7.52 (m, 1H), 1.50 (s, 9H)

Example 3. [Synthesis of Compound 3]

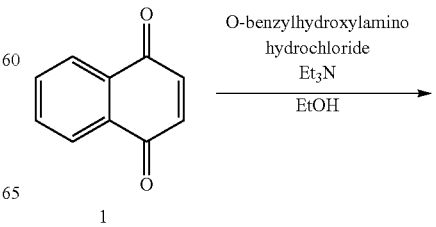

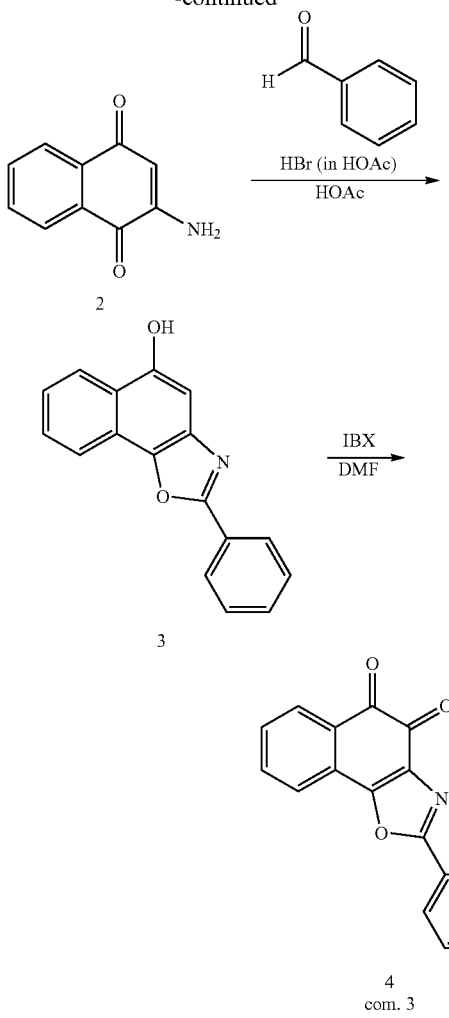

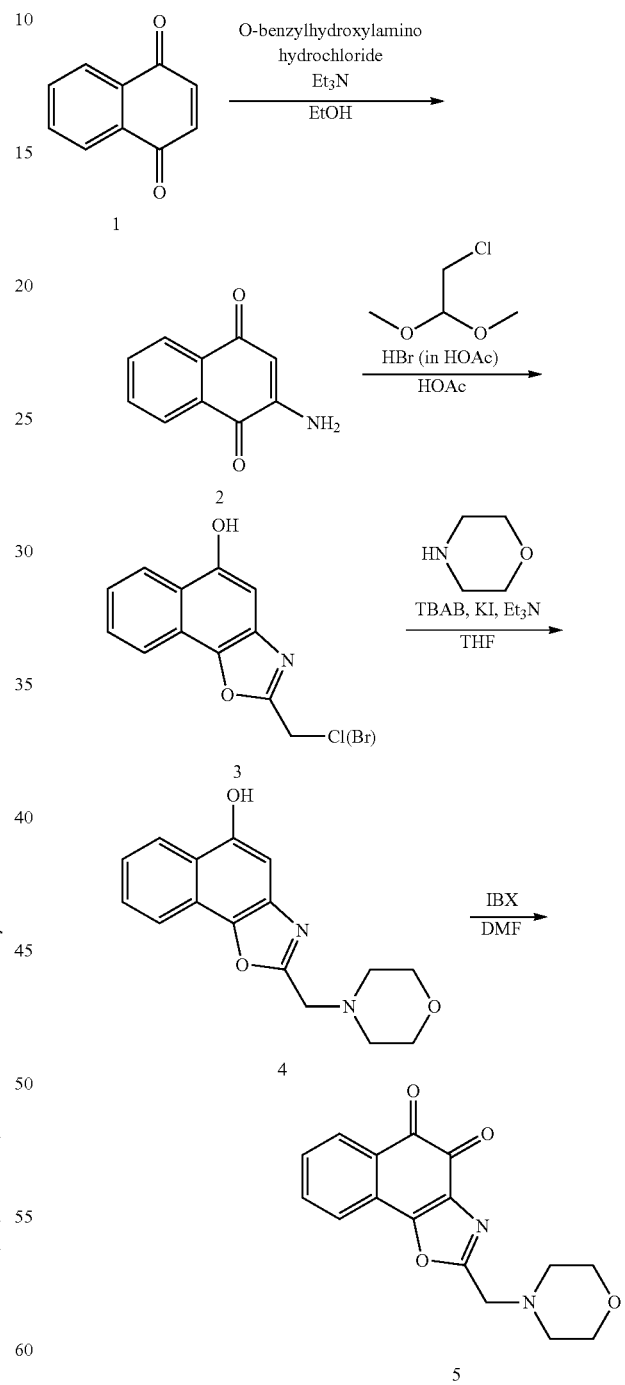

1→2

A synthesis method thereof was the same as that of Compound 1

2→3 (2-phenylnaphtho[2,1-d]oxazol-5-ol)

40 ml of acetic acid was added to 2-aminonaphthalene-1,4-dione 2 g (11.55 mmol) and stirred at room temperature. 2 ml of HBr (33 wt % in acetic acid) was added thereto and then 3.5 ml of benzaldehyde (34.65 mmol) was slowly added thereto. Stirring was performed for 16 hours at room temperature, and then aq. $NaHCO_3$ was added thereto and neutralization was performed. Extraction was performed using EA. Sunsequently, vacuum evaporation and purification through recrystallization in Hex/EA were performed.

3→4 (2-phenylnaphtho[2,1-d]oxazole-4,5-dione)

108 ml of DMF was added to 1.3 g of 2-phenylnaphtho[2,1-d]oxazol-5-ol (4.98 mmol) and stirred at room temperature. 3.7 g of 2-iodoxybenzoic acid (IBX) (45 wt %) (5.97 mmol) was added thereto, followed by stirring for 4 hours at room temperature. When the reaction was completed, EA was added thereto and washed with $H_2O$ several times. The organic layer was treated with $MgSO_4$ and then filtration was performed through silica gel (washing with ethyl acetate). The filtrate was vacuum evaporated and then recrystallized in Hex/EA.

Example 4. [Synthesis of Compound 4]

2→3 (2-(chloromethyl)naphtho[2,1-d]oxazol-5-ol)

20 ml of acetic acid and HBr (33 wt % in acetic acid) were added to 8.7 ml of 2-chloro-1,1-dimethoxyethane (76.24 mmol) and stirred for 5 minutes at room temperature. 2 g of 2-aminonaphthalene-1,4-dione (15.25 mmol) was dissolved in 31 ml of acetic acid and then added to the reaction product. The reaction product was stirred for 24 hours at room temperature. Aq. NaHCO₃ was added thereto and neutralization was performed, and then extraction was performed using EA. The organic layer was treated with MgSO₄, filtered, and vacuum evaporated, and then purification was performed by recrystallization in Hex/EA. A filtrate was evaporated and subjected to column chromatography.

Ivory Solid 36% (Likely a Mixture of Cl and Br)

3→4 (2-(morpholinomethyl)naphtho[2,1-d]oxazol-5-ol)

3.3 ml of THF was added to 0.1 g of 2-(chloromethyl)naphtho[2,1-d]oxazol-5-ol (0.43 mmol) and stirred at room temperature. 21 mg of KI (30 mol %) and 0.12 ml of triethylamine (0.86 mmol), 0.2 ml of morpholine (0.86 mmol), and 27 mg of tetrabutylammonium bromide (TBAB) (0.086 mmol) were added thereto. The reaction product was stirred for 6.5 hours at room temperature. Extraction was performed by adding EA and water, and then the organic layer was treated with MgSO₄, filtered, and vacuum evaporated.

Light Orange Solid 87%

4→5 (2-(morpholinomethyl)naphtho[2,1-d]oxazole-4,5-dione)

49 ml of DMF was added to 2-(morpholinomethyl)naphtho[2,1-d]oxazol-5-ol 0.7 g (2.46 mmol) and stirred at room temperature. 1.8 g of IBX (2.95 mmol) was added thereto and then stirred for 3 hours at room temperature. DMF was evaporated and workup was performed using EA:H₂O, and then the organic layer was treated with MgSO₄, filtered, and vacuum evaporated, and column chromatography (CHCl₃:CH₃OH=15:1) was performed.

Opaque Yellow Solid 74%

¹H NMR (300 MHz, CDCl₃) δ 8.17 (d, J=7.7 Hz, 1H), 7.78-7.70 (m, 2H), 7.60-7.55 (m, 1H), 3.85 (s, 2H), 3.78-3.74 (m, 4H), 2.68-2.65 (m, 4H)

Example 5. [Synthesis of Compound 5]

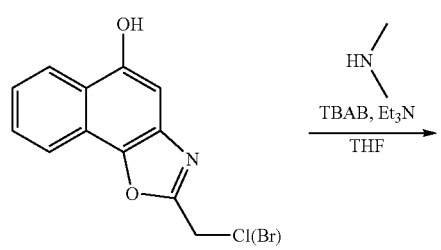

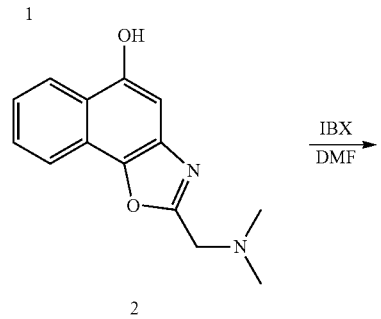

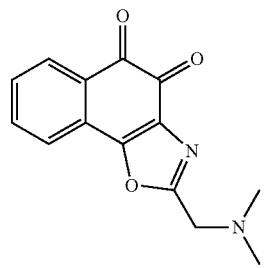

1→2 (2-((dimethylamino)methyl)naphtho[2,1-d]oxazol-5-ol)

6.6 ml of THF was added to 2-(chloromethyl)naphtho[2,1-d]oxazol-5-ol 0.2 g (0.86 mmol) and stirred at room temperature. 55 mg of tetrabutylammonium bromide (TBAB) (0.17 mmol), 0.48 ml of triethylamine (3.44 mmol), and 0.14 g of dimethylamine hydrochloride (1.72 mmol) were added thereto, followed by stirring for 24 hours at room temperature. EA and water were added thereto and extraction was performed, and then the organic layer was treated with MgSO₄, filtered, and vacuum evaporated, and column chromatography (CHCl₃:CH₃OH=20:1) was performed.

Light Brown Solid 67%

2→3 (2-((dimethylamino)methyl)naphtho[2,1-d]oxazole-4,5-dione)

10 ml of DMF was added to 0.12 g of 2-((dimethylamino)methyl)naphtho[2,1-d]oxazol-5-ol) (0.5 mmol) and stirred at room temperature. IBX 0.35 g (0.6 mmol) was added thereto and then stirred for 3 hours at room temperature. DMF was evaporated and workup was performed using EA:H₂O, and then the organic layer was treated with MgSO₄, filtered, and vacuum evaporated, and column chromatography (CHCl₃:CH₃OH=15:1) was performed.

Yellow Solid 90%

¹H NMR (300 MHz, CDCl₃) δ 8.16 (d, J=7.7 Hz, 1H), 7.79-7.69 (m, 2H), 7.60-7.54 (m, 1H), 3.80 (s, 2H), 2.42 (s, 6H)

Example 6. [Synthesis of Compound 6]

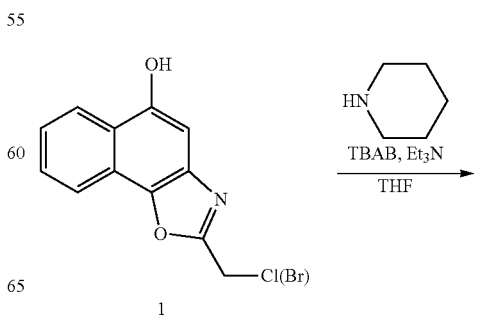

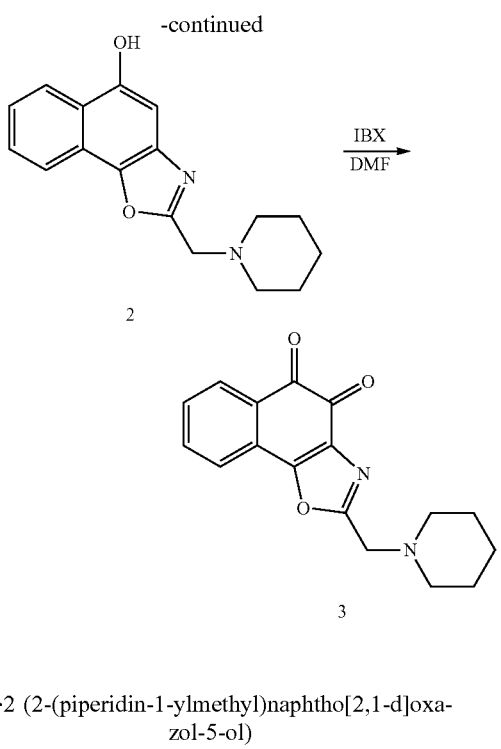

1→2 (2-(piperidin-1-ylmethyl)naphtho[2,1-d]oxazol-5-ol)

6.6 ml of THF was added to 0.2 g of 2-(chloromethyl)naphtho[2,1-d]oxazol-5-ol (0.86 mmol) and stirred at room temperature. 55 mg of tetrabutylammonium bromide (TBAB) (0.17 mmol), 0.24 ml of triethylamine (1.72 mmol), and 0.17 ml of piperidine (1.72 mmol) were added thereto, followed by stirring for 48 hours at room temperature. EA and water were added thereto and extraction was performed, and then the organic layer was treated with MgSO₄, filtered, and vacuum evaporated, and column chromatography (CHCl₃:CH₃OH=10:1) was performed.

Light Brown Solid 69%

2→3 (2-(piperidin-1-ylmethyl)naphtho[2,1-d]oxazole-4,5-dione)

11 ml of DMF was added to 0.155 g of 2-(piperidin-1-ylmethyl)naphtho[2,1-d]oxazol-5-ol (0.55 mmol) and stirred at room temperature. IBX 0.39 g (0.66 mmol) was added thereto and then stirred for 1 hour at room temperature. DMF was evaporated and workup was performed using EA:H₂O, and then the organic layer was treated with MgSO₄, filtered, and vacuum evaporated, and column chromatography (CHCl₃:CH₃OH=15:1) was performed.

Opaque Yellow Solid 55%

¹H NMR (300 MHz, CDCl₃) δ 8.16 (d, J=8.0 Hz, 1H), 7.79-7.69 (m, 2H), 7.59-7.57 (m, 1H), 3.83 (s, 2H), 2.58 (m, 4H), 1.68-1.60 (m, 4H), 1.47-1.45 (m, 2H)

Example 7. [Synthesis of Compound 7]

2-isopropyl-6,9-dimethyloxazolo[5,4-f]quinoline-4,5,7(6H)-trione

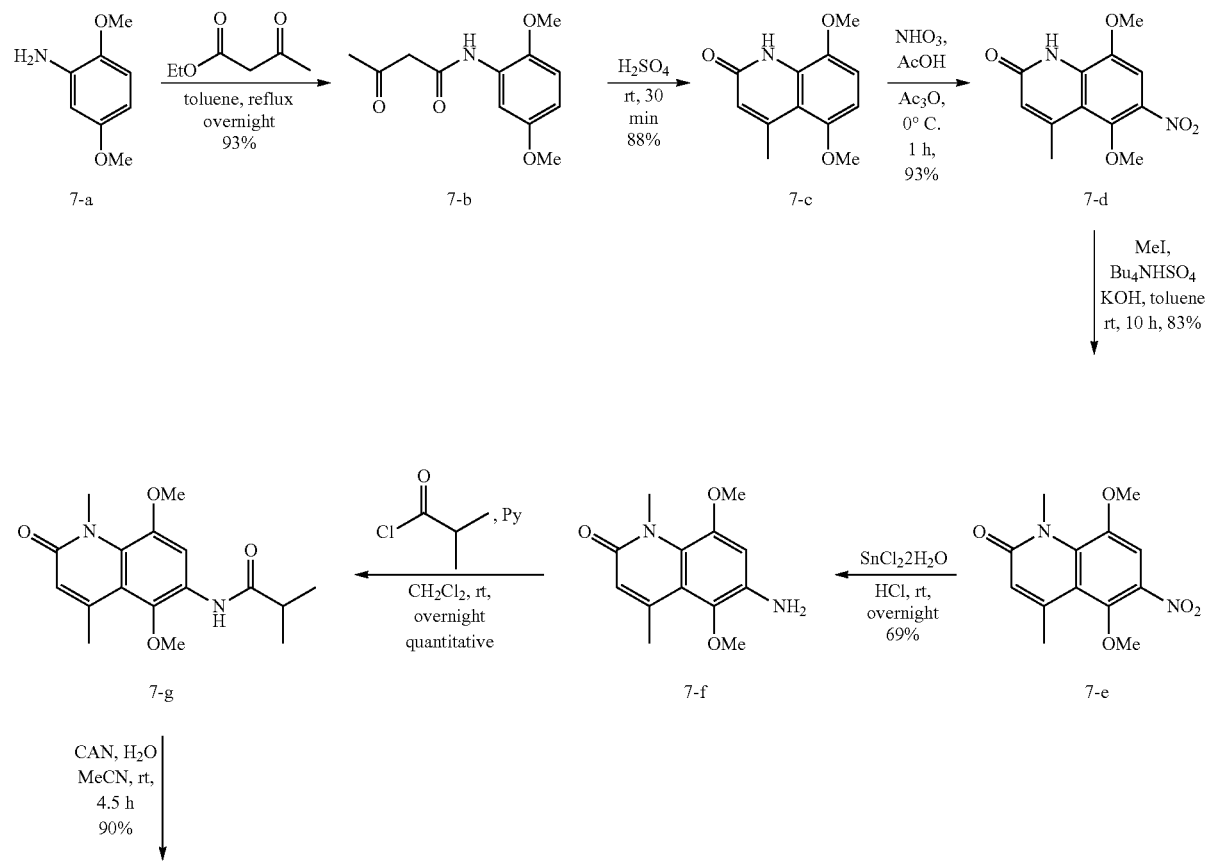

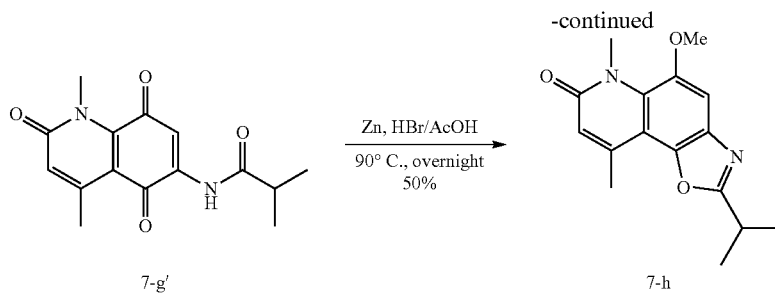 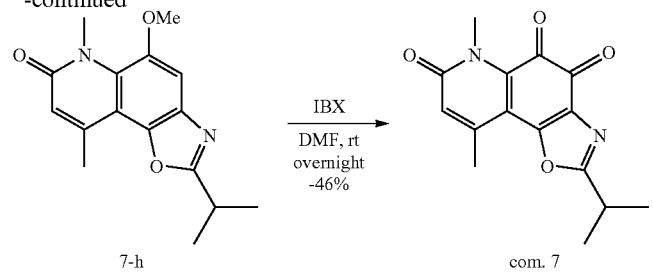

Synthesis of Compound 7-b

Compound 7-a (2,5-dimethoxyaniline, 10.0 g, 65.28 mmol) was dissolved in toluene (130 ml) and then ethyl acetoacetate (8.3 ml, 65.28 mmol) was added thereto. A Dean-Stark apparatus was installed, followed by refluxing overnight. Toluene was evaporated after terminating reaction and then a crude product was purified through column chromatography {Ethyl acetate (EA):hexane (HX)=1:1} and recrystallization.

Yield: 93%

1H NMR (300 MHz, CD Cl$_3$): 2.31 (3H, s), 3.59 (2H, s), 3.76 (3H, s), 3.85 (3H, s), 6.57 (1H, dd, J=2.9, 8.8 Hz), 6.79 (1H, d, J=8.8 Hz), 8.06 (1H, d, J=2.9 Hz), 9.29 (1H, brs)

Synthesis of Compound 7-c

Compound 7-b (10.0 g, 42.15 mmol) was added to strong sulfuric acid (42 ml) and stirred for 30 minutes at room temperature. A reaction solution was slowly added to ice water, and then an aqueous 25% NH$_4$OH solution was added dropwise thereto while stirring. A brown solid was filtered and then washed with distilled water. Subsequently, recrystallization was performed using EA, thereby obtaining approximately 8.1 g of a solid.

Yield: 88%

1H NMR (300 MHz, CDCl$_3$): 2.63 (3H, s), 3.84 (3H, s), 3.91 (3H, s), 6.39 (1H, s), 6.51 (1H, d, J=8.8 Hz), 6.87 (1H, d, J=8.8 Hz), 9.11 (1H, brs)

Synthesis of Compound 7-d

Acetic anhydride (33 ml) was added to Compound 7-c (5.0 g, 22.81 mmol) and then a mixture of 70% nitric acid (2.2 ml, 34.21 mmol) and glacial acetic acid (6.6 ml) was added thereto dropwise at 0° C. A reaction solution was stirred for one hour at 0° C. Distilled water was added to the reaction solution, neutralization was performed using saturated aqueous NaHCO$_3$, and then extraction was performed using methylene chloride (MC). An organic layer was separated, and then dried over MgSO$_4$ and filtered. The filtrate was vacuum evaporated and then recrystallized using acetone and HX, thereby obtaining approximately 5.6 g of a yellow solid.

Yield: 93%

1H NMR (300 MHz, CDCl$_3$): 2.70 (3H, s), 3.89 (3H, s), 4.04 (3H, s), 6.56 (1H, s), 7.54 (1H, s), 9.36 (1H, brs)

Synthesis of Compound 7-e

Compound 7-d (0.2 g, 0.76 mmol) was dissolved in toluene (7.5 ml) and then an aqueous 50% KOH (KOH: 76 mg, 1.36 mmol) solution and Bu$_4$NHSO$_4$ (51 mg, 0.15 mmol) were added thereto. After 15 minutes, MeI (71 microliters, 1.14 mmol) was added to a reaction solution and then stirred for 10 hours at room temperature. After completing reaction, distilled water (2.5 ml) was added thereto and an organic layer was separated and dried over MgSO$_4$. Subsequently, filtration was performed. The filtrate was vacuum evaporated and then purified through column chromatography.

Yield: 83%

1H NMR (300 MHz, CDCl$_3$): 3.65 (3H, s), 3.85 (3H, s), 3.86 (3H, s), 3.95 (3H, s), 6.61 (1H, s), 7.61 (1H, s)

Synthesis of Compound 7-f

Compound 7-e (158 mg, 0.60 mmol) was added to an aqueous 35% hydrochloric acid solution (4 ml), and then SnCl$_2$2H$_2$O (0.68 g, 2.99 mmol) was added thereto, followed by stirring overnight at room temperature. A reaction solution was basified using saturated aqueous NaHCO$_3$ and then extracted using MC. The separated organic layer was dried over MgSO$_4$ and then filtered. The filtrate was vacuum evaporated and then recrystallized in EA and HX.

Yield 69%

Synthesis of Compound g

Compound 7-f (25 mg, 0.10 mmol) was dissolved in MC (1 ml), and then pyridine (12 microliters, 0.15 mmol) and isobutyryl chloride (13 microliters, 0.12 mmol) were added thereto, followed by stirring at room temperature overnight. Distilled water was added to a reaction solution and then an organic layer was washed with 1 M HCl and saturated aqueous NaHCO$_3$. Subsequently, the organic layer was dried over MgSO$_4$ and filtered. The filtrate was vacuum evaporated and then purified through column chromatography (EA, HX).

Quantitative Yield

1H NMR (300 MHz, CDCl$_3$): 1.27 (6H, d, J=6.6 Hz), 2.54 (3H, s), 3.60-3.85 (7H, m), 6.47 (1H, s), 7.78 (1H, s), 8.19 (1H, s)

Synthesis of Compound 7-g'

Compound 7-g (80 mg, 0.25 mmol) was dissolved in acetonitrile (2 ml) and distilled water (0.8 ml) and then ceric ammonium nitrate (0.41 g, 0.75 mmol) was added thereto. A reaction solution was stirred for 4.5 hours at room temperature and then acetonitrile was vacuum evaporated. Subsequently, distilled water was added thereto and extraction was performed using MC. An organic layer was separated, dried over MgSO$_4$, and filtered. The filtrate was vacuum evaporated.

Yield: 90%

1H NMR (300 MHz, CDCl$_3$): 1.27 (6H, d, J=7.0 Hz), 2.57 (3H, s), 2.65 (1H, septet, J=7.0 Hz), 3.87 (3H, s), 6.62 (1H, s), 7.64 (1H, s), 8.40 (1H, brs)

Synthesis of Compound 7-h

Compound 7-g' (53 mg, 0.18 mmol) and acetic acid (1.2 ml) were mixed, and then HBr/AcOH (33%, 0.17 ml, 0.92 mmol) and Zn (36 mg, 0.55 mmol) were added thereto, followed by stirring at 90° C. After 18 hours, Zn (24 mg, 0.37 mmol) was additionally added thereto and further stirred for one day. Temperature was lowered to room temperature, and then water and MC were added thereto and extracted. Subsequently, an MC layer was washed with water. An organic layer was dried over MgSO$_4$ and filtered. The filtrate was vacuum evaporated and then purified through column chromatography (EA, HX).

Yield: 50%

1H NMR (300 MHz, CDCl$_3$): 1.48 (6H, d, J=7.0 Hz), 2.73 (3H, s), 3.29 (1H, septet, J=7.0 Hz), 4.02 (3H, s), 6.62 (1H, s), 7.38 (1H, s)

Compound 7

Compound 7-h (12.5 mg, 45.91 μmol) was dissolved in DMF (0.6 ml), and then IBX (33 mg, 55.09 μmol) were added thereto, followed by stirring at room temperature. One day later, DMF was vacuum concentrated and distilled water and MC were added thereto. An MC layer was washed with saturated aqueous NaHCO$_3$ and then dried over MgSO$_4$. Subsequently, filtration was performed. The filtrate was vacuum evaporated and then purified through column chromatography (EA, HX).

Yield~46%

1H NMR (300 MHz, CDCl$_3$): 6.78 (s, 1H), 3.83 (s, 3H), 3.21 (m, 1H), 2.58 (s, 3H), 1.44 (d, J=7.0 Hz, 6H)

Examples 8 and 9. [Synthesis of Compounds 8 and 9]

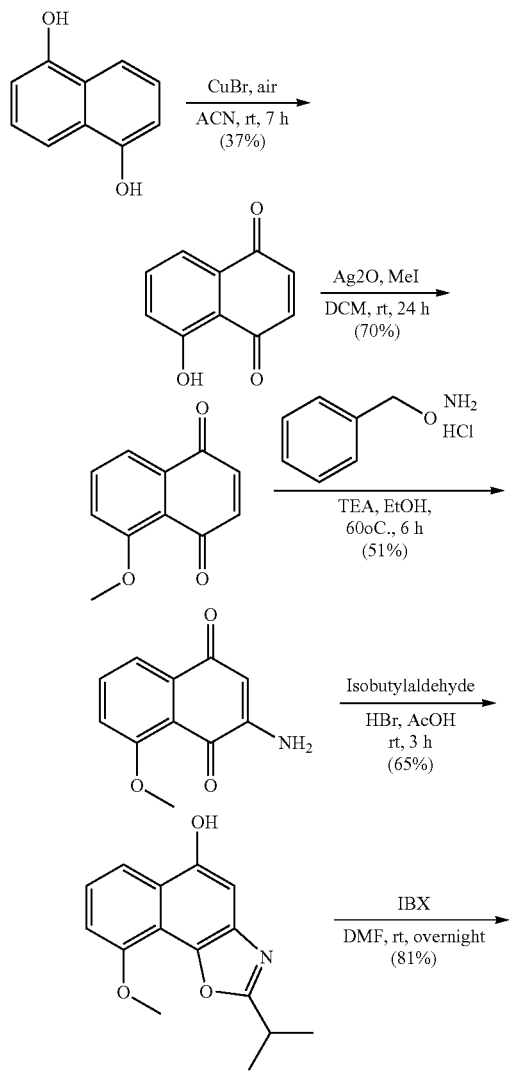

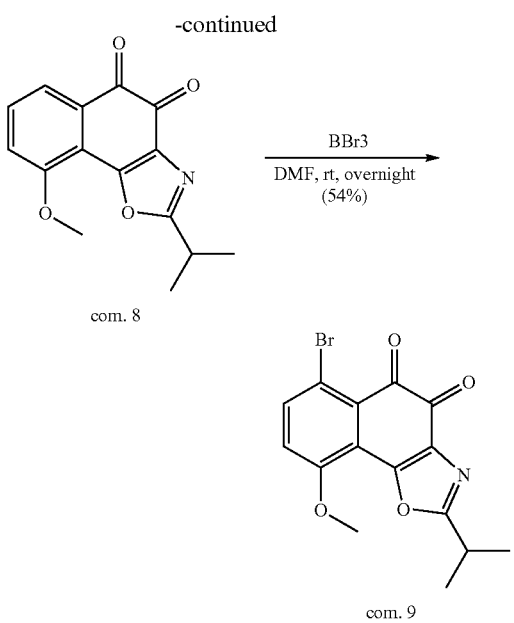

1. Synthesis of Juglone

At room temperature, CuBr (7 g, 48.69 mmol) was added to a two-neck 500 ml RB and dissolved in MeCN (300 ml) as a solvent, and then air bubbling was performed. In addition, 1,5-naphthalenediol (12 g, 74.92 mmol) was dissolved in MeCN and a reaction product solution was added to RB. In addition, stirring was vigorously performed in the dark. After reaction for 7 hours, filtration was performed and all solvent was evaporated using a vacuum filtration device. Subsequently, separation and purification were performed through flash column chromatography, thereby obtaining 4.85 g of juglone (37%).

$^1$H NMR (300 MHz, CDCl$_3$): δ=6.96 (s, 2H), 7.29 (dd, J=6.3, 2.9 Hz, 1H), 7.64 (m, 2H), 12.01 (s, 1H)

2. Synthesis of O-methyljuglone

At room temperature, juglone (1.8 g, 10.34 mmol) and Ag$_2$O (1.9 g, 8.27 mmol) were dissolved in DCM (35 ml) and then MeI (0.13 ml, 2.17 mmol) was added thereto. Reaction was performed for 20 h at room temperature. In addition, MeI (0.51 ml, 8.17 mmol) and Ag$_2$O (1.9 g, 8.27 mmol) were added thereto and then reacted for 2 hours at room temperature. In addition, filtration was performed through Celite filter and then separation and purification were performed through flash column chromatography, thereby obtaining 1.36 g of O-methyljuglone (70%).

$^1$H NMR (300 MHz, CDCl$_3$): δ=4.02 (s, 3H), 6.88 (s, 2H), 7.31 (dd, J=7.1, 1.8 Hz, 1H), 7.67 (dd, J=7.9, 7.1 Hz, 1H), 7.72 (dd, J=7.9, 1.8 Hz, 1H)

3. 2-amino-8-methoxynaphthalene-1,4-dione

At room temperature, O-benzylhydroxylamine hydrochloride (1.4 g, 8.696 mmol) was dissolved in 50 ml of EtOH. In addition, temperature was lowered to 0 to 5° C. and then TEA (1.2 ml, 8.696 mmol) was added thereto. In addition, O-methyljuglone dissolved in EtOH was added thereto and reacted overnight at room temperature. After terminating reaction, filtration was performed, an organic layer was separated using DCM, and water was removed using MgSO$_4$. Subsequently, filtration and vacuum concentration were performed. An obtained residue was separated and purified through flash column chromatography, thereby obtaining 2-amino-8-methoxynaphthalene-1,4-dione 1 g (51%).

$^1$H NMR (300 MHz, CDCl$_3$): δ=7.76 (dd, J=7.9, 1.8 Hz, 1H), 7.67 (dd, J=7.9, 7.1 Hz, 1H), 7.22 (dd, J=7.1, 1.8 Hz, 1H), 5.94 (s, 1H), 5.23, (bs, 2H), 4.02 (s, 3H)

4. 2-isopropyl-9-methoxynaphtho[2,1-d]oxazol-5-ol

At room temperature, 2-amino-8-methoxynaphthalene-1,4-dione (1 g, 4.922 mmol) was added to 15 ml of AcOH and HBr (in AcOH, 0.8 ml, 5%) was added thereto. In addition, isobutyraldehyde (2.25 ml, 24.61 mmol) was added thereto and reacted for 3 hours at room temperature. Reaction was terminated by adding water and then an organic layer was separated using EA. Subsequently, water was removed by adding MgSO$_4$, and then filtration and vacuum concentration were performed. An obtained residue was separated and purified through flash column chromatography, thereby obtaining 830 mg of 2-isopropyl-9-methoxynaphtho[2,1-d] oxazol-5-ol (65%).

$^1$H NMR (300 MHz, CDCl$_3$): δ=7.89 (d, J=8.4 Hz, 1H), 7.43 (t, J=8.1 Hz, 1H), 7.20 (s, 1H), 7.01 (d, 8.1 Hz, 1H), 6.13 (s, 1H), 4.02 (s, 3H), 3.41-3.31 (m, 1H), 1.52 (d, 6H)

5. 2-isopropyl-9-methoxynaphtho[2,1-d]oxazole-4,5-dione

At room temperature, 2-isopropyl-9-methoxynaphtho[2,1-d]oxazol-5-ol (0.73 g 2.837 mmol) was dissolved in 20 ml of DMF, and then IBX (1.6 g 5.675 mmol) was added thereto and reacted overnight at room temperature. Reaction was terminated by adding water and then an organic layer was separated using EA. Subsequently, water was removed by adding MgSO4 and then filtration and vacuum concentration were performed. An obtained residue was separated and purified through flash column chromatography, thereby obtaining 630 mg of 2-isopropyl-9-methoxynaphtho[2,1-d] oxazole-4,5-dione (81%).

1H NMR (300 MHz, CDCl$_3$) δ 7.77 (d, J=7.6 Hz, 1H), 7.47 (t, J=8.1 Hz, 1H), 7.25 (d, J=7.6 Hz, 1H), 4.03 (s, 3H), 3.28-3.19 (m, 1H), 1.46 (d, J=7.0 Hz, 6H)

6. 6-bromo-2-isopropyl-9-methoxynaphtho[2,1-d]oxazole-4,5-dione

At room temperature, 2-isopropyl-9-methoxynaphtho[2,1-d]oxazole-4,5-dione (300 mg, 1.106 mmol) was dissolved in DCM 10 ml, and then BBr$_3$ (1.11 ml, 1.106 mmol) was added thereto and reacted overnight at room temperature. Reaction was terminated by adding water and then an organic layer was separated using EA. Subsequently, water was removed by adding MgSO$_4$ and then filtration and vacuum concentration were performed. An obtained residue was separated and purified through flash column chromatography, thereby obtaining 210 mg of 6-bromo-2-isopropyl-9-methoxynaphtho[2,1-d]oxazole-4,5-dione (54%).

$^1$H NMR (300 MHz, CDCl$_3$): δ=7.71 (d, J=9.15 Hz, 1H), 7.09 (d, J=9.15, 1 H), 4.03 (s, 3H), 3.26-3.21 (m, 1H), 1.47 (d, 6H)

Example 10. [Synthesis of Compound 10]

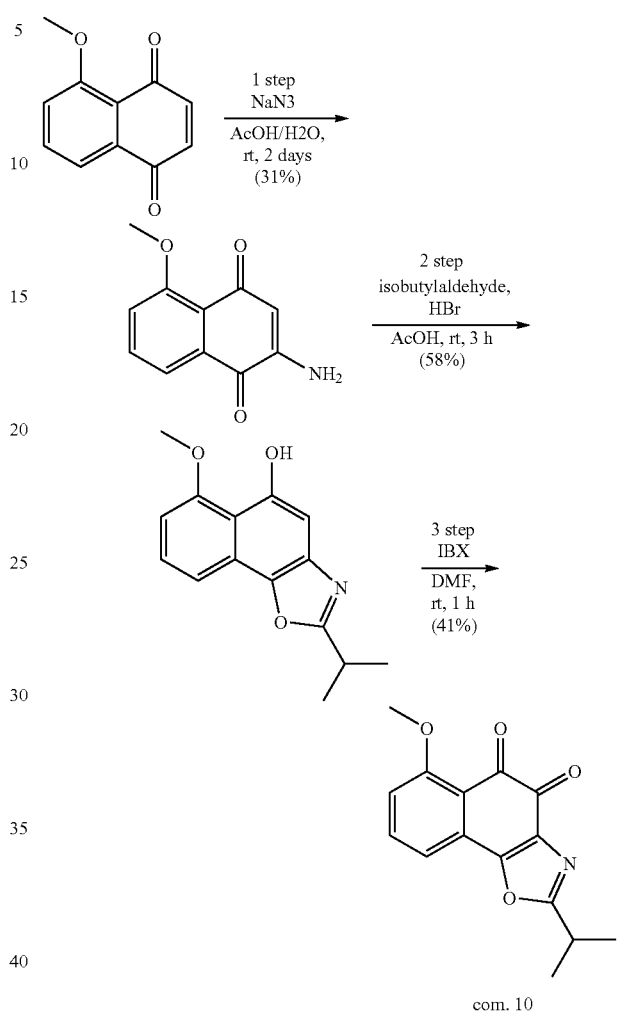

Step 1: Preparation of 2-amino-5-methoxynaphthalene-1,4-dione 3 g of 5-methoxynaphthalene-1,4-dione was added to 60 ml of AcOH and stirred at 0° C. 2.1 g of sodium azide was dissolved in 6 ml of H$_2$O and then added to a flask containing a starting material dropwise. The reaction product was stirred for two days at room temperature. After completing reaction, 300 ml of H$_2$O was added thereto, followed by stirring for 20 minutes at room temperature. Subsequently, filtration was performed. A filtrate was neutralized using aq. NaHCO$_3$ and then extracted using MC. The extract was treated with MgSO$_4$, filtered, and evaporated, and then subjected to column chromatography (H:EA:MC=1:1:0.5)

Solid: 1 g (31%)

$^1$H NMR (300 MHz, CDCl$_3$) δ 7.75 (d, J=7.8 Hz, 1H), 7.59 (t, J=7.8 Hz, 1H), 7.31 (d, J=8.4 Hz, 1H), 5.93 (s, 1H), 4.90 (brs, 2H), 3.99 (s, 3H)

Step 2: 2-isopropyl-6-methoxynaphtho[2,1-d]oxazol-5-ol

AcOH 5 ml was added to 300 mg of 2-amino-5-methoxynaphthalene-1,4-dione (1 eq.), and then 0.25 ml of 33% HBr in AcOH and 0.674 ml of isobutyl aldehyde (5 eq.) were sequentially added thereto at room temperature. The reaction product was reacted for 4 hours at room temperature. When the reaction was completed, neutralization was performed using aq. NaHCO$_3$ and extraction was performed using MC. The extract was treated with MgSO$_4$, filtered, and evaporated, and then subjected to column chromatography (Hex:EA=4-2:1)

Solid: 220 mg (58%)

Step 3: 2-isopropyl-6-methoxynaphtho[2,1-d]oxazole-4,5-dione (Compound 10)

7 ml of DMF was added to 180 mg of 2-isopropyl-6-methoxynaphtho[2,1-d]oxazol-5-ol and IBX 500 mg (1.2 eq.) having a purity of 47% was added thereto while stirring at 40° C. for 2 hours. When the reaction was completed, aq. NaHCO$_3$ was added thereto and extraction was performed using MC several times. An MC layer was treated with MgSO$_4$, filtered, and vacuum concentrated, and then separated through prep TLC (Hex:EA=1:1)

Reddish Brown Solid: 3 mg (9%)

1H NMR (300 MHz, CDCl$_3$) δ 12.02 (s, 1H), 7.59 (t, J=7.2 Hz, 1H), 7.25 (d, J=7.8 Hz, 1H), 7.10 (d, J=9.6 Hz, 1H), 3.23 (m, 1H), 1.46 (d, J=6.9 Hz, 6H)

Example 11. [Synthesis of Compound 11]

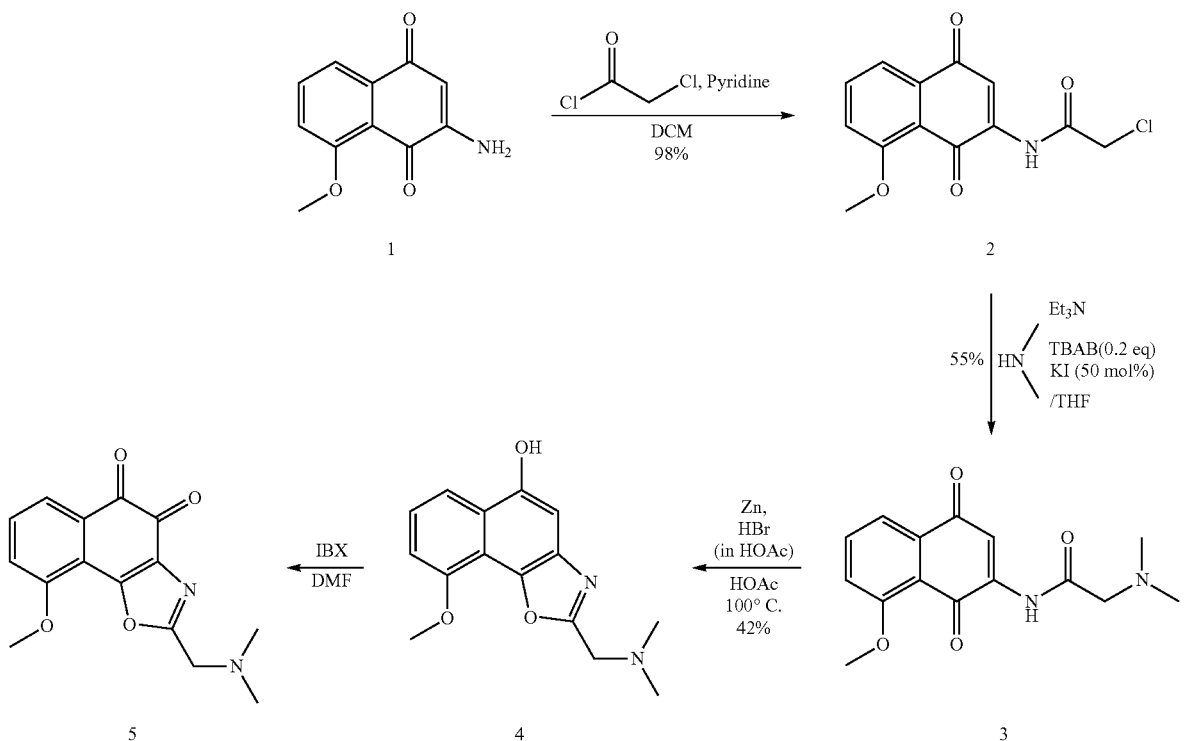

at room temperature. The reaction product was stirred for one hour at room temperature. When the reaction was completed, an excess of EA was added thereto, and washing with aq. NaHCO$_3$ was performed approximately twice to maximally remove DMF. Subsequently, treatment with MgSO$_4$, filtration, and evaporation were performed. When recrystallized, filtration and washing with MC were performed.

Orange Solid: 77 mg (41%)
$^1$H NMR (300 MHz, CDCl$_3$) δ 7.64 (t, J=8.1 Hz, 1H), 7.33 (d, J=7.8 Hz, 1H), 7.13 (d, J=8.4 Hz, 1H), 4.02 (s, 3H), 3.23 (m, 1H), 1.46 (d, J=7.2 Hz, 6H)

Step 4: 6-hydroxy-2-isopropylnaphtho[2,1-d]oxazole-4,5-dione (Compound 15)

35 mg of 2-isopropyl-6-methoxynaphtho[2,1-d]oxazole-4,5-dione was dissolved in 1 ml of dichloromethane (0.1 M), and AlCl$_3$ was added thereto at 0° C. Stirring was performed 1→2 (2-chloro-N-(8-methoxy-1,4-dioxo-1,4-dihydronaphthalen-2-yl)acetamide)

0.65 g of 2-amino-8-methoxynaphthalene-1,4-dione (3.20 mmol) was dissolved in DCM 32 ml and then stirred at room temperature. 0.4 ml of pyridine (4.80 mmol) and chloroacetyl chloride were added thereto, followed by stirring for 16 hours at room temperature.

MC and water were added thereto. An organic layer was separated, filtered, and vacuum evaporated, and then subjected to column chromatography (HX:EA=1:1)

Orange Solid 98%

2→3 (2-(dimethylamino)-N-(8-methoxy-1,4-dioxo-1,4-dihydronaphthalen-2-yl)acetamide)

16 ml of THF was added to 0.7 g of 2-chloro-N-(8-methoxy-1,4-dioxo-1,4-dihydronaphthalen-2-yl)acetamide (2.50 mmol) and stirred at room temperature. 0.16 g of tetrabutylammonium bromide (TBAB) (0.5 mmol), 0.21 g of KI (1.25 mmol), 1.4 ml of triethylamine (10 mmol), and 0.41 g of dimethylamine hydrochloride (5.0 mmol) were added thereto, followed by stirring for 3 hours at 70° C. MC and water were added thereto. The organic layer was separated, treated with MgSO4, filtered, and vacuum evaporated, and then subjected to column chromatography (DCM:CH3OH=20:1)

Yellow Solid 55%

3→4 (2-((dimethylamino)methyl)-9-methoxynaphtho[2,1-d]oxazol-5-ol)

0.15 g of 2-(dimethylamino)-N-(8-methoxy-1,4-dioxo-1,4-dihydronaphthalen-2-yl)acetamide (0.52 mmol) was dissolved in 4 ml of acetic acid and then stirred at room temperature. HBr (33 wt % in acetic acid) and 0.1 g of zinc dust (1.56 mmol) were added thereto, followed by stirring for 16 hours at 100° C. Neutralization was performed by adding aq. NaHCO3 and then extraction was performed using EA. The organic layer was separated, treated with MgSO4, filtered, and vacuum evaporated, and then subjected to column chromatography. (DCM:CH3OH=10:1).

Ivory Solid 42%

4→5 (2-((dimethylamino)methyl)-9-methoxynaphtho[2,1-d]oxazole-4,5-dione)

0.06 g of 2-((dimethylamino)methyl)-9-methoxynaphtho[2,1-d]oxazol-5-ol (0.22 mmol) was dissolved in 4.4 ml of DMF and then stirred at room temperature. IBX (47 wt %) was added thereto, followed by stirring for 1 hour at room temperature. Aq. NaHCO3 and EA were added thereto. Subsequently, an organic layer was separated, treated with MgSO4, filtered, and vacuum evaporated, and then separated through prep TLC. (DCM:CH3OH=10:1)

Orange Solid $^1$H NMR (300 MHz, CDCl$_3$) δ 7.80 (d, J=7.0 Hz, 1H), 7.51 (t, J=8.1 Hz, 1H), 7.28-7.26 (m, 1H), 4.03 (s, 3H), 3.84 (s, 2H), 2.45 (s, 6H)

Example 12. [Synthesis of Compound 12]

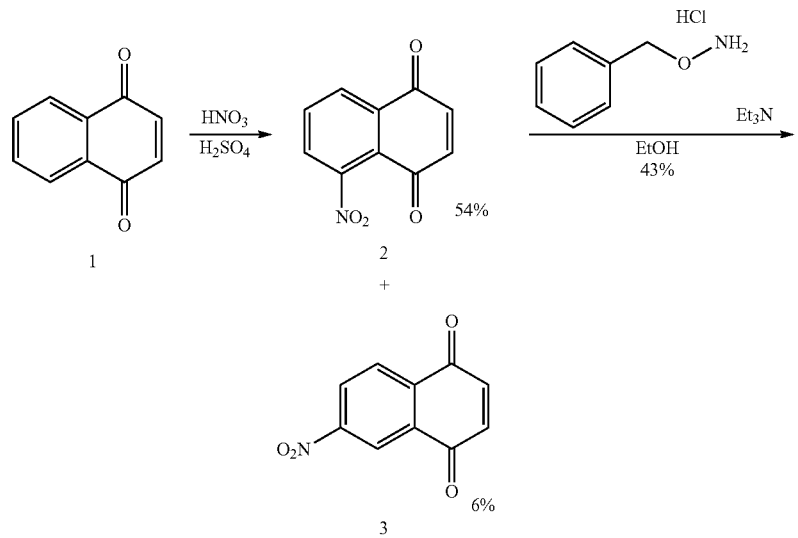

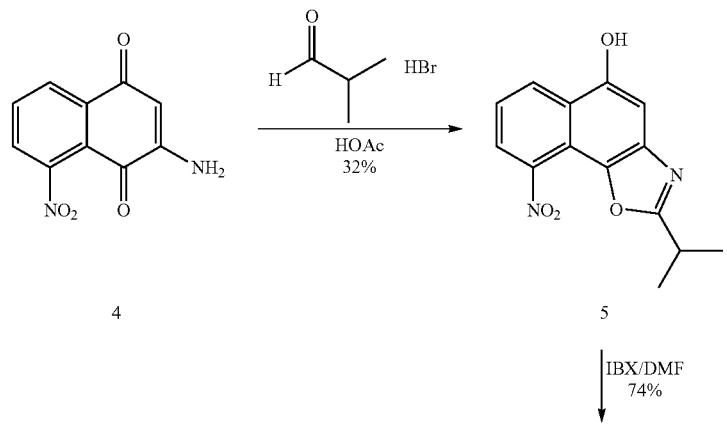

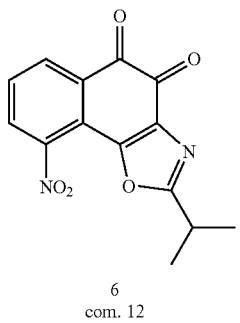

6
com. 12

1→2 (5-nitronaphthalene-1,4-dione)

25 ml of sulfuric acid was added to 1,4-naphthoquinone 2 g (12.65 mmol) and stirred in an ice bath. 7 g of sodium nitrate (82.2 mmol) was dissolved in 8 ml of sulfuric acid, and a reaction product solution was added to a reaction solution and stirred at room temperature for 2 hours. Ice was added to a reaction container and a yellow solid was filtered out.

The solid was dissolved in MC and then neutralized using aq. NaHCO$_3$. The organic layer was separated, treated with MgSO$_4$, filtered, and vacuum evaporated, and then separated through column chromatography. (HX:EA=3:1)

Compound 2→4%+Compound 3 6%

2→4 (2-amino-8-nitronaphthalene-1,4-dione)

0.3 g of o-benzylhydroxylamine hydrochloride (1.88 mmol) was dissolved in 6.5 ml of ethanol and then stirred in an ice bath. 0.27 ml of triethylamine (1.88 mmol) and 0.46 g of 5-nitronaphthalene-1,4-dione (2.26 mmol) were added thereto, followed by stirring for 9.5 hours at room temperature. Without workup, separation was performed through column chromatography. (HX:EA=1:1)

Orange Solid 43%

4→5 (2-isopropyl-9-nitronaphtho[2,1-d]oxazol-5-ol)

0.5 g of 2-amino-8-nitronaphthalene-1,4-dione (2.3 mmol) was dissolved in 7.6 ml of acetic acid and stirred at room temperature. 0.4 ml of HBr (33 wt % in acetic acid) and 1.05 ml of isobutyraldehyde (11.46 mmol) were added thereto, followed by stirring for 23 hours at room temperature. Neutralization was performed using aq. NaHCO$_3$ and then extraction was performed using EA. The organic layer was separated, treated with MgSO4, filtered, and vacuum evaporated, and then separated through column chromatography. (HX:EA=3:1)

Light Orange Solid 12%

5→6 (2-isopropyl-9-nitronaphtho[2,1-d]oxazole-4,5-dione)

20 mg of 2-isopropyl-9-nitronaphtho[2,1-d]oxazol-5-ol (0.075 mmol) was dissolved in 1.5 ml of DMF and stirred at room temperature. 54 mg of IBX (47 wt %) (0.09 mmol) was added thereto at room temperature and stirred for 2.5 hours. Aq. NaHCO$_3$ and EA were added thereto. Subsequently, an organic layer was separated, treated with MgSO$_4$, filtered, and vacuum evaporated, and then separated through prep TLC. (HX:EA=2:1)

Deep Yellow Solid 76%

$^1$H NMR (300 MHz, acetone-d$_6$) δ 8.33 (dd, J=1.1 Hz, 8.1 Hz, 1H), 8.14 (dd, J=1.1 Hz, 8.1 Hz, 1H), 7.88 (t, J=8.1 Hz, 1H), 3.30-3.21 (m, 1H), 1.40 (s, 1H), 1.38 (s, 1H)

Example 13. [Synthesis of Compound 13]

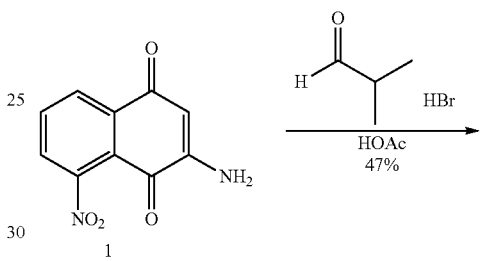

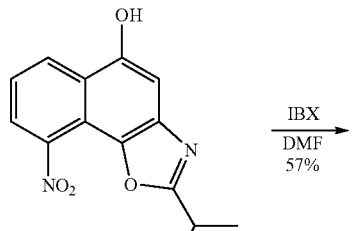

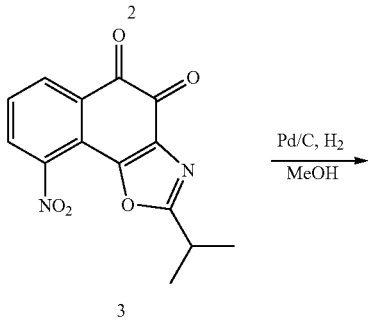

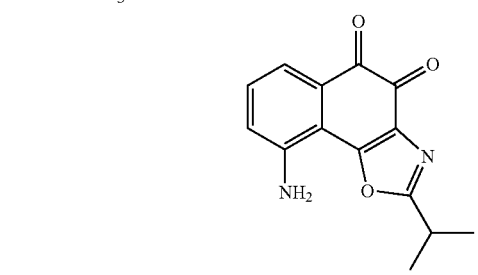

4
com. 13

Example 14. [Synthesis of Compound 14]

synthesis of 2-isopropyl-9-methyloxazolo[5,4-f]quinoline-4,5,7(6H)-trione

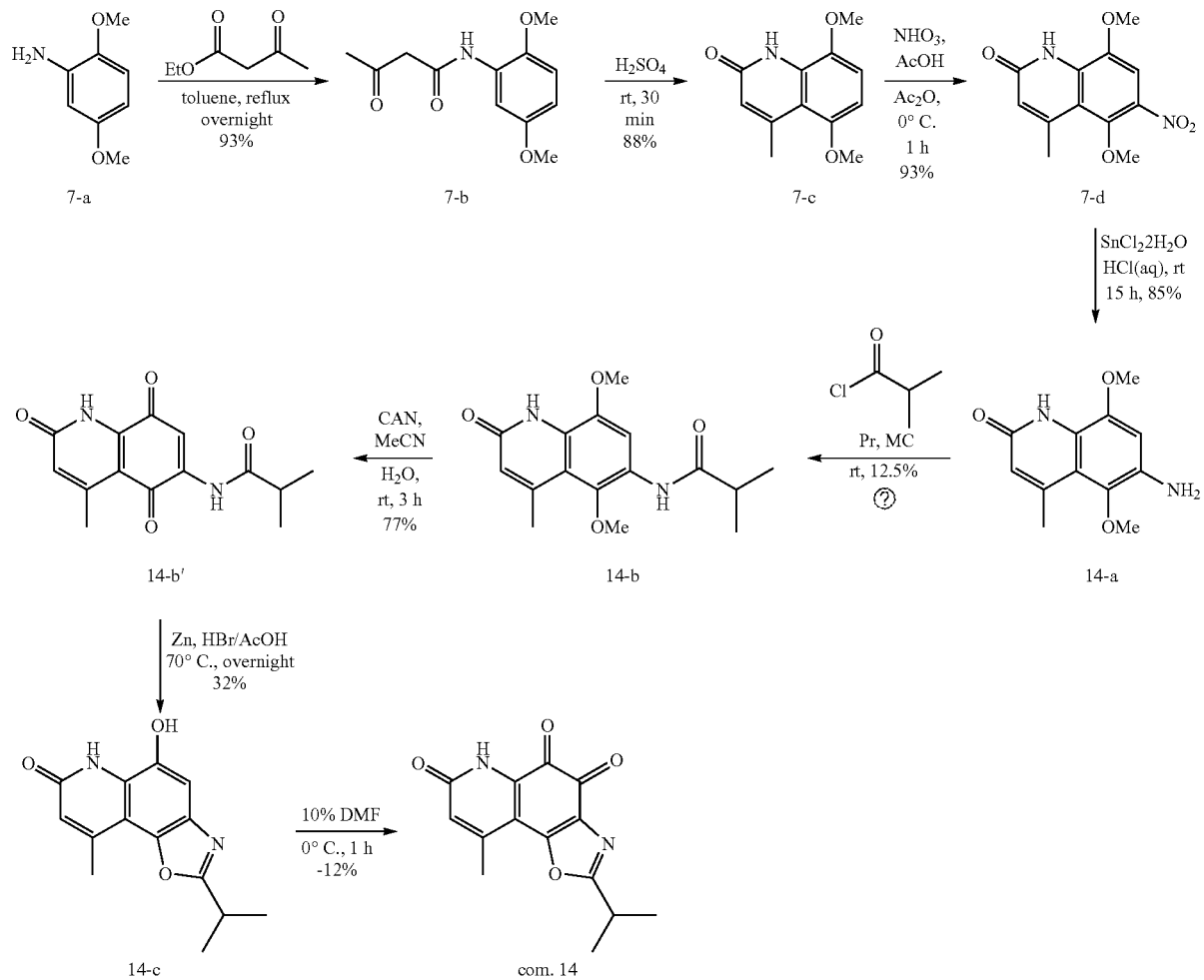

1. Compound a

Compound 7-d (2.05 g, 7.77 mmol) was added to a 35% aqueous hydrochloric acid solution (39 ml), and then SnCl$_2$ 2H$_2$O (8.8 g, 38.83 mmol) was added thereto, followed by stirring for 15 hours at room temperature. A reaction solution was basified using saturated aqueous NaHCO$_3$ and then extracted using MC. The separated organic layer was dried over MgSO$_4$ and then filtered. The filtrate was vacuum evaporated and then recrystallized in EA and HX.

Yield: 85%

1H NMR (300 MHz, CDCl$_3$): 2.66 (3H, s), 3.73 (3H, s), 3.89 (3H, s), 6.44 (1H, s), 6.53 (1H, s), 8.94 (1H, brs)

2. Compound 14-b

Compound 14-a (0.7 g, 2.99 mmol) was dissolved in MC (30 ml), and then pyridine (0.4 ml, 4.48 mmol) and isobutyryl chloride (0.5 ml, 4.48 mmol) were added thereto, followed by stirring for 12.5 hours at room temperature. NaOMe (0.5 M in MeOH, 6 ml) was added to a reaction solution and stirred for one hour. Distilled water was added thereto. Subsequently, an organic layer was washed with 2 M HCl and saturated aqueous NaHCO$_3$, and then dried over MgSO$_4$ and filtered. The filtrate was vacuum evaporated and then recrystallized in EA and HX.

Yield: 88%

1H NMR (300 MHz, CDCl$_3$): 1.32 (6H, d, J=7.0 Hz), 2.59-2.66 (4H, singlet+septet, septet J=7.0 Hz), 3.73 (3H, s), 3.97 (3H, s), 6.49 (1H, s), 7.78 (1H, s), 8.18 (1H, s), 9.33 (1H, brs)

3. Compound 14-b'

Compound 14-b (0.7 g, 2.30 mmol) was dissolved in a mixture of acetonitrile (17.5 ml) and distilled water (7 ml) and then ceric ammonium nitrate (3.8 g, 6.90 mmol) was added thereto. A reaction solution was stirred for 3 hours at room temperature and then acetonitrile was vacuum evaporated. Subsequently, distilled water was added thereto and extraction was performed using MC. An organic layer was separated, dried over MgSO$_4$, and filtered. The filtrate was vacuum evaporated and then recrystallized using MC and HX.

Yield: 77%

1H NMR (300 MHz, CDCl$_3$): 1.28 (6H, d, J=7.0 Hz), 2.59 (3H, s), 2.68 (1H, septet, J=7.0 Hz), 6.58 (1H, s), 7.74 (1H, s), 8.57 (1H, brs), 9.82 (1H, brs)

4. Compound 14-c

Compound 14-b' (10 mg, 36.45 μmol) was mixed with acetic acid (120 microliters), and then HBr/AcOH (33%, 33 microliters, 0.18 mmol) and Zn (7 mg, 0.11 mmol) were added thereto, followed by stirring for one day at 70° C. Temperature was lowered to room temperature, and then MC was added thereto and neutralization was performed using saturated aqueous NaHCO$_3$. An organic layer was dried over MgSO$_4$ and filtered. The filtrate was vacuum evaporated and then purified through column chromatography (EA, HX).

Yield: 32%

1H NMR (300 MHz, MeOH-d$^4$): 1.47 (6H, d, J=7.0 Hz), 2.15 (3H, s), 3.30 (1H, septet, J=7.0 Hz), 6.57 (1H, s), 7.20 (1H, s)

5. Compound 14

Compound 14-c (10 mg, 38.72 μmol) was dissolved in DMF (0.8 ml), and then IBX (27 mg, 42.59 μmol) were added thereto, followed by stirring at 0° C. After one hour, MC was added thereto and an organic layer was washed with saturated aqueous NaHCO$_3$, and then dried over MgSO$_4$ and then filtered. The filtrate was vacuum evaporated and separated through prep-TLC.

Yield: ~19%

1H NMR (300 MHz, CDCl$_3$): δ 6.78 (s, 1H), 3.22 (septet, J=6.6 Hz, 1H), 2.58 (s, 3H), 1.45 (d, J=6.6 Hz, 6H)

Example 15. [Synthesis of Compound 15]

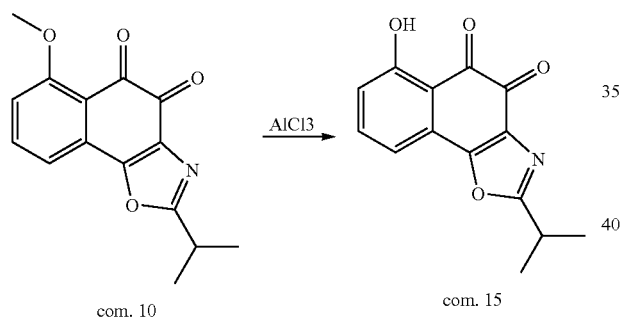

com. 10          com. 15

35 mg of 2-isopropyl-6-methoxynaphtho[2,1-d]oxazole-4,5-dione was dissolved in 1 ml of dichloromethane (0.1 M) and then AlCl$_3$ was added thereto at 0° C. Stirring was performed for 2 hours at 40° C. When the reaction was completed, aq. NaHCO$_3$ was added thereto and extraction was performed using MC several times. An MC layer was treated with MgSO$_4$, filtered, and vacuum concentrated, and then separated through prep TLC (Hex:EA=1:1)

Reddish Brown Solid: 3 mg (9%)

1H NMR (300 MHz, CDCl$_3$) δ 12.02 (s, 1H), 7.59 (t, J=7.2 Hz, 1H), 7.25 (d, J=7.8 Hz, 1H), 7.10 (d, J=9.6 Hz, 1H), 3.23 (m, 1H), 1.46 (d, J=6.9 Hz, 6H) or

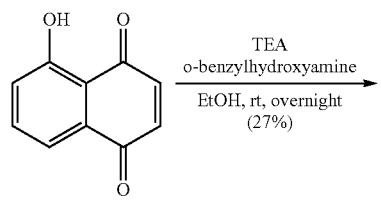

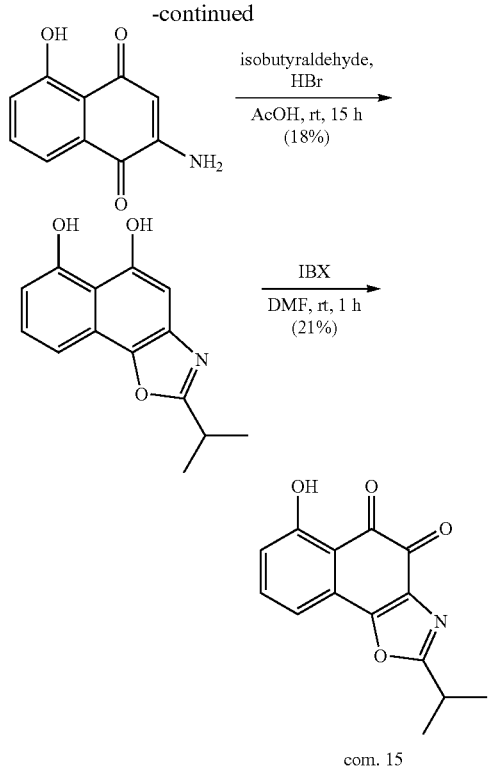

com. 15

Step 1: preparation of 2-amino-5-hydroxynaphthalene-1,4-dione 764 mg of o-benzylhydroxyamine hydrochloride was added to MeOH (8 ml) and 0.67 ml of Et3N was added thereto at 0° C. 8 ml of EtOH, to which 1 g of 5-hydroxynaphthalene-1,4-dione (1.2 eq.) was added, was added dropwise thereto and then stirred for 15 hours at room temperature. Extraction was performed using aq. NaHCO$_3$ and MC. The extract was treated with MgSO$_4$, filtered, and evaporated, and then subjected to column chromatography (H:EA:MC=4:1:1)

Solid: 280 mg (27%)

$^1$H NMR (300 MHz, CDCl$_3$) δ 12.83 (s, 1H), 7.60 (d, J=7.2 Hz, 1H), 7.49 (t, J=7.8 Hz, 1H), 7.38-7.32 (m, 2H), 5.41 (brs, 2H)

Step 2: 2-isopropylnaphtho[2,1-d]oxazole-5,6-diol 1.8 ml of AcOH was added to 100 mg of 2-amino-5-hydroxynaphthalene-1,4-dione (1 eq.), and then 0.25 ml of 33% HBr in AcOH and 0.24 ml of isobutyraldehyde (5 eq.) were sequentially added thereto at room temperature. The reaction product was stirred for 3 hours at room temperature. When the reaction was completed, neutralization was performed using aq. NaHCO$_3$ and then extraction was performed using MC. Treatment with MgSO4, filtration, and evaporation, and then separation through prep TLC were performed. (MC:MeOH=30:1)

Solid: 20 mg (16%)

Step 3: 6-hydroxy-2-isopropylnaphtho[2,1-d]oxazole-4,5-dione 0.4 ml of DMF was added to 12 mg of 2-isopropylnaphtho[2,1-d]oxazole-5,6-diol and 36 mg of IBX (1.2 eq.) having a purity of 47% was added thereto while stirring at room temperature. The reaction product was stirred for one hour at room temperature. When the reaction was completed, an excess of EA was added thereto and washing was performed with aq. NaHCO₃ approximately twice to maximally remove DMF. Treatment with MgSO₄, filtration, and evaporation were performed. Subsequently, filtration was performed when recrystallized and washing was performed using MC.

Orange Solid: 2.6 mg (21%)

Examples 16 and 17. [Synthesis of Compounds 16 and 17]

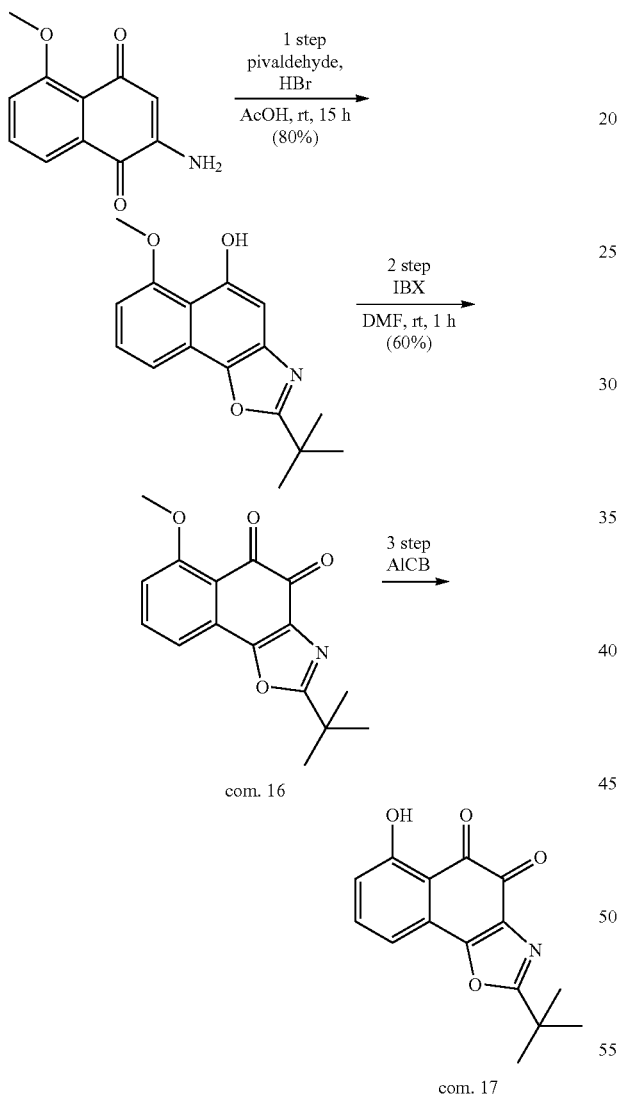

com. 16 com. 17

Step 1: 2-tert-butyl-6-methoxynaphtho[2,1-d]oxazol-5-ol

AcOH 4.2 ml was added to 250 mg of 2-amino-5-methoxynaphthalene-1,4-dione (1 eq.) and 0.21 ml of 33% HBr in AcOH and 0.67 ml of pivaldehyde (5 eq.) were sequentially added thereto at room temperature. The reaction product was stirred for 15 hours at room temperature. When the reaction was completed, neutralization was performed using aq. NaHCO₃ and then extraction was performed using MC. An MC layer was treated with MgSO₄, filtered, and evaporated, and then subjected to column chromatography (Hex:EA=4-2:1)

Oil: 300 mg (90%)

Step 3: 2-tert-butyl-6-methoxynaphtho[2,1-d]oxazole-4,5-dione (Compound 16)

13 ml of DMF was added to 2-tert-butyl-6-methoxynaphtho[2,1-d]oxazol-5-ol 300 mg and 790 mg of IBX (1.2 eq.) having a purity of 47% was added thereto while stirring at room temperature. The reaction product was stirred for one hour at room temperature. An excess amount of EA was added thereto when the reaction was completed and washing was performed using aq. NaHCO₃ approximately twice to maximally remove DMF. Treatment with MgSO₄, filtration, and evaporation were performed. Subsequently, filtration was performed when recrystallized and washing was performed using MC.

Orange Solid: 189 mg (60%)

1H NMR (300 MHz, CDCl₃) δ 7.64 (t, J=8.4 Hz, 1H), 7.34 (d, J=7.2 Hz, 1H), 7.13 (d, J=8.7 Hz, 1H), 4.02 (s, 3H), 1.49 (s, 9H)

Step 4: 2-tert-butyl-6-hydroxynaphtho[2,1-d]oxazole-4,5-dione (Compound 17)

(A yield was 5% under a condition of AlCl₃/CH₂Cl₂ but a yield was 30% when an experiment was performed using BBr₃)

2-tert-butyl-6-methoxynaphtho[2,1-d]oxazole-4,5-dione 40 mg was added to a dried 25 ml flask, and then 1.5 ml of dry MC was added thereto, followed by stirring at 0° C. 1 M BBr₃ in Dichloromethane 0.42 ml (3 eq.) was added dropwise thereto at 0° C. and then stirred for 1.5 hours at room temperature. When the reaction was completed, quenching was performed by adding ice thereto in an ice bath. Subsequently, neutralization was performed using aq. NaHCO₃ and extraction was performed using MC. The extract was treated with MgSO₄, filtered, and evaporated, and then subjected to column chromatography (MC:MeOH=30:1). Recrystallization was performed using EA:Hex again and then filtration was performed.

Orange Solid: 12 mg (30%)

¹H NMR (300 MHz, CDCl₃) δ 12.02 (s, 1H), 7.59 (t, J=7.5 Hz, 1H), 7.28-7.25 (m, 1H), 7.09 (d, J=8.7 Hz, 1H), 1.49 (s, 9H)

Examples 18 and 19. [Synthesis of Compounds 18 and 19]

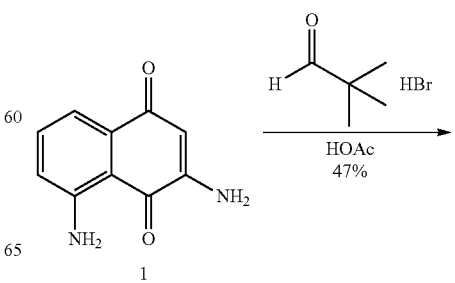

1

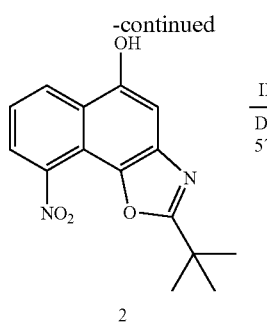

2

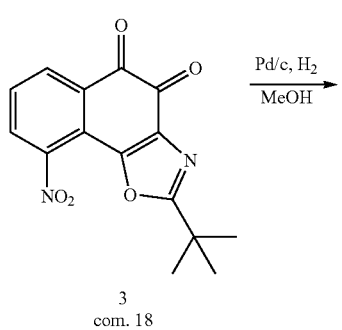

3
com. 18

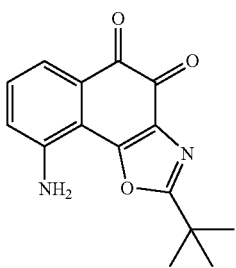

4
com. 19

1→2

A synthesis method thereof was the same as that of Compound 12.
0.13 g of Compound 1 (0.60 mmol)
0.32 ml of pivaldehyde (2.98 mmol)
ml of HBr (33 wt % in acetic acid)
ml of acetic acid
Stirring was performed for 17 hours at room temperature.
Deep yellow solid 47%

2→3 (Compound 18)

77 mg of Compound 2 (0.27 mmol) was dissolved in 1.5 ml of DMF and stirred at room temperature
190 mg of IBX (47 wt %) (0.32 mmol) was added thereto
Stirring was performed at room temperature (1 h)
Workup (EA:H$_2$O) (NaHCO$_3$ (aq))
A solvent was evaporated and filtration was performed through silica gel (washing with CH$_2$Cl$_2$)
Recrystallization (HX:EA)
Deep Yellow Solid 57%
$^1$H NMR (300 MHz, acetone-d$_6$) δ 8.33 (dd, J=1.1 Hz, 7.9 Hz, 1H), 8.15 (dd, J=1.1 Hz, 7.9 Hz, 1H), 7.88 (t, J=7.9 Hz, 1H), 1.43 (s, 9H)

3→4 (Compound 19)

Compound 3 was dissolved in MeOH, and then 5% Pd/C was added thereto, the reaction vessel was filled with hydrogen, and stirring was performed for six hours at room temperature. Filtration was performed through Celite to remove Pd, and a filtrate was concentrated and then recrystallization was performed using EA/Hex.
1H NMR (300 MHz, CDCl$_3$): 7.41 (dd, J=1.5, 7.3 Hz, 1H), 7.32 (t, J=7.3 Hz, 1H), 7.18 (m, 1H), 3.29 (septet, J=7.0 Hz, 1H), 1.43 (d, J=7.0 Hz, 6H)

Example 20. [[Synthesis of Compound 20] Synthesis of 2-isopropyloxazolo[5,4-f]quinoline-4,5-dione (Compound 20)]

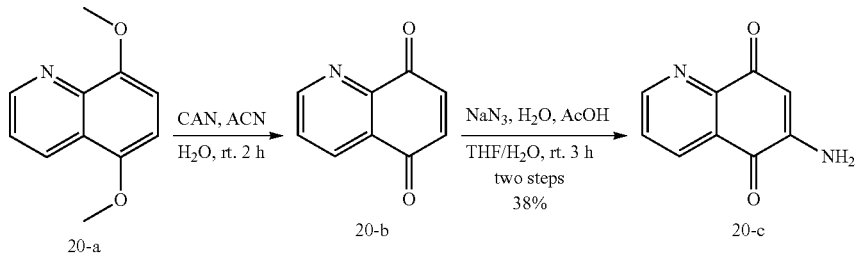

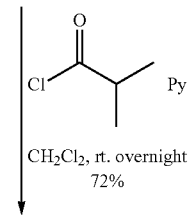

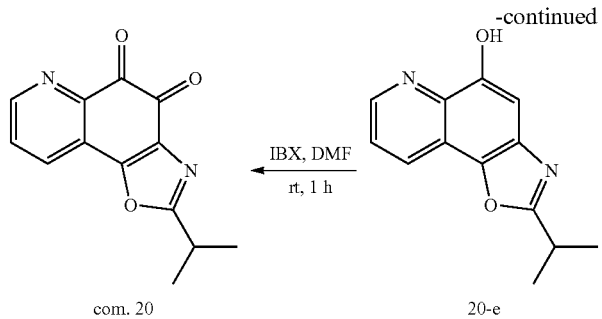
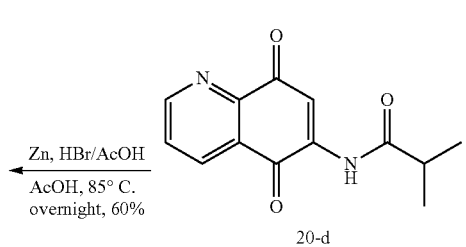

Compound 20-b

Compound 20-a (5,8-dimethoxyquinoline, 1.0 g, 5.29 mmol) was dissolved in acetonitrile (25 ml) and distilled water (10 ml), and then ceric ammonium nitrate (8.7 g, 15.86 mmol) was added thereto. A reaction solution was stirred for 2 hours at room temperature and then acetonitrile was vacuum evaporated. MC was added thereto and washing was performed using saturated aqueous $NaHCO_3$. Subsequently, drying was performed using $MgSO_4$ and then filtration was performed. The filtrate was vacuum evaporated and then used in the next reaction.

1H NMR (300 MHz, $CDCl_3$): 7.09 (1H, d, J=10.6 Hz), 7.18 (1H, d, J=10.6 Hz), 7.73 (1H, dd, J=4.7, 8.0 Hz), 8.44 (1H, dd, J=1.8, 8.0 Hz), 9.07 (1H, dd, J=1.8, 4.7 Hz)

Compound 20-c $NaN_3$ (1.13 g, 17.44 mmol) was dissolved in water (2.6 ml) and then acetic acid (0.9 ml) was added thereto. A solution of $NaN_3$ was added to a THF/$H_2O$ solution (10.5 ml, 3.5 ml), in which Compound 20-b (all crude products from previous reaction) was dissolved, and heated to 50° C. 3 hours later, THF was vacuum evaporated and MC was added thereto. An organic layer was basified using saturated aqueous $NaHCO_3$ and then separated and dried over $MgSO_4$. Subsequently, filtration was performed. The filtrate was vacuum evaporated and then purified through column chromatography and recrystallization.

Yield of Steps 1+2: 38%

1H NMR (300 MHz, MeOH-$d^4$): 6.06 (1H, s), 7.69-7.73 (1H, m), 8.42 (1H, d, J=6.2 Hz), 8.89 (1H, m)

Compound 20-d

Compound 20-c (0.1 g, 0.57 mmol) was dissolved in MC (6 ml), and then pyridine (0.23 ml, 2.87 mmol) and isobutyryl chloride (0.18 ml, 1.72 mmol) were added thereto, followed by stirring for one day at room temperature. Saturated aqueous $NaHCO_3$ was added to a reaction solution and extraction was performed using MC. An organic layer was separated, dried with $MgSO_4$, and filtered. The filtrate was vacuum evaporated and then recrystallized.

Yield: 72%

1H NMR (300 MHz, $CDCl_3$): 1.29 (6H, d, J=6.6 Hz), 2.68 (1H, septet, J=6.6 Hz), 7.68 (1H, dd, J=4.7, 8.0 Hz), 8.07 (1H, s), 8.34 (1H, brs), 8.45 (1H, d, J=8.0 Hz), 9.08 (1H, d, J=4.7 Hz)

Compound 20-e

Compound 20-d (50 mg, 0.20 mmol) was mixed with acetic acid (1 ml), and then HBr/AcOH (33%, 111 microliters, 0.61 mmol) and Zn (40 mg, 0.61 mmol) were added thereto, followed by stirring overnight at 70° C. Temperature was lowered to room temperature, and then MC was added thereto and neutralization was performed using saturated aqueous $NaHCO_3$. An organic layer was dried over $MgSO_4$ and filtered. The filtrate was vacuum evaporated and purified through column chromatography (MC, MeOH).

Yield: 60%

1H NMR (300 MHz, $CDCl_3$): 1.52 (6H, d, J=7.0 Hz), 3.34 (1H, septet, J=7.0 Hz), 7.47 (1H, s), 7.55-7.59 (1H, m), 8.29 (1H, brs), 8.49 (1H, d, J=8.4 Hz), 8.79-8.80 (1H, m)

Compound 20

Compound 20-e (28 mg, 0.12 mmol) was dissolved in DMF (2.5 ml), and then IBX (84 mg, 0.13 mmol) was added thereto, followed by stirring at room temperature. After one hour, distilled water was added thereto, extraction was performed using MC, and separation was performed. Subsequently, drying was performed and then filtration was performed. The filtrate was vacuum evaporated and then separated through prep-TLC.

1H NMR (300 MHz, $CDCl_3$): 1.48 (6H, d, J=7.0 Hz), 3.27 (1H, septet, J=7.0 Hz), 7.62-7.66 (1H, m), 8.08-8.11 (1H, m), 8.84-8.86 (1H, m)

Examples 21, 22, and 23. [Synthesis of Compounds 20, 21, and 22]

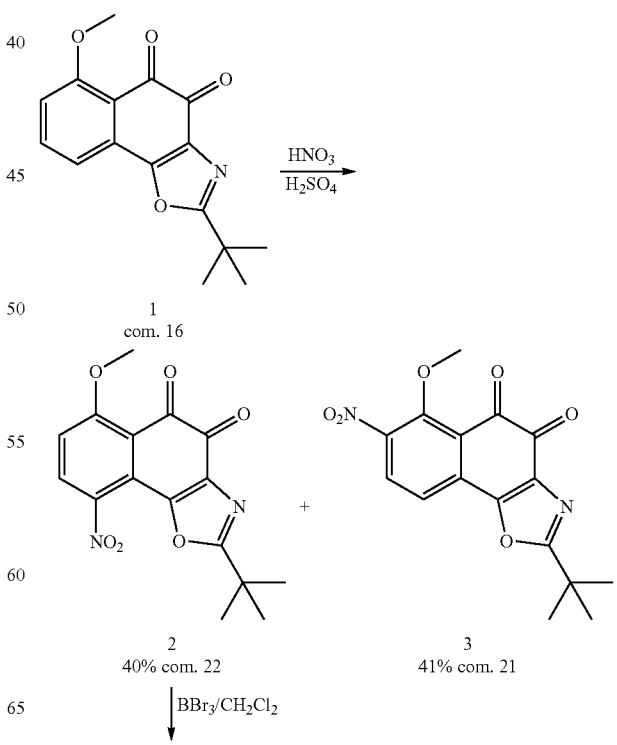

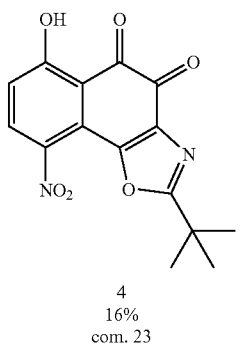

4
16%
com. 23

1→2+3

While stirring 0.35 ml of sulfuric acid in an ice bath, 50 mg of Compound 16 (0.18 mmol) was added thereto, and then 0.016 ml of nitric acid (60%) (0.21 mmol) was slowly added thereto, followed by stirring for one hour at room temperature. Neutralization was performed using aq. NaHCO₃, extraction was performed using EA, and treatment with MgSO₄, filtration, and evaporation were performed. Subsequently, a reaction product was subjected to column chromatography. (HX:EA=1:1).

Light Yellow Solid, Compound 2 (Compound 22) 40%+
Light Orange Solid, Compound 3 (Compound 21) 41%

2-tert-butyl-6-methoxy-7-nitronaphtho[2,1-d]oxazole-4,5-dione

¹H NMR (300 MHz, CDCl₃) δ 8.05 (d, J=8.4 Hz, 1H), 7.62 (d, J=8.4 Hz), 4.08 (s, 3H), 1.51 (s, 9H)

2 (2-tert-butyl-6-methoxy-9-nitronaphtho[2,1-d]oxazole-4,5-dione)

¹H NMR (300 MHz, CDCl₃) δ 7.83 (d, J=9.3 Hz, 1H), 7.19 (d, J=9.3 Hz, 1H), 4.09 (s, 3H), 1.45 (s, 9H)

2→4 (2-tert-butyl-6-hydroxy-9-nitronaphtho[2,1-d]oxazole-4,5-dione)

10 mg of 2-tert-butyl-6-methoxy-9-nitronaphtho[2,1-d]oxazole-4,5-dione (Compound 22) (0.03 mmol) dissolved in CH₂Cl₂ was added to 0.1 ml of BBr₃ (1 M CH₂Cl₂ solution) (0.091 mmol) stirred in an ice bath and neutralized using aq. NaHCO₃ stirred for one hour at room temperature. Subsequently, an organic layer extracted using MC was treated with MgSO₄, filtered through silica gel, and evaporated. Subsequently, separation through prep TLC was performed.

Red Solid 16%

¹H NMR (300 MHz, CDCl₃) δ 12.48 (br, s, 1H), 7.8 (d, J=8.6 Hz, 1H), 7.2 (d, J=8.6 Hz, 1H), 1.46 (s, 9H)

Example 24. [Synthesis of Compound 24]

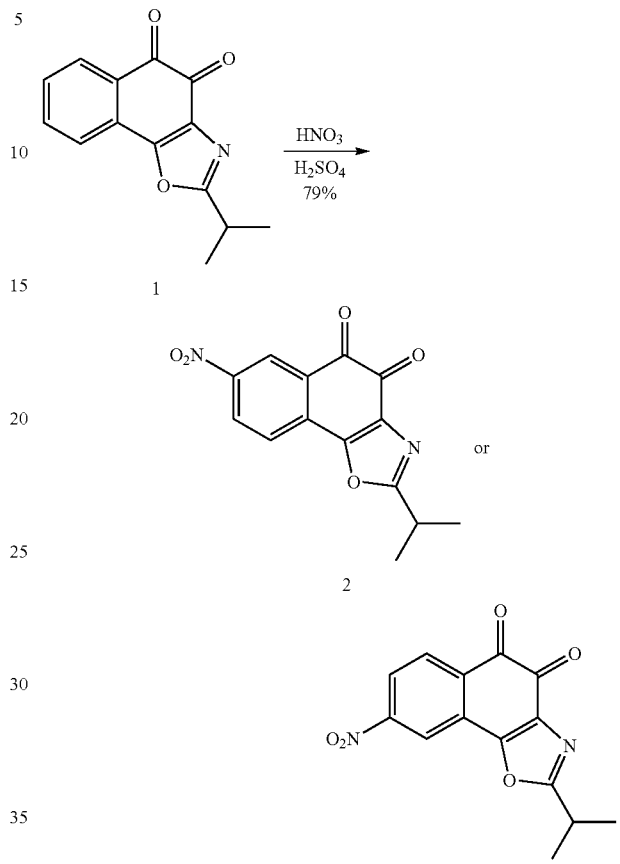

1→2 or 3

0.83 ml of sulfuric acid was added to 0.1 g of Compound 1 (0.42 mmol) while stirring in an ice bath, and then neutralized using aq. NaHCO₃ to which 0.04 ml of nitric acid (60%) (0.5 mmol) was slowly added and which was stirred for 3.5 hours at room temperature. Subsequently, an organic layer extracted using EA was treated with MgSO₄, filtered, and evaporated, and then recrystallized in Hex/EA.

Yellow solid Compound 2 or 3 (Compound 24) 79%

¹H NMR (300 MHz, CDCl₃) δ 8.94 (d, J=2.2 Hz, 1H), 8.57 (dd, J=2.2 Hz, 8.4 Hz, 1H), 7.93 (d, J=8.4 Hz, 1H), 3.34-3.25 (m, 1H), 1.51 (s, 3H), 1.48 (s, 3H)

Example 25. [Synthesis of Compound 25]

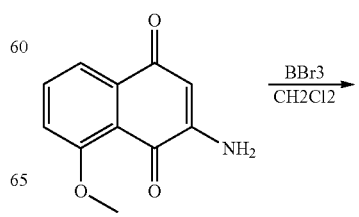

-continued

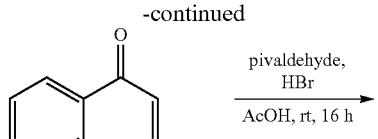

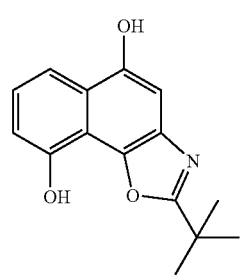

com. 25

Step 1: 2-amino-8-hydroxynaphthalene-1,4-dione 285 mg of 2-amino-8-methoxynaphthalene-1,4-dione was dissolved in 15 ml of MC, and then 2.83 ml of BBr$_3$ was added thereto at 0° C. and stirred for 30 minutes at room temperature. When the reaction was completed, the reaction product was quenched by adding ice, and then neutralization was performed using aq. NaHCO$_3$ and extraction was performed using MC. Treatment with MgSO$_4$, filtration, and evaporation were performed. Subsequently, a reaction product was subjected to column chromatography. (Hex:EA=3:1)

Orange Solid: 78 mg (29%)

$^1$H NMR (300 MHz, CDCl$_3$) δ 11.55 (s, 1H), 7.86 (d, J=7.8 Hz, 1H), 7.68 (t, J=8.4 Hz, 1H), 7.62-7.60 (m, 1H), 5.96 (s, 1H), 5.30 (brs, 2H)

Final step: 2-tert-butyl-9-hydroxynaphtho[2,1-d]oxazole-4,5-dione (Compound 25)

An experimental method thereof was the same as those of Compounds 10 and 16.

1H NMR (300 MHz, CDCl$_3$) δ 12.12 (s, 1H), 7.77 (d, J=7.2 Hz, 1H), 7.65 (t, J=8.1 Hz, 1H), 7.32 (d, J=8.4 Hz, 1H), 1.52 (s, 9H)

Example 26. [Synthesis of Compound 26]

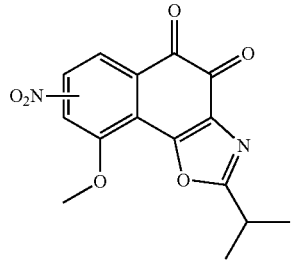

While stirring 0.83 ml of sulfuric acid in an ice bath, 0.1 g of Compound 8 (0.42 mmol) was added thereto and then neutralized using aq. NaHCO$_3$ to which 0.04 ml of nitric acid (60%) (0.5 mmol) was slowly added and stirred for 3.5 hours at room temperature. Subsequently, an organic layer extracted using EA was treated with MgSO$_4$, filtered, and evaporated. Subsequently, recrystallization thereof was performed using Hex/EA.

Examples 27 to 32. [Synthesis of Compounds 27 to 32]

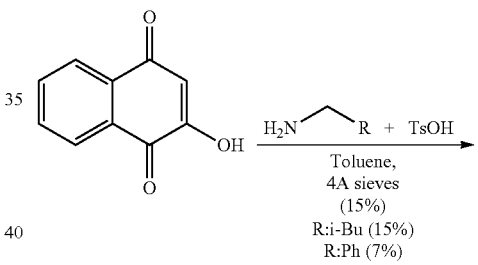

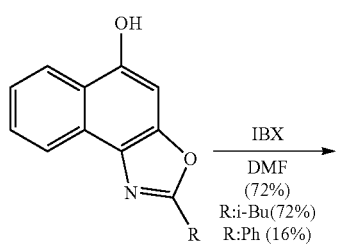

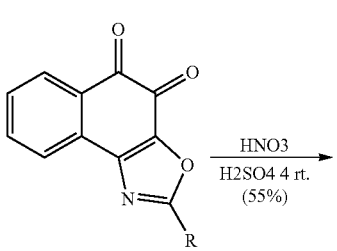

R:i-Bu(com. 28)
R:Ph (com. 27)

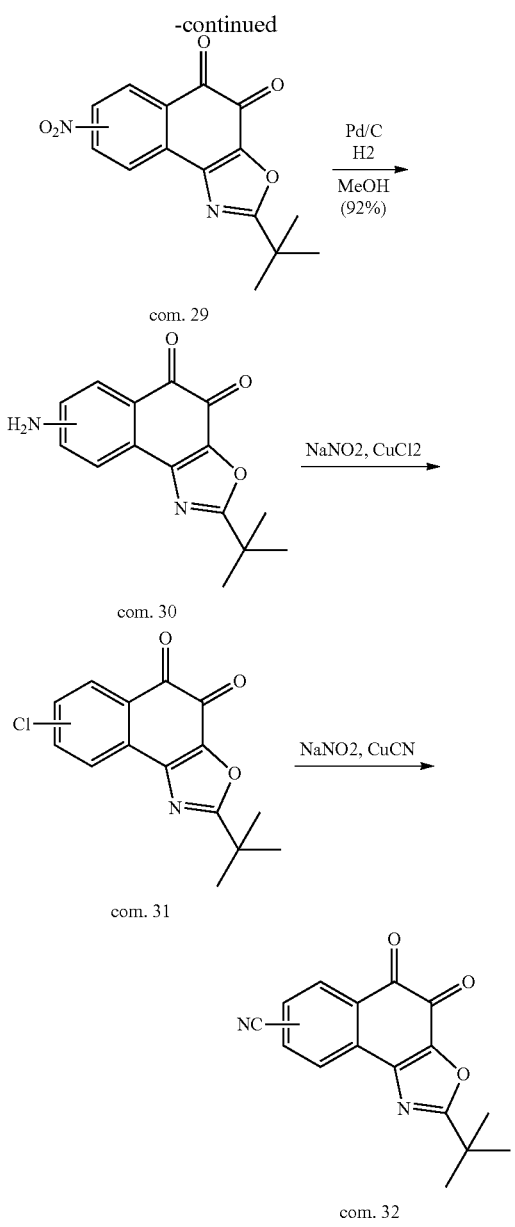

com. 29 com. 30 com. 31 com. 32

Step 1: preparation of
2-tert-butylnaphtho[1,2-d]oxazol-5-ol 200 ml of toluene was added to 5 g of 2-hydroxynaphthalene-1,4-dione, and then 40 g of 4-Angstrom molecular sieves, 3.5 ml of neophenthylamine (1.05 eq.), and 545 mg of TsOH (0.1 eq.) were sequentially added thereto and reacted for 3 hours at 120° C. The reaction product was cooled, and then filtered and washed with toluene. Since a product is filtered with molecular sieves at the upper portion, the reaction product was dissolved using MC and MeOH, and then a filtrate was vacuum evaporated. Subsequently, the filtrate was recrystallized using MC:Hex and then filtered.

Violet Solid: 1.067 g (15%)

Step 2: preparation of 2-tert-butylnaphtho[1,2-d]
oxazole-4,5-dione 1.054 g of 2-tert-butylnaphtho[1,2-d]oxazol-5-ol was dissolved in 44 ml of DMF and then 3.1 g of IBX (1.2 eq.) was added thereto portionwise. The reaction product was stirred for 40 minutes at room temperature, thereby completing reaction. 300 ml of EA was added to the reaction product and then washing with 150 ml of aq. $NaHCO_3$ was performed approximately five times, thereby obtaining 750 ml of an aqueous layer. Subsequently, approximately 100 ml of EA was added to the aqueous layer, thereby extracting a product. The EA layer including the product was treated with $MgSO_4$, filtered, and vacuum evaporated. Subsequently, separation through short-column chromatography was performed. (Hex:EA=2:1)

A part including the product was vacuum evaporated again and then purified through recrystallization in EA:Hex.

Yellow Solid: 801 mg (72%)

Step 3: 2-tert-butyl-7-nitronaphtho[1,2-d]oxazole-4,
5-dione (or 2-tert-butyl-8-nitronaphtho[1,2-d]oxazole-4,5-dione)

2.4 ml of $H_2SO_4$ (0.5M) was added to a flask and then stirred in an ice bath. 하에서 300 mg of 2-tert-butylnaphtho[1,2-d]oxazole-4,5-dione being a solid was added thereto and then 0.11 ml of 60% nitric acid (1.2 eq.) was added dropwise thereto. After stirring for 4 hours at room temperature, the reaction product was poured onto ice water and extracted using EA neutralized by adding $NaHCO_3$. Subsequently, treatment with $MgSO_4$ and filtration were performed and filtration was performed through recrystallization in EA:Hex vacuum evaporated.

Yellow Solid: 193 mg (55%)

1H NMR (300 MHz, $CDCl_3$) δ 8.91 (d, J=2.1 Hz, 1H), 8.55 (d, J=8.4 Hz, 1H), 8.21 (d, J=8.4 Hz, 1H), 1.53 (s, 9H)

Step 4: 7-amino-2-tert-butylnaphtho[1,2-d]oxazole-
4,5-dione (or 8-amino-2-tert-butylnaphtho[1,2-d]
oxazole-4,5-dione)

193 mg of 2-tert-butyl-7-nitronaphtho[1,2-d]oxazole-4,5-dione (or 2-tert-butyl-8-nitronaphtho[1,2-d]oxazole-4,5-dione) was dissolved in 6.4 ml of a mixture of MeOH (0.1 M) and MC 3 ml (0.2M), and then 30 mg of Pd/C was added thereto and shaken. Subsequently, vacuum was applied to the reaction vessel followed by filling with hydrogen. The reaction product was stirred for 12 hours or more at room temperature. When the reaction was completed, color of the reaction product was changed into violet. When filtration was performed through Celite, washing was performed with MeOH and vacuum evaporation was performed. Subsequently, a product was separated through short-column chromatography. (Hex:EA=1:1). The columned product was vacuum evaporated again and purified through recrystallization in EA:Hex.

Violet Solid: 160 mg (92%)

1H NMR (300 MHz, $CDCl_3$) δ 7.72 (d, J=7.8 Hz, 1H), 7.37 (d, J=2.1 Hz, 1H), 6.85 (d, J=8.4 Hz, 1H), 4.13 (brs, 2H), 1.48 (s, 9H)

Step 5: 2-tert-butyl-7-chloronaphtho[1,2-d]oxazole-
4,5-dione (or 2-tert-butyl-8-chloronaphtho[1,2-d]
oxazole-4,5-dione)

cHCl (0.5 ml) and $H_2O$ (0.5 ml) were added to a vial and cooled in an ice bath. Subsequently, 20 mg of 7-amino-2-tert-butylnaphtho[1,2-d]oxazole-4,5-dione (or 8-amino-2-tert-butylnaphtho[1,2-d]oxazole-4,5-dione) was added thereto, followed by stirring for 3 minutes. 6 mg of $NaNO_2$ (1.2 eq.) dissolved in 0.1 ml of $H_2O$ was added dropwise thereto. Subsequently, stirring was performed for 5 minutes. After confirming that a starting material had disappeared, 23 mg of CuCl₂ (1.8 eq.) was added thereto, followed by stirring for 20 minutes at 5 r (since there is a tendency that sprots are entirely tarnished as times passed, reaction must be rapidly terminated)

Orange Solid: 2 mg (9.5%)

1H NMR (300 MHz, CDCl₃) δ 8.07 (s, 1H), 7.93 (d, J=8.1 Hz, 1H), 7.66 (d, J=8.1 Hz, 1H), 1.50 (s, 9H)

Step 6: 2-tert-butyl-4,5-dioxo-4,5-dihydronaphtho[1,2-d]oxazole-7-carbonitrile (or 2-tert-butyl-4,5-dioxo-4,5-dihydronaphtho[1,2-d]oxazole-8-carbonitrile)

2 ml of 4.5N HCl was added to a vial and cooled in an ice bath. Subsequently, 40 mg of 7-amino-2-tert-butylnaphtho[1,2-d]oxazole-4,5-dione (or 8-amino-2-tert-butylnaphtho[1,2-d]oxazole-4,5-dione) was added thereto, followed by stirring for 10 minutes. 15 mg of NaNO₂ (1.2 eq.) dissolved in 0.2 ml of H₂O was added dropwise thereto and then stirred for 10 minutes. After confirming that a starting material had disappeared, 23 mg of CuCN (1.8 eq.) was added thereto, followed by stirring for 5 minutes at 5° C.

Orange Solid: 2.8 mg (6.7%)

1H NMR (300 MHz, CDCl₃) δ 8.36 (s, 1H), 8.14 (d, J=8.1 Hz, 1H), 7.98 (d, J=8.1 Hz, 1H), 1.51 (s, 9H)

1.8 mg of 2-tert-butyl-7-chloronaphtho[1,2-d]oxazole-4,5-dione (or 2-tert-butyl-8-chloronaphtho[1,2-d]oxazole-4,5-dione) as an adduct was generated (4%)

Examples 33 to 36. [Synthesis of Compounds 33 to 36]

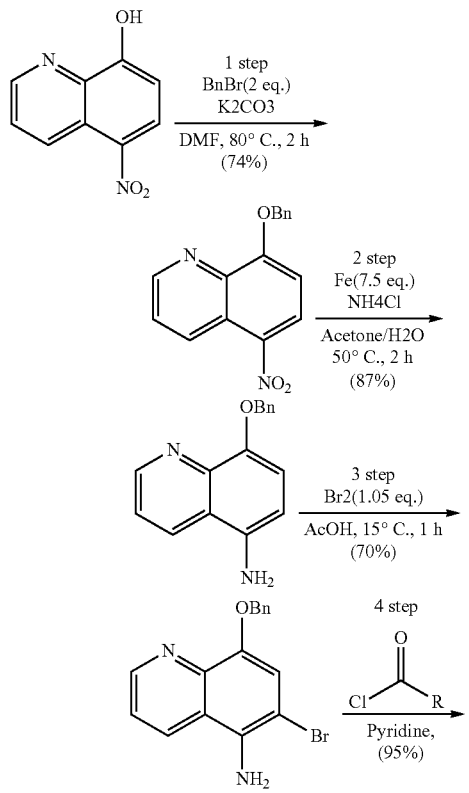

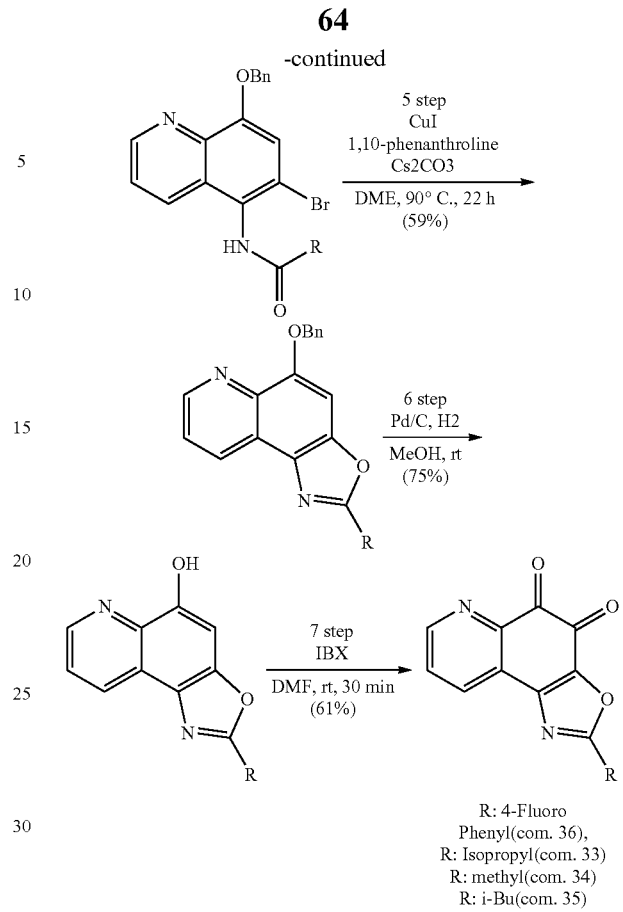

R: 4-Fluoro Phenyl(com. 36),
R: Isopropyl(com. 33)
R: methyl(com. 34)
R: i-Bu(com. 35)

Step 1: 8-(benzyloxy)-5-nitroquinoline 10 g of 5-nitroquinolin-8-ol was dissolved in 202 ml of DMF (0.26 M), and then 21.8 g of K₂CO₃ (3 eq.) was added thereto, followed by stirring for 40 minutes at 70° C. A dilute solution was changed into an orange colored slush. 12.5 ml of benzyl bromide (2 eq.) was added thereto at the same temperature and reacted for 5 hours at 80° C. When the reaction was completed, the reaction product was diluted with 800 ml of EA and then washed with 700 ml of H₂O approximately three times. An EA layer was treated with MgSO₄, filtered, and vacuum evaporated and then separated through short-column chromatography. (Hex:MC=2:1)

Light Yellow Solid: 10.93 g (74%)

Step 2: 8-(benzyloxy)quinolin-5-amine 496 ml of acetone (0.12M) and H₂O (0.5M) were added to 17.4 g of 8-(benzyloxy)-5-nitroquinoline to prepare a dilute solution. 20 g of NH₄Cl (6 eq.) was added thereto and an inner temperature was adjusted to 60° C., and then 16.8 g of Fe (5 eq.) was added thereto, followed by stirring for 1.5 hours. A reaction state may be confirmed by directly spotting on TLC without workup. If reaction was not completed, approximately two equivalents of Fe was further added thereto and reacted until a starting material was disappeared. When the reaction was completed, the reaction product was filtered through Celite and washed with EA. A filtrate was neutralized using aq. NaHCO₃, and then an organic layer was collected and an aqueous layer was washed once with MC. An EA layer and an MC layer were mixed, and then treated with MgSO₄, filtered, and vacuum evaporated. Subsequently, the reaction product was purified through recrystallization using MC:Ether.

Light Yellow Solid: 13.588 g (87%)

$^1$H NMR (300 MHz, CDCl₃) δ 8.98 (dd, J=4.5 Hz, 1.8 Hz, 1H), 8.19 (dd, J=9.0 Hz, 1.8 Hz, 1H), 7.52-7.45 (m, 2H), 7.42 (dd, J=8.4 Hz, 3.9 Hz, 1H), 7.39-7.22 (m, 3H), 6.87 (d, J=8.4 Hz, 1H), 6.67 (d, J=8.4 Hz, 1H), 5.38 (s, 2H), 3.85 (brs, 2H)

Step 3: 8-(benzyloxy)-6-bromoquinolin-5-amine 48 ml of AcOH (0.5M) was added to 6.3 g of 8-(benzyloxy)quinolin-5-amine and completely dissolved. Subsequently, 10 ml of AcOH dissolved in 1.29 ml of bromine (1.05 eq.) was added dropwise thereto for 10 minutes at an outside temperature of 10 to 15° C. The reaction product was reacted for ten minutes at the same temperature. When the reaction was completed, solid Na₂S₂O₃ was added to the reaction product, and then soot was completely dissolved using MC:MeOH and added to an Erlenmeyer flask. Water and solid NaHCO₃ were added thereto, followed by stirring while continuously adding the water and NaHCO₃ until bubbles were not generated. Extraction, treatment with MgSO₄, filtration, and vacuum evaporation were performed, and then a reaction product was separated through short-column chromatography. (MC:EA=6:1)

Orange Solid: 5.78 g (70%)

Step 4: N-(8-(benzyloxy)-6-bromoquinolin-5-yl)-4-fluorobenzamide 2.5 g of 8-(benzyloxy)-6-bromoquinolin-5-amine was dissolved in 15 ml of pyridine (0.5M) and then 1 ml of 4-fluorobenzoly chloride (1.1 eq.) was added dropwise thereto in an ice bath. The reaction product was stirred for 1 hour at room temperature. When the reaction was completed, 300 ml of EA was added thereto and washing was performed with 300 ml of H₂O approximately three times (solid product was present in an EA layer). An EA layer was directly vacuum evaporated and then purified in ether:hexane.

Ivory Solid: 3.27 g (95%)

Step 5: 5-(benzyloxy)-2-(4-fluorophenyl)oxazolo[4,5-f]quinoline 3 g of N-(8-(benzyloxy)-6-bromoquinolin-5-yl)-4-fluorobenzamide, 3.25 g of Cs₂CO₃ (1.5 eq.), 120 mg of 1,10-phenanthroline (0.1 eq.), and 63 mg of CuI (0.05 eq.) were added to a flask, and then 66 ml of DME (0.1 M) was added thereto and reacted for 16 hours at 90° C. The reaction product was not dissolved and, when temperature was elevated, a color of a yellowish brown product was changed into reddish brown. When the reaction was completed, extraction with MC, treatment with MgSO₄, and filtration using silica gel were performed. Washing was performed with MC and, at a final process, with Hex:EA of 1:1. The filtrate was vacuum evaporated and then purified through recrystallization in ether:hexane.

Ivory Solid: 2.2 g (89%)

Step 6: 2-(4-fluorophenyl)oxazolo[4,5-f]quinolin-5-ol 2 g of 5-(benzyloxy)-2-(4-fluorophenyl)oxazolo[4,5-f]quinoline was dissolved in a mixture of 54 ml of MeOH (0.1 M) and 80 ml of MC (0.067M). Subsequently, 200 mg of Pd/C was added thereto and vacuumed. Subsequently, the reaction vessel was filled with hydrogen. The reaction product was stirred for 20 hours or more at room temperature. In this regard, as reaction proceeded, a gray solid was generated in a flask. When the reaction was completed, an excess amount of THF was dissolved therein and filtration was performed through Celite. A filtrate was purified through recrystallization in ether:hexane while concentrating.

Light Gray Solid: 1.14 g (75%)

Step 7: 2-(4-fluorophenyl)oxazolo[4,5-f]quinoline-4,5-dione 42 ml of DMF (0.06 M) and 56 ml of MC (0.045 M) were added to 700 mg of 2-(4-fluorophenyl)oxazolo[4,5-f]quinolin-5-ol and 1.6 g of IBX (1.1 eq.) was added thereto portionwise. The reaction product was stirred for 2 hours at room temperature. In this regard, SM was not dissolved in an initial time but dissolved as the reaction proceeded. In this regard, when IBX was added thereto, the color of a gray reaction product was changed into yellow and then red. When the reaction was completed, an MC layer was washed with an excess amount of MC and aq. NaHCO₃ several times. The MC layer was treated with MgSO₄, filtered, and vacuum evaporated. Since a large amount of DMF was remained, 400 ml of ice water was added thereto and filtered. Subsequently, a filtered red solid was completely dissolved using MC, and then treated with MgSO₄. Subsequently, filtration and vacuum evaporation were performed. Subsequently, purification was performed through recrystallization in MC:Hex.

Orange Solid: 600 mg (81%)

1H NMR (300 MHz, CDCl₃) δ 8.88 (d, J=4.8 Hz, 1H), 8.43 (d, J=7.8 Hz, 1H), 8.35-8.30 (m, 2H), 7.66 (dd, J=7.8 Hz, 4.8 Hz, 1H), 7.32-7.28 (m, 2H)

Example 37. [Synthesis of Compound 37]

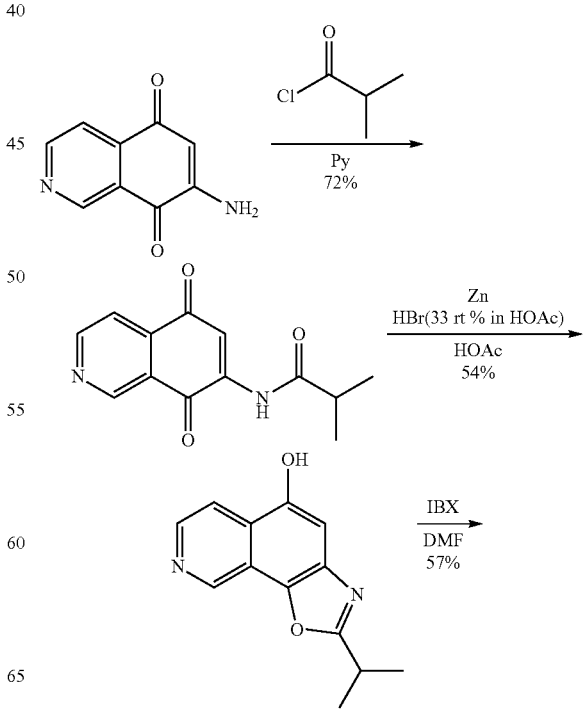

67
-continued

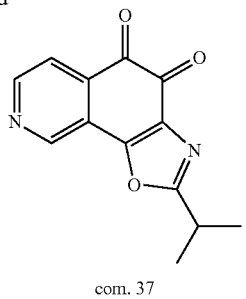

com. 37

Step 1

Pyridine (11.5 ml) was added to 7-aminoisoquinoline-5,8-dione (1 g, 5.74 mmol) and then stirred under a nitrogen atmosphere. Isobutyryl chloride (0.75 ml, 6.89 mmol) was added dropwise thereto in an ice bath and then stirred for 1 hour at 0° C. EA and distilled water were added thereto and then an organic layer was washed with distilled water several times. The separated organic layer was dried over $MgSO_4$, and then filtered and vacuum evaporated. A crude product was purified through silica gel column chromatography and recrystallization, thereby obtaining N-(5,8-dioxo-5,8-dihydroisoquinolin-7-yl)isobutyramide.

g (72%)

2) Step 2

Zinc (0.4 g, 6.14 mmol) and acetic acid (10 ml) were added to N-(5,8-dioxo-5,8-dihydroisoquinolin-7-yl)isobutyramide (0.5 g, 2.05 mmol) and stirred at room temperature. A reaction solution was heated to 80° C. and then HBr/HOAc (33 wt %) (1.2 ml, 1.35 mmol) was added thereto. The reaction product reaction solution was refluxed for 3.5 hours. EA and distilled water were added thereto and then an organic layer was washed with distilled water and an aqueous $NaHCO_3$ solution several times. The separated organic layer was dried over $MgSO_4$, and then filtered and vacuum evaporated. A crude product was purified through recrystallization, thereby obtaining 2-isopropyloxazolo[4,5-h]isoquinolin-5-ol.

0.25 g (54%)

3) Step 3

DMF (9 ml) was added to 2-isopropyloxazolo[4,5-h]isoquinolin-5-ol (0.1 g, 0.438 mmol) and stirred in an ice bath. IBX (0.31 g, 0.526 mmol) was added thereto and further stirred for 30 minutes. EA and distilled water were added thereto and then an organic layer was washed with distilled water and an aqueous $NaHCO_3$ solution several times. The separated organic layer was dried over $MgSO_4$, and then filtered and vacuum evaporated. A crude product was purified through recrystallization and filtration using silica gel filter, thereby obtaining 2-isopropyloxazolo[4,5-h]isoquinoline-4,5-dione.

60.5 mg (57%)

$^1$H NMR (300 MHz, $CDCl_3$) 9.02 (s, 1H), 8.87 (d, J=4.7 Hz, 1H), 7.83 (d, J=5.1 Hz, 1H), 3.34-3.24 (m, 1H), 1.38 (d, J=7.0 Hz, 6H)

68

Example 38. [Synthesis of Compound 38]

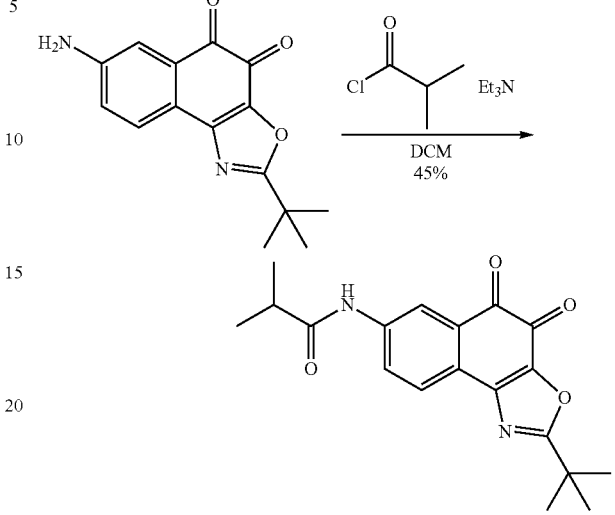

DCM (3.7 ml) was added to 7-amino-2-tert-butylnaphtho[1,2-d]oxazole-4,5-dione and then stirred under a nitrogen atmosphere. $Et_3N$ (0.3 ml, 2.22 mmol) and isobutyryl chloride (0.2 ml, 6.89 mmol) were added dropwise thereto in an ice bath and then further stirred for one hour. EA and distilled water were added thereto and then an organic layer was washed with distilled water several times. The separated organic layer was dried over $MgSO_4$, and then filtered and vacuum evaporated. A crude product was purified through recrystallization, thereby obtaining N-(2-tert-butyl-4,5-dioxo-4,5-dihydronaphtho[1,2-d]oxazol-7-yl)isobutyramide.

0.112 g (45%)

$^1$H NMR (300 MHz, $CDCl_3$) 8.37 (dd, J=8.4 Hz, 2.2 Hz, 1H), 8.00 (d, J=2.2 Hz, 1H), 7.96 (br, d, J=8.4 Hz, 1H), 2.73-2.64 (m, 1H), 1.50 (s, 9H), 1.29 (d, J=7.0 Hz, 6H)

Example 39. [Synthesis of Compound 39]

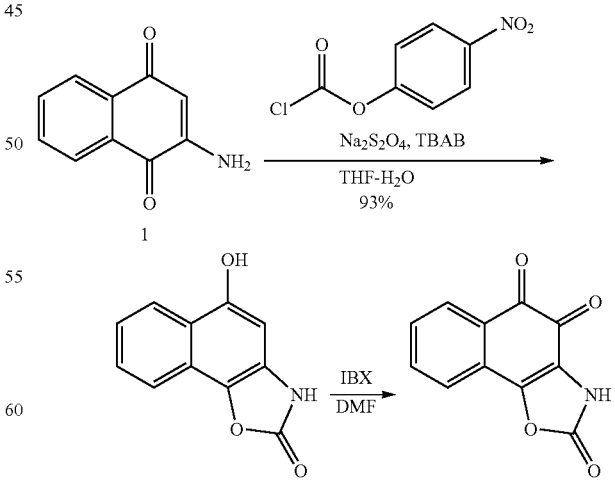

Compound 1 (2-Amino-1,4-naphthoquinone, 1.9 g, 11 mmol) was dissolved in a mixture of THF (110 ml) and distilled water (110 ml). Na₂S₂O₄ (7.6 g, 44 mmol), TBAB (Tetrabutylammonium bromide, 1.4 g, 4.4 mmol), and 4-nitrophenyl chloroformate (2.65 g, 13.2 mmol) were added thereto, followed by stirring for 19 hours under a nitrogen atmosphere. EA and a saturated aqueous NaCl solution were added thereto and then washing was performed several times. The separated organic layer was dried over MgSO₄ and then filtered. The filtered solution was vacuum evaporated and then purified through recrystallization.

Ivory Solid 2.05 g (93%)

Compound 2 (50 mg, 0.25 mmol) was dissolved in DMF (5 ml). IBX (0.18 g, 0.3 mmol) was added thereto, followed by stirring at room temperature for one hour. A saturated aqueous solution of NaCl and EA were added thereto, followed by washing several times. The separated organic layer was dried over MgSO₄ and then filtered. The filtered solution was vacuum evaporated and then separation was performed through silica gel column chromatography. Subsequently, purification was performed through recrystallization Yellow Solid ¹H NMR (300 MHz, DMSO) δ 7.85-7.83 (m, 2H), 7.69 (t, J=7.6 Hz, 7.3 Hz, 1H), 7.62 (t, J=7.3 Hz, 7.6 Hz, 1H)

Example 40. [Synthesis of Compound 40]

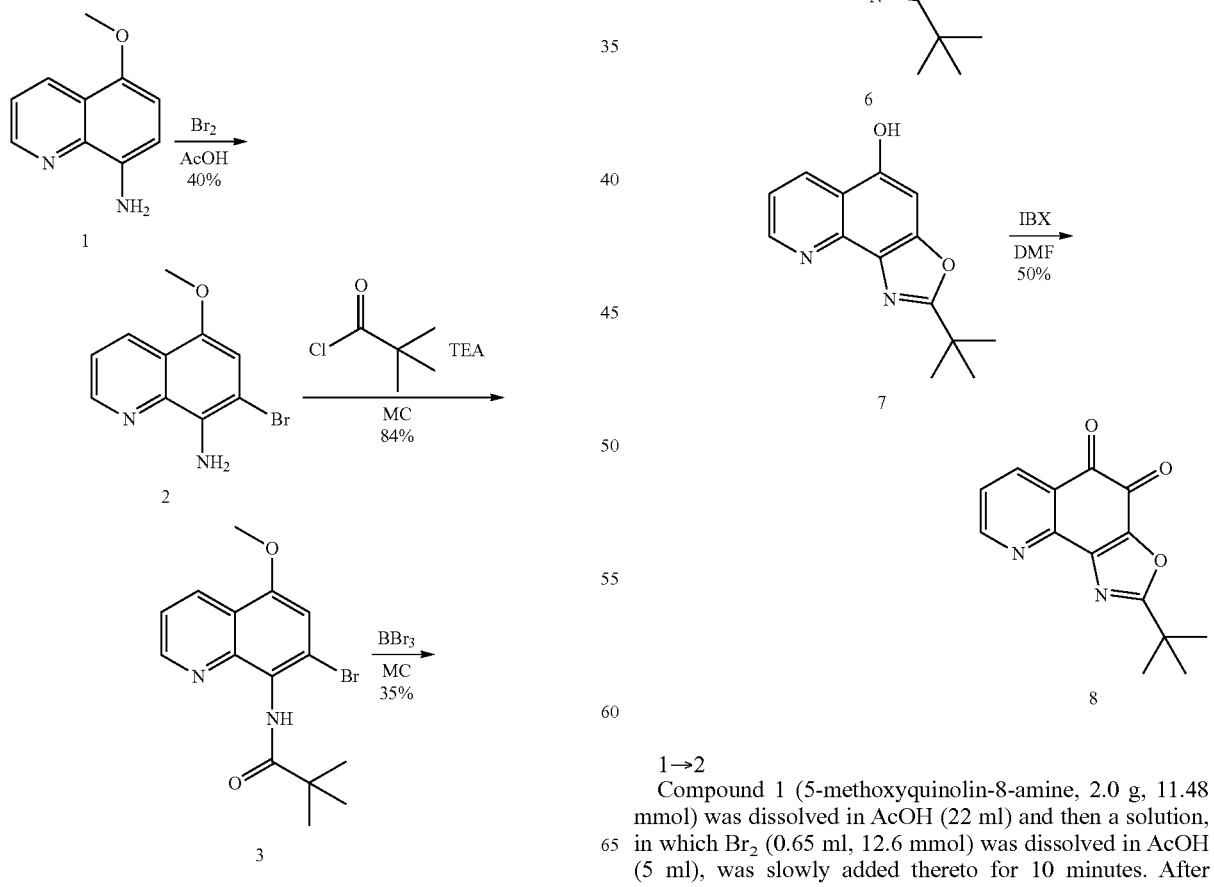

1→2

Compound 1 (5-methoxyquinolin-8-amine, 2.0 g, 11.48 mmol) was dissolved in AcOH (22 ml) and then a solution, in which Br₂ (0.65 ml, 12.6 mmol) was dissolved in AcOH (5 ml), was slowly added thereto for 10 minutes. After stirring for 20 minutes, solid Na₂S₂O₃ (1 g) was added thereto and small amounts of MeOH and MC were completely dissolved therein. Neutralization was performed using an aqueous NaHCO$_3$ solution and then extraction was performed using MC several times. An MC layer was dried over Na$_2$SO$_4$ and filtered, and then vacuum evaporated. Purification was performed through PuriShort silica column chromatography (eluent EA:HX=1:4), thereby obtaining Compound 2 (1.1 g, 40%).

2→3

Compound 2 (1.1 g, 4.35 mmol) was dissolved in MC (25 ml) and then temperature was lowered using an ice bath. TEA (1.83 ml, 13.0 mmol) was added to the reaction product and stirred for 20 minutes. Subsequently, pivaloyl chloride (0.64 ml, 5.2 mmol) was slowly added thereto. After stirring for 3 hours, the reaction product was quenched and washed several times using an aqueous NaHCO$_3$ solution. An MC layer was dried over Na$_2$SO$_4$ and filtered, and then vacuum evaporated. Purification was performed through silica gel column chromatography, thereby obtaining Compound 3 (1.24 g, 84%).

3→4

Compound 3 (1.0 g, 2.97 mmol) and MC (150 ml) were dissolved in a dried flask, followed by purging with N2. 1 M BBr$_3$ in MC (24 ml, 24 mmol) was slowly added to the reaction product. After stirring for 12 h, the reaction product was quenched and washed several times using an aqueous NaHCO$_3$ solution. An MC layer was separated, treated with Na$_2$SO$_4$, filtered, and vacuum evaporated. Subsequently, purification was performed through silica gel column chromatography, thereby obtaining Compound 4 (350 mg, yield 36%).

4→5

Compound 4 (280 mg, 0.87 mmol) was dissolved in DMF (4.5 ml), and then K$_2$CO$_3$ (0.18 g, 1.3 mmol) and KI (0.03 g, 0.17 mmol) were added thereto, followed by stirring for 20 minutes. Benzyl bromide (0.11 mL, 0.95 mmol) was slowly added thereto and reacted for 3 hours at room temperature. H$_2$O (10 mL) was added to the reaction product and temperature was lowered to 0° C. Subsequently, extracted solids were filtered. A reaction product filtrate was washed with H$_2$O and then hexane, and then dried, thereby obtaining Compound 5 (350 mg, 98%).

5→6

Compound 5 (310 mg, 0.75 mmol), CuI (0.07 g, 0.375 mmol), CsCO$_3$ (0.37 g, 1.125 mmol), and 1,10-phenanthroline (0.01 g, 0.075 mmol) were added to a round bottom flask (25 mL), followed by evacuation. DME (7.5 ml) was added thereto and then the flask was filled with nitrogen. Reaction was performed for 12 h at room temperature and then purification was performed through silica gel column chromatography, thereby obtaining Compound 6 (150 mg, 60%).

6→7

Compound 6 (140 mg, 0.42 mmol) and MeOH (5 mL) was dissolved in a round bottom flask and then 5% Pd/C (0.02 g, 0.05 mol %) was added thereto. An inner space of the flask was purged using a H$_2$ balloon and then reaction was performed overnight at room temperature. After reaction, filtration was performed through Celite and then recrystallization was performed using EA/HX. Compound 7 (60 mg, 60%) was obtained after drying.

7→8

In a round bottom flask, Compound 7 (60 mg, 0.25 mmol) was dissolved in DMF (5 mL) and then temperature was lowered to 0° C. 47% IBX (0.35 g, 2.4 mol %) was added thereto, followed by stirring for 3 hours. The reaction product was quenched using an aqueous NaHCO$_3$ solution and then extracted using EA. An EA layer was separated, treated with Na$_2$SO$_4$, filtered, and vacuum evaporated, thereby obtaining Compound 8 (31 mg, yield of 50%).

1H NMR (300 MHz, CDCl3) δ 8.93-8.91 (dd, J=4.8, 1.5 Hz, 1H), 8.38-8.35 (dd, J=7.8, 1.5 Hz, 1H), 7.52-7.48 (dd, J=7.8, 4.8 Hz, 1H), 1.55 (s, 9H)

Example 41. [Synthesis of Compound 41]

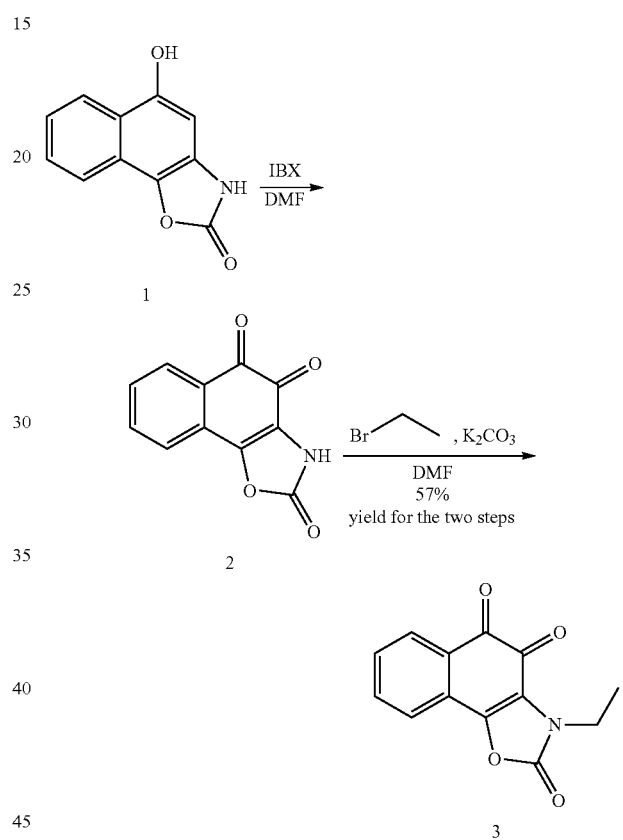

Compound 1 (1 g, 4.97 mmol) was dissolved in DMF (100 ml) and then IBX (3.55 g, 5.96 mmol) was added thereto. Reaction was performed for one hour at room temperature, and then a saturated aqueous NaCl solution and EA were added thereto and extraction was performed several times. The separated organic layer was dried over MgSO$_4$ and then filtered. The filtered solution was vacuum evaporated and redissolved in DMF (100 ml). K$_2$CO$_3$ (3.4 g, 24.8 mmol) and ethyl bromide (1.85 ml, 24.8 mmol) were added thereto, followed by stirring for 6 hours at 60° C. Extraction was performed by adding NaHCO$_3$, a saturated aqueous NaCl solution, and EA, and then a separated organic layer was dried over MgSO$_4$, filtered, and vacuum evaporated. Separation was performed through silica gel column chromatography and then purification was performed through recrystallization.

Gold Solid 0.69 g (57%)

$^1$H NMR (300 MHz, CDCl$_3$) δ 8.16-8.09 (m, 2H), 7.82-7.76 (m, 2H), 4.17 (q, J=7.1 Hz, 2H), 1.42 (t, J=7.1 Hz, 3H)

Example 42. [Synthesis of Compound 42]

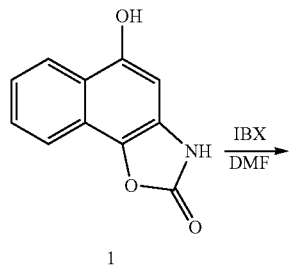

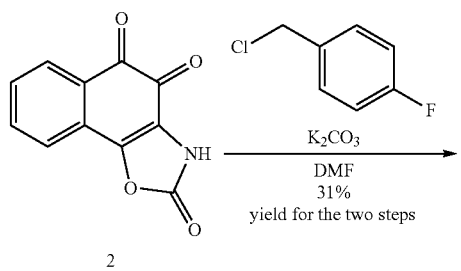

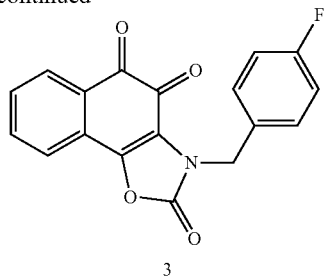

Compound 1 (0.2 g, 0.99 mmol) was dissolved in DMF (20 ml) and then IBX (0.7 g, 1.19 mmol) was added thereto. Reaction was performed for 1.5 hours at room temperature, and then a saturated aqueous NaCl solution and EA were added thereto and extraction was performed several times. The separated organic layer was dried over MgSO$_4$ and then filtered. The filtered solution was vacuum evaporated and redissolved in DMF (20 ml. 0.05 M). K$_2$CO$_3$ (0.68 g, 4.97 mmol) and 4-fluorobenzyl chloride (0.6 ml, 4.97 mmol) were added thereto, followed by stirring for 14 hours at 60° C. NaHCO$_3$, a saturated aqueous NaCl solution, and EA were added thereto and extraction was performed. Subsequently, a separated organic layer was dried over MgSO$_4$, filtered, and vacuum evaporated. Separation was performed through silica gel column chromatography and then purification was performed through recrystallization.

Yellow Solid 0.1 g (31%)

$^1$H NMR (300 MHz, CDCl$_3$) δ 8.14-8.09 (m, 2H), 7.79-7.76 (m, 2H), 7.57-7.52 (m, 2H), 7.07-7.01 (m, 2H), 5.23 (s, 2H)

Examples 43, 44, 45, and 46. [Synthesis of Compounds 43, 44, 45, and 46]

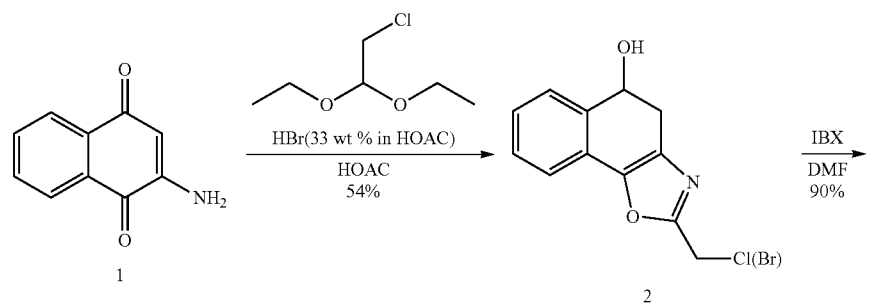

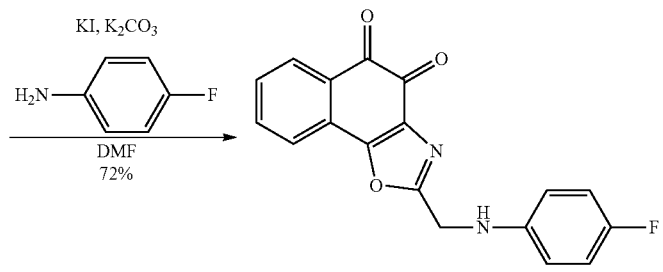

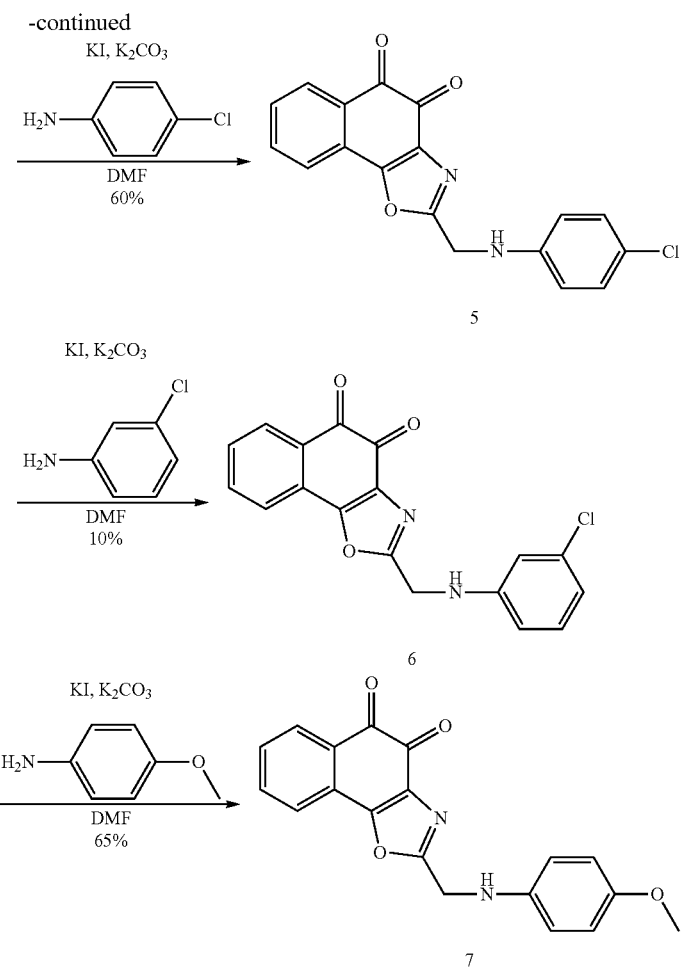

AcOH (50 ml) and HBr (33 wt % in AcOH) (10 ml) were added to chloroacetaldehyde diethylacetal (30.5 ml, 202 mmol) and stirred for 10 minutes under a nitrogen atmosphere. Compound 1 (2-Amino-1,4-naphthoquinone, 7 g, 40.4 mmol) dissolved in AcOH (150 ml) was added to the above solution. A reaction solution was stirred for 7 hours at room temperature and then poured onto ice. Neutralization was performed using saturated aqueous $NaHCO_3$, and then EA was added thereto and extraction was performed several times. The separated organic layer was dried over $MgSO_4$ and then filtered. The filtered solution was vacuum evaporated and then crystallized.

Brown Solid 5.12 g (54%)

Compound 2 (1.7 g, 7.1 mmol) was dissolved in DMF (142 ml) and then IBX (5.1 g, 8.5 mmol) was added thereto. Reaction was performed for one hour at room temperature, and then saturated aqueous $NaHCO_3$ and EA were added thereto and extraction was performed several times. The separated organic layer was dried over $MgSO_4$ and then filtered. The filtered solution was vacuum evaporated and then filtered through silica gel. Subsequently, purification was performed through recrystallization.

Orange Solid 1.6 g (90%)

Compound 43 (Compound 4)

4-fluoroaniline (0.37 ml, 3.88 mmol) and KI (86 mg, 0.52 mmol) were dissolved in DMF (42 ml) and then $K_2CO_3$ (0.45 g, 3.23 mmol) was added thereto. Compound 3 (0.8 g, 3.23 mmol) was added thereto at the same temperature and stirred under a nitrogen atmosphere. A reaction solution was heated to 60° C. and then further stirred for 3 hours. The reaction solution was poured onto ice and a solid was filtered out. Washing was performed using EA and distilled water several times.

Brown Solid 0.75 g (72%)

$^1$H NMR (300 MHz, DMSO) δ 7.97 (d, J=7.6 Hz, 1H), 7.76 (t, J=7.5 Hz, 1H), 7.66 (d, J=7.2 Hz, 1H), 7.59 (t, J=7.5 Hz, 1H), 6.97-6.91 (m, 2H), 6.72-6.67 (m, 2H), 6.41 (t, J=6.4 Hz, 1H)

Compound 44 (Compound 5)

4-chloroaniline (62 mg, 0.49 mmol) and KI (40 mg) were dissolved in DMF (5.3 ml) and then $K_2CO_3$ (56 mg, 0.4 mmol) was added thereto. Compound 3 (0.1 g, 0.4 mmol) was added thereto at the same temperature and stirred under a nitrogen atmosphere. A reaction solution was heated to 60° C. and then further stirred for 1.5 hours. A saturated aqueous NaCl solution and EA were added thereto and extraction was performed. Subsequently, a separated organic layer was dried over $MgSO_4$ and filtered. The filtered solution was vacuum evaporated and then purified through recrystallization.

Brown Solid 82 mg (60%)

$^1$H NMR (300 MHz, DMSO) δ 7.97 (d, J=7.1 Hz, 1H), 7.76 (t, J=7.6 Hz, 1H), 7.66 (d, J=7.1 Hz, 1H), 7.59 (t, J=7.6

Hz, 1H), 7.12 (d, J=8.8 Hz, 2H), 6.71 (d, J=8.8 Hz, 2H), 4.58 (s, 2H)

Compound 45 (Compound 6)

3-chloroaniline (51 ul, 0.49 mmol) and KI (40 mg) were dissolved in DMF (5.3 ml) and then K$_2$CO$_3$ (56 mg, 0.4 mmol) was added thereto. Compound 3 (0.1 g, 0.4 mmol) was added thereto at the same temperature and stirred under a nitrogen atmosphere. A reaction solution was heated to 60° C. and then further stirred for 2 hours. A saturated aqueous NaCl solution and EA were added thereto and extraction was performed. Subsequently, a separated organic layer was dried over MgSO$_4$ and filtered. The filtered solution was vacuum evaporated and then separated through silica gel column chromatography. Subsequently, purification was performed through recrystallization.

Brown Solid 14 mg (10%)

$^1$H NMR (300 MHz, CDCl$_3$) δ 8.16 (d, J=7.5 Hz, 1H), 7.72-7.70 (m, 2H), 7.60-7.58 (m, 1H), 7.13 (t, J=7.7 Hz, 8.2 Hz, 1H), 6.77 (d, J=7.3 Hz, 1H), 6.72 (m, 1H), 6.64 (d, J=8.2 Hz, 1H), 4.60 (s, 2H)

Compound 46 (Compound 7)

P-anisidine (60 mg, 0.49 mmol) and KI (40 mg) were dissolved in DMF (5.3 ml) and then K$_2$CO$_3$ (56 mg, 0.4 mmol) was added thereto. Compound 3 (0.1 g, 0.4 mmol) was added thereto at the same temperature and stirred under a nitrogen atmosphere. A reaction solution was heated to 60° C. and then further stirred for 3 hours. A saturated aqueous NaCl solution and EA were added thereto and extraction was performed. Subsequently, a separated organic layer was dried over MgSO$_4$ and filtered. The filtered solution was vacuum evaporated and then filtered through silica gel. Subsequently, purification was performed through recrystallization.

Brown Solid 88 mg (65%)

$^1$H NMR (300 MHz, CDCl$_3$) δ 8.13 (d, J=7.9 Hz, 1H), 7.70-7.68 (m, 2H), 7.58-7.53 (m, 1H), 6.79 (d, J=8.9 Hz, 2H), 6.71 (d, J=8.9 Hz, 2H), 4.56 (s, 2H), 3.73 (s, 3H)

Example 47. [Synthesis of Compound 47]

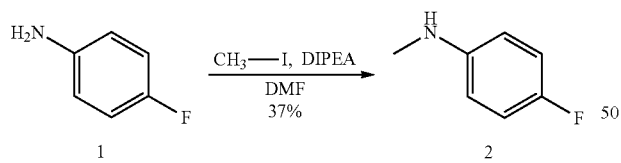

Compound 1 (4-fluoroaniline, 3 g, 27 mmol) was dissolved in DMF (30 ml) and then DIPEA (5.6 ml, 32.4 mmol) and iodomethane (1.84 ml, 29.7 mmol) was added thereto. A reaction solution was stirred for 30 minutes at 70° C. The reaction solution was poured onto ice and a saturated aqueous NaCl solution and EA were added thereto for extraction. The separated organic layer was dried over MgSO$_4$ and filtered. The filtered solution was vacuum evaporated and then purification was performed through silica gel column chromatography.

Amber Liquid 1.25 g (37%)

$^1$H NMR (300 MHz, CDCl$_3$) δ 6.94-6.85 (m, 2H), 6.57-6.50 (m, 2H), 2.80 (s, 3H)

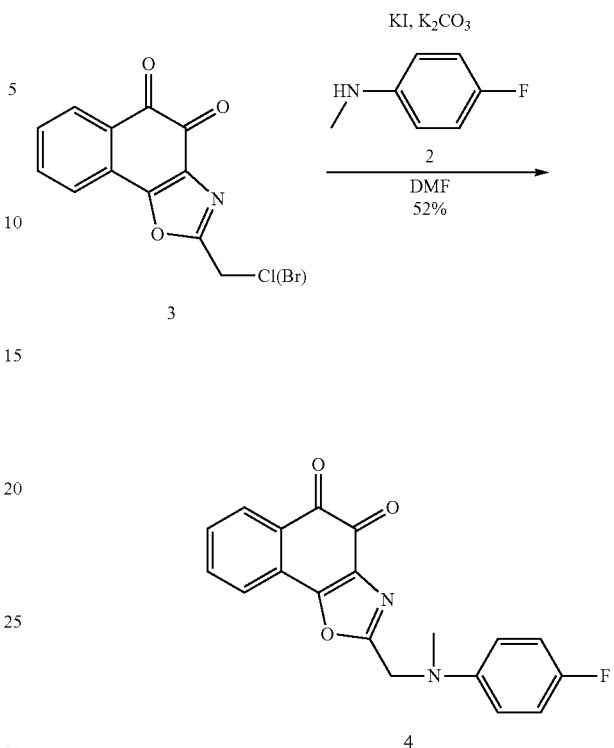

Compound 3 (1.5 g, 6.14 mmol) was dissolved in DMF (81 ml) and then KI (0.16 g, 0.98 mmol), K$_2$CO$_3$ (0.85 g, 6.14 mmol), and Compound 2 (4-fluoro-N-methylaniline, 0.9 ml, 7.37 mmol) were added thereto. A reaction solution was stirred for 4 hours at 60° C. The reaction solution was poured onto ice and a saturated aqueous NaCl solution and EA were added thereto for extraction. The separated organic layer was dried over MgSO$_4$ and filtered. The filtered solution was vacuum evaporated and then filtered using silica. Subsequently, purification was performed through recrystallization.

Gold Solid 1.08 g (52%)

$^1$H NMR (300 MHz, CDCl$_3$) δ 8.13 (d, J=7.7 Hz, 1H), 7.69-7.55 (m, 3H), 7.00-6.94 (m, 2H), 6.85-6.81 (m, 2H), 4.67 (s, 2H), 3.13 (s, 3H)

Example 48. [Synthesis of Compound 48]

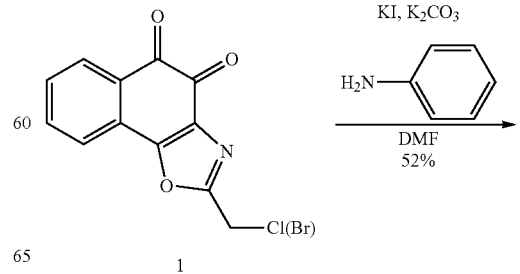

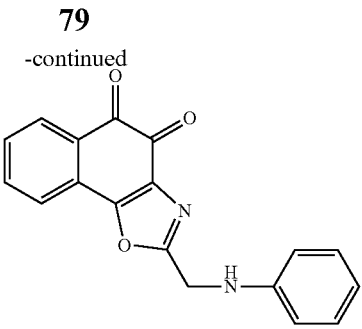

2

Aniline (44 µl, 0.485 mmol) and KI (11 mg, 0.065 mmol) were dissolved in DMF (5.3 ml) and then $K_2CO_3$ (56 mg, 0.404 mmol) was added thereto. Compound 3 (0.1 g, 0.4 mmol) was added thereto at the same temperature and stirred under a nitrogen atmosphere. A reaction solution was heated to 60° C. and then further stirred for 2 hours. The reaction solution was poured onto ice and a saturated aqueous NaCl solution and EA were added thereto for extraction. The separated organic layer was dried over $MgSO_4$ and filtered. The filtered solution was vacuum evaporated and then filtered using silica. Subsequently, purification was performed through recrystallization.

Brown Solid 42.8 mg (34%)

$^1$H NMR (300 MHz, DMSO) δ 7.95-7.48 (m, 3H), 7.12-7.06 (m, 2H), 6.70 (d, J=7.9 Hz, 2H), 6.58 (t, J=7.1 Hz, 7.3 Hz, 1H), 6.47-6.43 (m, 1H), 4.57 (s, 2H)

Example 49. [Synthesis of Compound 49]

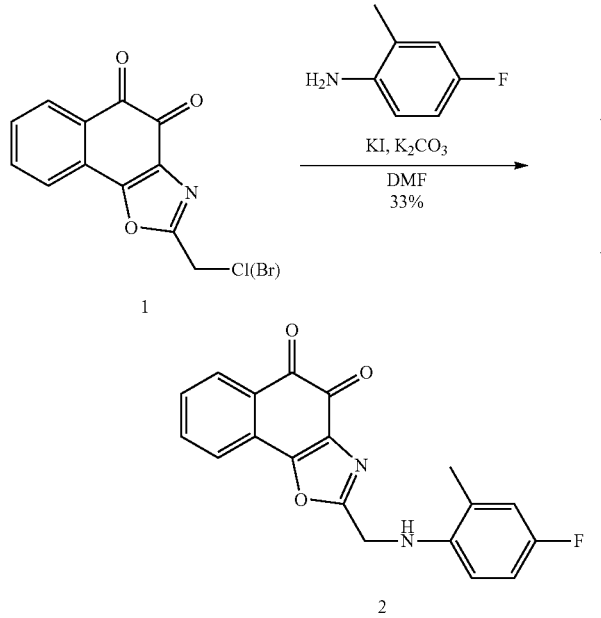

4-fluoro-2-methyl aniline (54 ul, 0.485 mmol) and KI (11 mg, 0.065 mmol) were dissolved in DMF (5.3 ml) and then $K_2CO_3$ (56 mg, 0.404 mmol) was added thereto. Compound 3 (0.1 g, 0.4 mmol) was added thereto at the same temperature and stirred under a nitrogen atmosphere. A reaction solution was heated to 60° C. and then further stirred for 2.5 hours. The reaction solution was poured onto ice and a saturated aqueous NaCl solution and EA were added thereto for extraction. The separated organic layer was dried over $MgSO_4$ and filtered. The filtered solution was vacuum evaporated and then filtered using silica. Subsequently, purification was performed through recrystallization.

Brown Solid 45 mg (33%)

$^1$H NMR (300 MHz, $CDCl_3$) δ 8.14 (d, J=8.0 Hz, 1H), 7.71-7.67 (m, 2H), 7.59-7.54 (m, 1H), 6.84 (d, J=8.6 Hz, 1H), 6.85-6.80 (m, 1H), 6.79-6.63 (m, 1H), 4.62 (d, J=6.0 Hz, 2H), 2.23 (s, 3H)

Example 50. [Synthesis of Compound 50]

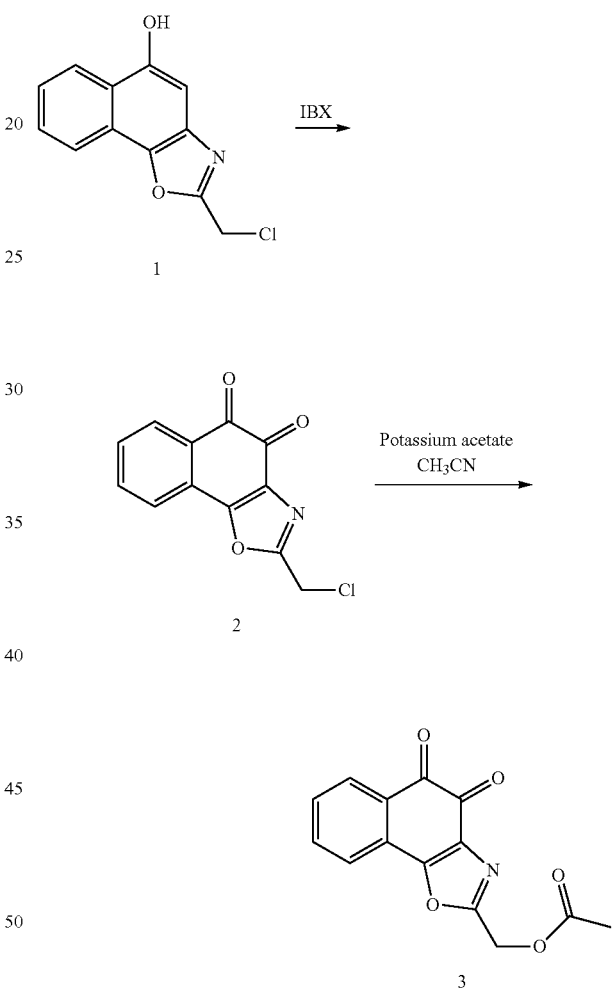

1→2

DMF (4 ml) was added to Compound 1 (100 mg, 0.428 mmol). IBX (280 mg, 0.471 mmol) was added thereto, followed by stirring for 3 hours at room temperature. Water was poured thereinto and then extraction was performed using EA. A separate EA layer was dried over $MgSO_4$, vacuum distilled, and subjected to column chromatography, thereby obtaining a target compound.

35 mg (33%)

2→3

ACN (1.2 ml) was added to Compound 2 (30 mg, 00.12 mmol) and KOAc (18 mg, 0.18 mmol) was added thereto. The reaction product was reacted for 18 hours at 50° C.

Water was poured thereinto and then extraction was performed using EA. A separate EA layer was dried over MgSO₄, vacuum distilled, and recrystallized, thereby obtaining a target compound.

25 mg (80%)

¹H NMR (300 MHz, CDCl₃) 8.18 (d, J=7.8 Hz, 1H), 7.75-7.73 (m, 2H), 7.62-7.56 (m, 1H), 5.31 (s, 2H), 2.21 (s, 3H)

Example 51. [Synthesis of Compound 51]

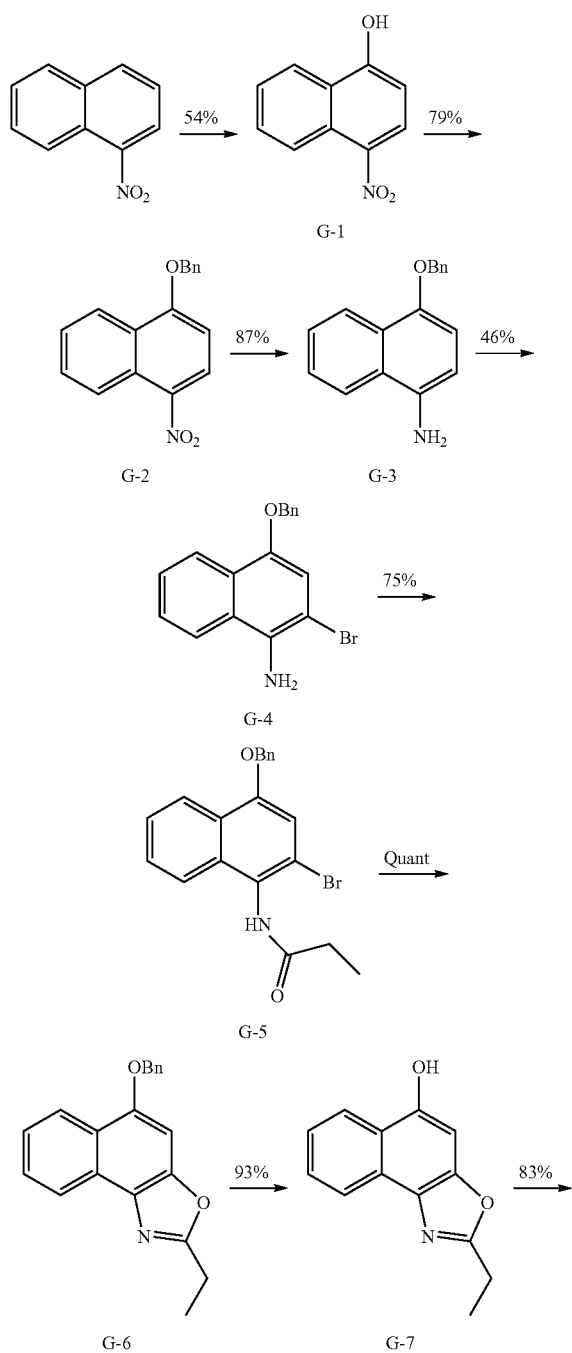

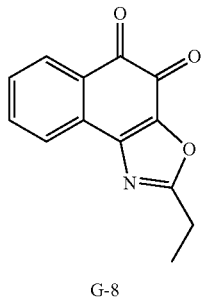

Step a

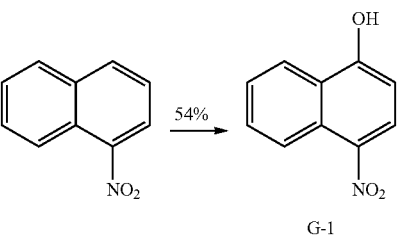 [SMILES: O=[N+]([O-])c1cccc2ccccc12 ; O=[N+]([O-])c1ccc(O)c2ccccc12]

SM (1.5 g, 8.7 mmol) was dissolved in DMSO (30 ml) and an aqueous KOH solution was added dropwise thereto. Cumene hydroperoxide (1.5 ml, 10.8 mmol) was added to a reaction solution and stirred for 3 hours at room temperature. The reaction product was neutralized using water and pH was adjusted to 6.5 using 1N HCl. Extraction was performed using EA. A reaction product extract was dried over MgSO₄, filtered, vacuum distilled, and subjected to column chromatography using silica gel, thereby obtaining a target compound. G-1 (0.34 g, 54%)

¹H NMR (300 MHz, CDCl₃) 8.79 (d, J=8.6 Hz, 1H), 8.46 (d, J=8.6 Hz, 1H), 7.79-7.74 (m, 1H), 7.65-7.59 (m, 1H), 6.84 (d, J=8.6 Hz, 1H), 6.38 (s, 1H)

Step b

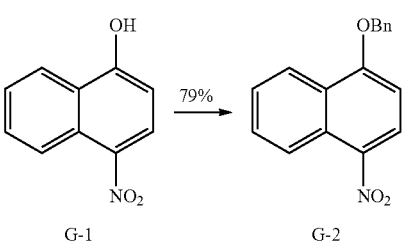 [SMILES: O=[N+]([O-])c1ccc(O)c2ccccc12 ; O=[N+]([O-])c1ccc(OCc2ccccc2)c2ccccc12]

Compound G-1 (0.5 g, 2.6 mmol) was added to DMF (10 ml), and then K₂CO₃ (1.1 g, 7.9 mmol) was added thereto and temperature was elevated to 80° C. Benzyl bromide (0.65 ml, 5.2 mmol) was added thereto, followed by stirring for 25 minutes. After completing reaction, water was added thereto and extraction was performed using EA. An EA layer was dried over MgSO₄, filtered, vacuum distilled, and subjected to column chromatography using silica gel, thereby obtaining a target compound. G-2 (0.58 g, 79%)

¹H NMR (300 MHz, CDCl₃) 8.79 (td, J=3.8 Hz, J=10.6 Hz, 1H), 8.46 (d, J=2.8 Hz, J=4.6 Hz, 1H), 8.40 (d, J=8.6 Hz, 1H), 7.76 (t, J=7.9 Hz, 1H), 7.60 (t, J=7.6 Hz, 1H), 7.54-7.38 (m, 5H), 6.91 (d, J=8.8 Hz, 1H), 5.36 (s, 2H)

Step c

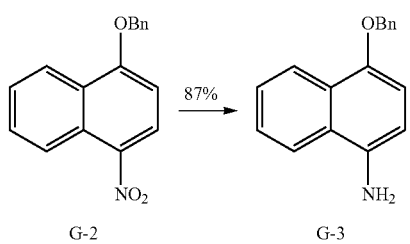 [SMILES: O=[N+]([O-])c1ccc(OCc2ccccc2)c2ccccc12 ; Nc1ccc(OCc2ccccc2)c2ccccc12]

5) Step e

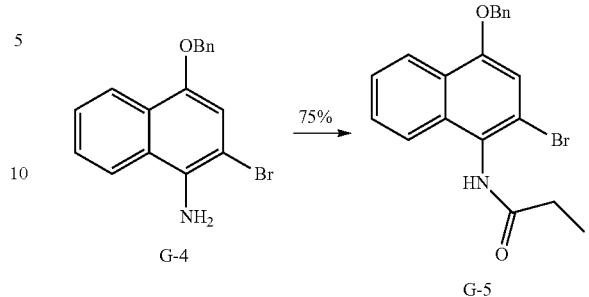

Acetone (14.5 ml, 0.125 M) and H₂O (3.6 ml, 0.5 M) were added to Compound G-2 (0.5 g, 1.8 mmol) and then NH₄Cl (0.58 g, 10.8 mmol) was added thereto. When a temperature of the reaction product was 60° C., Fe (0.8 g, 14.4 mmol) was added thereto, followed by stirring for 2 hours. The reaction product was cooled and then filtered through Celite. A filtrate was extracted using EA. The separated organic layer was dried over MgSO₄, filtered, vacuum distilled, and subjected to column chromatography using silica gel, thereby obtaining a target compound. G-3 (0.39 g, 87%)

¹H NMR (300 MHz, CDCl₃) 8.37-8.32 (m, 1H), 7.86-7.81 (s, 1H), 7.53-7.33 (m, 7H), 6.76 (d, J=8.0 Hz, 2H), 6.70 (s, J=7.9 Hz, 1H), 3.87 (s, 2H)

Step d

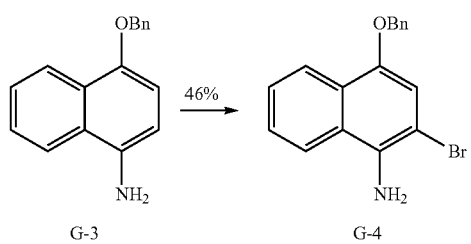 [SMILES: Nc1ccc(OCc2ccccc2)c2ccccc12 ; Nc1c(Br)cc(OCc2ccccc2)c2ccccc12]

Dichloromethane (20 ml) and Et₃N (1.15 ml, 8.2 mmol) were added to Compound G-4 (0.9 g, 2.7 mmol) and, in an ice bath, propionyl chloride (0.3 ml, 3.3 mmol) was added thereto. Stirring was performed for 12 hours at room temperature and then neutralization was performed by adding H₂O. Extraction was performed using EA, a separated organic layer was dried over MgSO₄, filtered, vacuum distilled, and recrystallized (ether/hexane), thereby obtaining a target compound (0.77 g, 75%)

¹H NMR (300 MHz, CDCl₃) 8.30 (d, J=7.1 Hz, 1H), 7.80 (d, J=7.1 Hz, 1H), 7.58-7.38 (m, 5H), 7.08 (s, 1H), 5.23 (s, 2H), 2.60 (q, J=7.6 Hz, 2H), 1.39 (t, J=7.5 Hz, 3H)

Step f

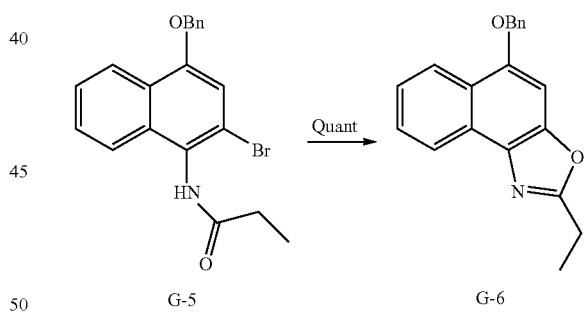

EA (125 ml, 0.05 M) was added to Compound G-3 (1.5 g, 6.18 mmol) and stirred in an ice bath. In another vial, Br₂ was diluted with EA (12.5 ml, 0.5 M) and then added dropwise to a reaction container containing G-3. Stirring was performed for 10 minutes and then neutralization was performed by adding an aqueous Na₂S₂O₃ solution. Subsequently, extraction was performed using EA. The organic layer was dried over MgSO₄, filtered, vacuum distilled, and subjected to column chromatography using silica gel, thereby obtaining a target compound. G-4 (0.93 g, 46%)

¹H NMR (300 MHz, CDCl₃) 8.31-8.27 (m, 1H), 7.82-7.79 (m, 1H), 7.56-7.35 (m, 7H), 6.97 (s, 1H), 5.16 (s, 2H), 4.28 (s, 2H)

Compound G-5 (0.55 g, 1.43 mmol), CuI (0.0136 g, 0.07 mmol), 1,10-phenanthroline (0.03 g, 0.14 mmol), and Cs₂CO₃ (00.7 g, 2.1 mmol) were added to dimethoxyethane (15 ml, 0.1 M) and stirred for 5 hours at 100° C. The reaction product was cooled and then extraction thereof was performed using water and MC. The organic layer was dried over MgSO₄, filtered, vacuum distilled, and recrystallized, thereby obtaining a target compound. G-6 (0.43 g, 99%)

¹H NMR (300 MHz, CDCl₃) 8.41 (d, J=2.9 Hz, J=4.8 Hz, 1H), 7.68-7.63 (m, 1H), 7.56-7.35 (m, 6H), 7.01 (s, 1H) 3.03 (q, J=7.6 Hz, 1H), 1.48 (t, J=7.6 Hz, 1H)

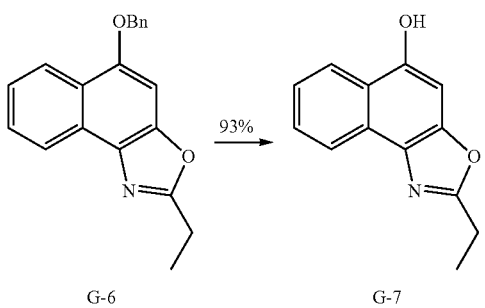 [SMILES: CCc1nc2c(cc(OCc3ccccc3)c3ccccc32)o1 ; CCc1nc2c(cc(O)c3ccccc32)o1]

Methanol (20 ml, 0.1 M) was added to Compound G-6 (0.59 g, 1.95 mmol) and Pd/C (50 mg) was added thereto. After degassing, a $H_2$ balloon was attached and then reaction was performed for 12 hours at room temperature. Filtration was performed through Celite and then vacuum distillation was performed, thereby obtaining a target compound. G-7 (390 mg, 93%)

$^1$H NMR (300 MHz, CDCl$_3$) 8.42 (d, J=8.2 Hz, 1H), 8.26 (d, J=8.8 Hz, 1H), 7.66 (t, J=7.4 Hz, 1H), 7.53 (t, J=7.5 Hz, 1H), 7.08 (s, 1H), 3.03 (q, J=7.6 Hz, 2H), 1.48 (t, J=7.6 Hz, 3H)

7) Step g

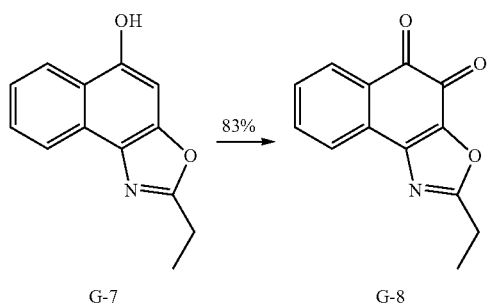 [SMILES: CCc1nc2c(cc(O)c3ccccc32)o1 ; CCc1nc2c(o1)C(=O)C(=O)c1ccccc1-2]

DMF (30 ml, 0.06 M) was added to Compound G-7 (0.39 g, 1.83 mmol) and then IBX (1.2 g, 2.01 mmol) was added thereto. The reaction product was reacted for 1 hour at room temperature. $H_2O$ was added thereto and then extraction was performed using EA. The organic layer was dried over MgSO$_4$, filtered, vacuum distilled, and subjected to column chromatography using silica gel, thereby obtaining a target compound. G-8 (0.34 g, 83%)

$^1$H NMR (300 MHz, CDCl$_3$) 8.12 (dd, J=7.7 Hz, J=1.3 Hz 1H), 7.95 (d, J=7.5 Hz, J=1.1 Hz, 1H), 7.70 (dt, J=10.6 Hz, J=3.8 Hz 1H), 7.53 (dt, J=10.6 Hz, J=3.8 Hz 1H), 3.00 (q, J=7.6 Hz, 2H), 1.47 (t, J=7.5 Hz, 3H)

Experimental Example 1: NQO1 Activity Measurement

An enzyme reaction solution included 25 mM Tris/HCl (pH 7.4), 0.14% bovine serum albumin, 200 μM NADH, 77 μM cytochrome C, and 5 ng of NQO1 protein. Enzymatic reaction was initiated by adding NADH and performed at 37° C. In this regard, a reaction rate was measured by observing absorbance, which was increased due to reduction of cytochrome C, at 550 nm for 10 minutes and NQO1 activity was represented as an amount of reduced cytochrome C [nmol cytochrome C reduced/min/μg protein].

Extinction coefficient for cytochrome C:21.1 mmol/L/cm=21.1 μmol/ml/cm

Results are summarized in Table 1 below.

TABLE 1

| Compounds | NQO1 activity (5 μM, [nmol cytochrome C reduced/min/μg protein]) |
|---|---|
| Example 1 (Compound 1) | 255.2 |
| Example 2 (Compound 2) | 243.2 |
| Example 3 (Compound 3) | 255.5 |
| Example 4 (Compound 4) | 207.3 |
| Example 5 (Compound 5) | 259.5 |
| Example 6 (Compound 6) | 171.8 |
| Example 7 (Compound 7) | 69.8 |
| Example 8 (Compound 8) | 205.1 |
| Example 9 (Compound 9) | 73.6 |
| Example 10 (Compound 10) | 20.7 |
| Example 11 (Compound 11) | 149.2 |
| Example 12 (Compound 12) | 379.2 |
| Example 13 (Compound 13) | 68.6 |
| Example 14 (Compound 14) | 104.2 |
| Example 15 (Compound 15) | 20.8 |
| Example 16 (Compound 16) | 4.2 |
| Example 17 (Compound 17) | 7.4 |
| Example 18 (Compound 18) | 382.9 |
| Example 19 (Compound 19) | 0.4 |
| Example 20 (Compound 20) | 221.0 |
| Example 21 (Compound 21) | 40.3 |
| Example 22 (Compound 22) | 102.5 |
| Example 23 (Compound 23) | 60.9 |
| Example 24 (Compound 24) | 321.7 |
| Example 25 (Compound 25) | 23.5 |
| Example 26 (Compound 26) | 275.4 |
| Example 27 (Compound 27) | 241.9 |
| Example 28 (Compound 28) | 254.9 |
| Example 29 (Compound 29) | 610.6 |
| Example 30 (Compound 30) | 213.0 |
| Example 31 (Compound 31) | 220.3 |
| Example 32 (Compound 32) | 397.2 |
| Example 33 (Compound 33) | 458.3 |
| Example 34 (Compound 34) | 923.5 |
| Example 35 (Compound 35) | 662.8 |
| Example 36 (Compound 36) | 936.1 |
| Example 37 (Compound 37) | 845.7 |
| Example 38 (Compound 38) | 63.4 |
| Example 39 (Compound 39) | 30.1 |
| Example 40 (Compound 40) | 527.4 |
| Example 41 (Compound 41) | 237.1 |
| Example 42 (Compound 42) | 208.0 |
| Example 43 (Compound 43) | 263.0 |
| Example 44 (Compound 44) | 239.0 |
| Example 45 (Compound 45) | 229.2 |
| Example 46 (Compound 46) | 208.0 |
| Example 47 (Compound 47) | 227.5 |
| Example 48 (Compound 48) | 241.4 |
| Example 49 (Compound 49) | 229.6 |
| Example 50 (Compound 50) | 244.3 |
| Example 51 (Compound 51) | 240.9 |

As shown in Table 1, it can be confirmed that the compounds according to the present invention exhibit NQO1 activity.

Experimental Example 2: Measurement of Lactate Change Amount within Cells

Cells were treated with 400 μl of 6% PCA, and then collected and extracted. Centrifugation (13,000 rpm, 10 min) was performed. A precipitate was dried using a Speed-Vac and then a weight of dried precipitate was measured. A supernatant was neutralized using 400 μl of 1 M KOH and a final volume thereof was adjusted to 1 ml using 0.33 M KH$_2$PO$_4$/K$_2$HPO$_4$, pH 7.5. Centrifugation (13,000 rpm, 10 min) was performed and the amount of lactate in a supernatant was measured (Megazyme, K-LATE).

Results are summarized in Table 2 below.

TABLE 2

| Compounds | Lactate change amount within cells (nmol/mg cell) |
|---|---|
| Example 1 (Compound 1) | 5.2 |
| Example 2 (Compound 2) | 6.8 |
| Example 3 (Compound 3) | 8.1 |
| Example 4 (Compound 4) | 9.3 |
| Example 5 (Compound 5) | 5.9 |
| Example 6 (Compound 6) | 6.7 |
| Example 7 (Compound 7) | 8.0 |
| Example 8 (Compound 8) | 6.2 |
| Example 9 (Compound 9) | 7.3 |
| Example 10 (Compound 10) | 11.5 |
| Example 11 (Compound 11) | 6.6 |
| Example 12 (Compound 12) | 10.3 |
| Example 13 (Compound 13) | — |
| Example 14 (Compound 14) | — |
| Example 15 (Compound 15) | 4.1 |
| Example 16 (Compound 16) | — |
| Example 17 (Compound 17) | — |
| Example 18 (Compound 18) | 13.5 |
| Example 19 (Compound 19) | — |
| Example 20 (Compound 20) | 9.2 |
| Example 21 (Compound 21) | — |
| Example 22 (Compound 22) | — |
| Example 23 (Compound 23) | — |
| Example 24 (Compound 24) | 15.1 |
| Example 25 (Compound 25) | — |
| Example 26 (Compound 26) | 10.1 |
| Example 27 (Compound 27) | 5.8 |
| Example 28 (Compound 28) | 7.4 |
| Example 29 (Compound 29) | 7.4 |
| Example 30 (Compound 30) | 7.3 |
| Example 31 (Compound 31) | 10.9 |
| Example 32 (Compound 32) | 9.8 |
| Example 33 (Compound 33) | 10.2 |
| Example 34 (Compound 34) | 8.9 |
| Example 35 (Compound 35) | 10.4 |
| Example 36 (Compound 36) | 7.3 |
| Example 37 (Compound 37) | 10.6 |
| Example 38 (Compound 38) | 4.6 |
| Example 39 (Compound 39) | 7.8 |
| Example 40 (Compound 40) | 8.1 |
| Example 41 (Compound 41) | 5.2 |
| Example 42 (Compound 42) | 7.1 |
| Example 43 (Compound 43) | 4.4 |
| Example 44 (Compound 44) | 5.4 |
| Example 45 (Compound 45) | 6.7 |
| Example 46 (Compound 46) | 7.4 |
| Example 47 (Compound 47) | 7.6 |
| Example 48 (Compound 48) | 6.9 |
| Example 49 (Compound 49) | 6.0 |
| Example 50 (Compound 50) | 8.8 |
| Example 51 (Compound 51) | 5.7 |

From Table 2, lactate activity within cells according to examples of the present invention can be confirmed. Since a ratio of NAD/NADH follows a ratio of pyruvate/lactate, ratios of NAD/NADH within cytosols may be measured from the pyruvate/lactate ratio. Therefore, when the amount of lactate decreases, a ratio of NAD/NADH within a cell increases.

Experimental Example 3-1: Weight Loss Effects in Obese Mice (Ob/Ob) Administered Compounds According to Examples 1 and 2

6.5 week-old C57BL/6J Lep ob/ob mice having genetic obesity characteristics available from ORIENTBIO were prepared. Two mice were raised in each polycarbonate breeding cage (200 W×260 L×130H (mm), Three-shine) in which temperature was 22 to 24° C., relative humidity was 30 to 50%, illuminance was 150 to 300 lux, night and day were 12 hours, and exhaust was performed at 10 to 15 air changes per hour. As a feed, low fat diet (11.9 kcal % fat, 5053, Labdiet) manufactured by ORIENTBIO was used. The feed was contained in a feeder and free intake was allowed. As drinking water, water, which was contained in a 250 mL polycarbonate based bottle, purified through a filter and a sterilizer was used and free intake was allowed.

The Compounds According to Examples 1 and 2 synthesized in the present invention were orally administered to three C57BL/6J Lep ob/ob mice in an amount of 100 mg/kg, respectively, once every day for two weeks. For administration, a disposable syringe fitted with a sonde for oral administration was used and 10 ml/kg of the compound was orally administered into the stomach. As controls, three C57BL/6J Lep ob/ob mice were administered 0.1% SLS in an amount of 100 mg/kg in the same manner as described above. After administration, a time-dependent weight increase ratio was measured and results are illustrated in FIG. 1 below.

Weights of the experimental animals were measured immediately before administration of a test material and six times a week from an administration initiation day to a test termination day. Increased total weights were calculated by subtracting weights measured on an experiment initiation day from weights measured one day before an experiment termination day. Food intake amounts were calculated by measuring feed supply amounts and remaining amounts twice a week from an initiation day of test material administration to a test termination day for each individual.

As shown in graphs of FIG. 1 below, it can be confirmed that weight increase ratios of C57BL/6J Lep ob/ob mice administered the compounds according to Examples 1 and 2 are significantly decreased, when compared with controls.

Experimental Example 3-2: Weight Loss Effects in Obese Mice (Ob/Ob) Administered Compounds According to Examples 4 and 5

Figure 2:
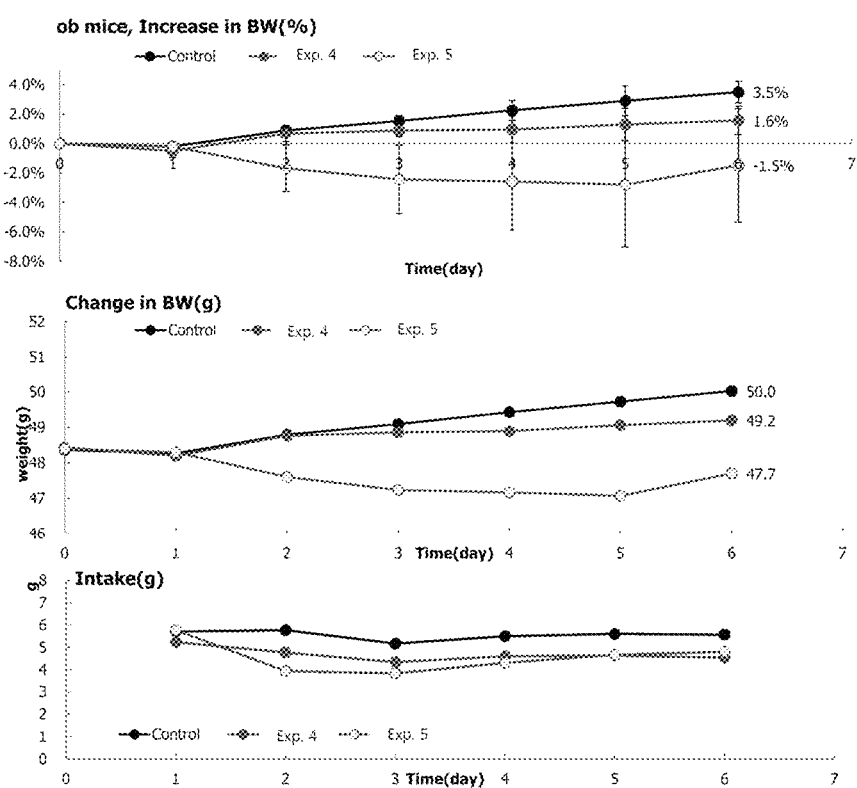
FIG. 2 illustrates graphs representing weight increase ratios, weight change, and intake amounts in obese mice (ob/ob) administered a compound according to Example 4, a compound according to Example 5, and a control administered in Experimental Example 3-2.

Experiments were performed under the same conditions as in Experimental Example 3-1 except that 10.5 week-old C57BL/6J Lep ob/ob mice having genetic obesity characteristics available from ORIENTBIO were prepared, the compounds according to Examples 4 and 5 were administered to three C57BL/6J Lep ob/ob mice in an amount of 150 mg/kg, 150 mg/kg of 0.1% SLS was administered to each of three C57BL/6J Lep ob/ob mice as controls, and experiments were performed for a total of six days. Weight increase ratios, weight change, and intake amounts depending on administration time were measured and results are illustrated in FIG. 2 below.

As illustrated in graphs of FIG. 2 below, it can be confirmed that weight increase ratios, weight change, and intake amounts of C57BL/6J Lep ob/ob mice administered the compounds of Examples 4 and 5 according to the method above are significantly decreased, when compared with controls.

Experimental Example 3-3: Weight Loss Effects in Obese Mice (Ob/Ob) Administered Compounds According to Examples 8 and 28

Figure 3:
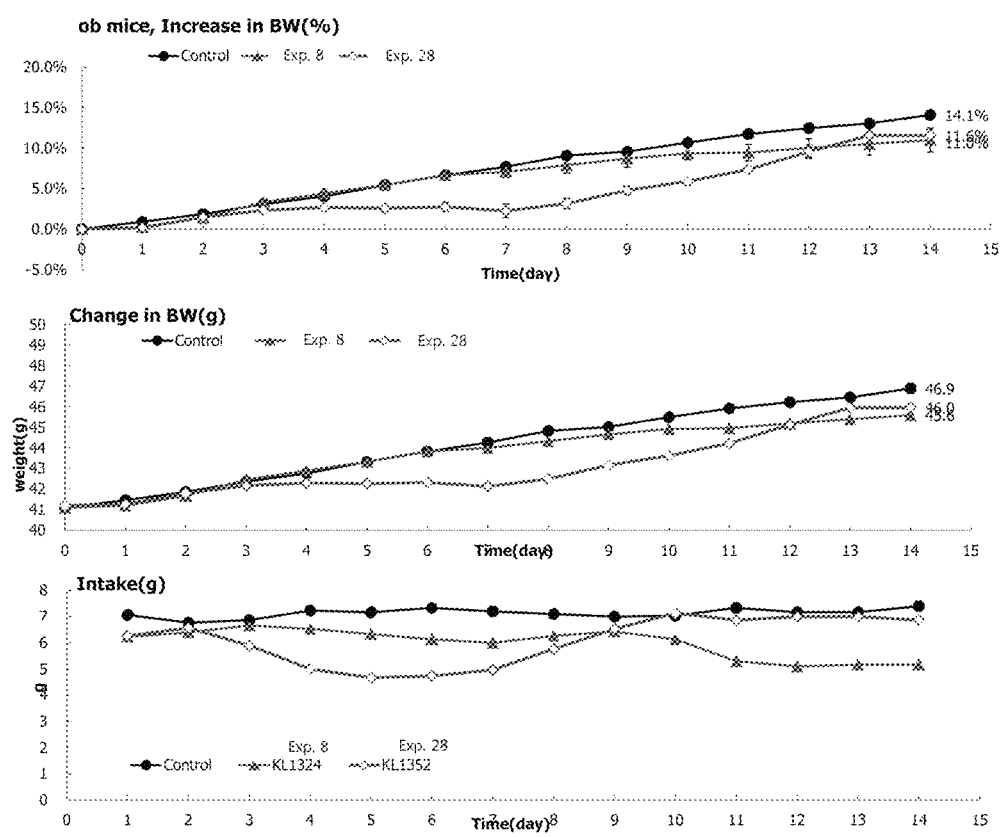
FIG. 3 illustrates graphs representing weight increase ratios, weight change, and intake amounts in obese mice (ob/ob) administered a compound according to Example 8, a compound according to Example 28, and a control in Experimental Example 3-3.

Experiments were performed under the same conditions as in Experimental Example 3-1 except that 6 week-old C57BL/6J Lep ob/ob mice having genetic obesity characteristics available from ORIENTBIO were prepared, each of the compounds according to Examples 8 and 28 was administered to three C57BL/6J Lep ob/ob mice in an amount of 100 mg/kg, and 100 mg/kg of 0.1% SLS was administered to each of three C57BL/6J Lep ob/ob mice as controls. Weight increase ratios, weight change, and intake amounts depending on administration time were measured and results are illustrated in FIG. 3 below.

As illustrated in graphs of FIG. 3 below, it can be confirmed that weight increase ratios and intake amounts of C57BL/6J Lep ob/ob mice administered the compounds of Examples 8 and 28 according to the method above are significantly decreased, when compared with controls.

Experimental Example 3-4: Weight Loss Effects in Obese Mice (Ob/Ob) Administered Compounds According to Examples 9 and 27

Figure 4:
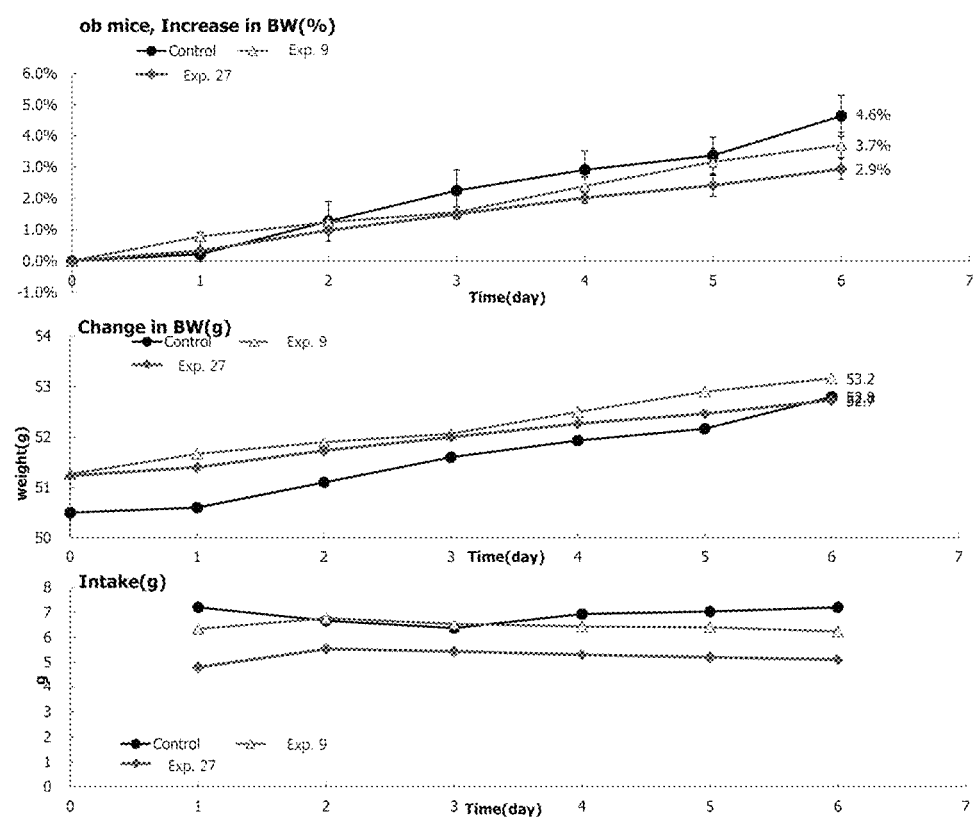
FIG. 4 illustrates graphs representing weight increase ratios, weight change, and intake amounts in obese mice (ob/ob) administered a compound according to Example 9, a compound according to Example 27, and a control administered in Experimental Example 3-4.

Experiments were performed under the same conditions as in Experimental Example 3-1 except that 11 week-old C57BL/6J Lep ob/ob mice having genetic obesity characteristics available from ORIENTBIO were prepared, each of the compounds according to Examples 9 and 27 was administered to three C57BL/6J Lep ob/ob mice in an amount of 100 mg/kg, 100 mg/kg of 0.1% SLS was administered to each of three C57BL/6J Lep ob/ob mice as controls, and experiments were performed for six days. Weight increase ratios, weight change, and intake amounts depending on administration time were measured and results are illustrated in FIG. 4 below.

As illustrated in graphs of FIG. 4 below, it can be confirmed that weight increase ratios and weight change of C57BL/6J Lep ob/ob mice administered the compounds of Examples 9 and 27 according to the method above are significantly decreased, when compared with controls.

Experimental Example 3-5: Weight Loss Effects in Obese Mice (Ob/Ob) Administered Compounds According to Examples 29 and 30

Figure 5:
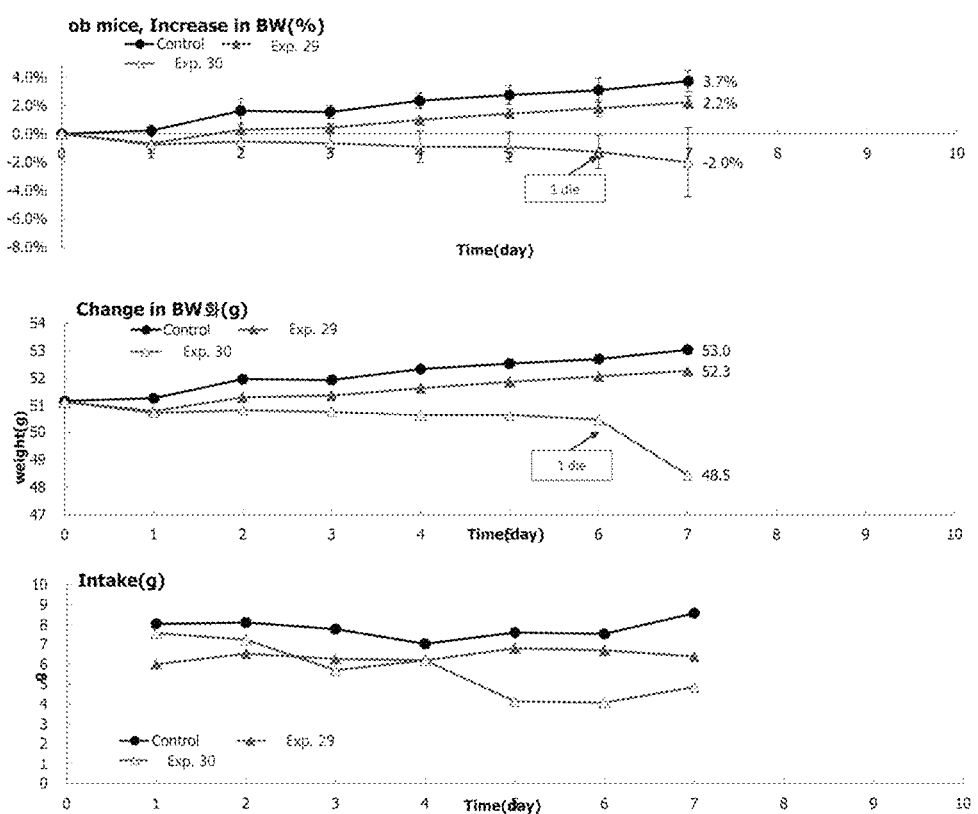
FIG. 5 illustrates graphs representing weight increase ratios, weight change, and intake amounts in obese mice (ob/ob) administered a compound according to Example 29, a compound according to Example 30, and a control administered in Experimental Example 3-5.

Experiments were performed under the same conditions as in Experimental Example 3-1 except that 15 week-old C57BL/6J Lep ob/ob mice having genetic obesity characteristics available from ORIENTBIO were prepared, the compounds according to Examples 29 and 30 were administered to three C57BL/6J Lep ob/ob mice in an amount of 150 mg/kg, 150 mg/kg of 0.1% SLS was administered to each of three C57BL/6J Lep ob/ob mice as controls, and experiments were performed for a total of one week. Weight increase ratios, weight change, and intake amounts depending on administration time were measured and results are illustrated in FIG. 5 below.

As illustrated in graphs of FIG. 5 below, it can be confirmed that weight increase ratios, weight change, and intake amounts of C57BL/6J Lep ob/ob mice administered the compounds of Examples 29 and 30 according to the method above are significantly decreased, when compared with controls.

Experimental Example 3-6: Weight Loss Effects in Obese Mice (Ob/Ob) Administered Compounds According to Examples 35 and 36

Figure 6:
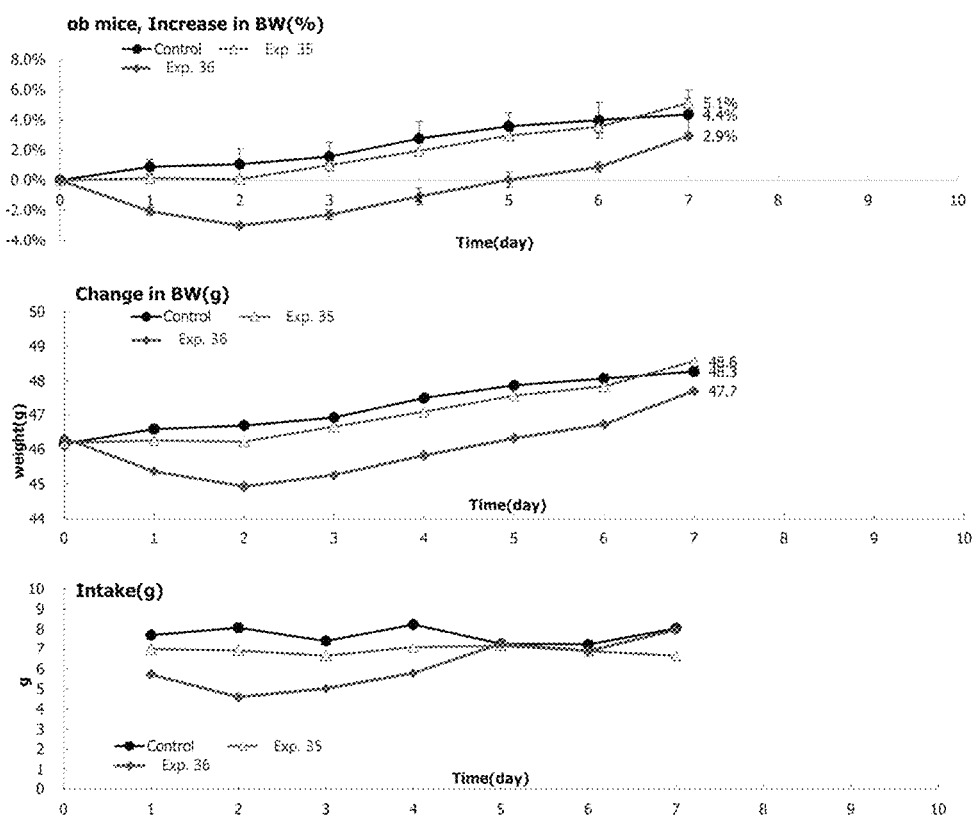
FIG. 6 illustrates graphs representing weight increase ratios, weight change, and intake amounts in obese mice (ob/ob) administered a compound according to Example 35, a compound according to Example 36, and a control administered in Experimental Example 3-6.

Experiments were performed under the same conditions as in Experimental Example 3-1 except that 12 week-old C57BL/6J Lep ob/ob mice having genetic obesity characteristics available from ORIENTBIO were prepared, the compounds according to Examples 35 and 36 were administered to three C57BL/6J Lep ob/ob mice in an amount of 150 mg/kg, 150 mg/kg of 0.1% SLS was administered to each of three C57BL/6J Lep ob/ob mice as controls, and experiments were performed for a total of seven days. Weight increase ratios, weight change, and intake amounts depending on administration time were measured and results are illustrated in FIG. 6 below.

As illustrated in graphs of FIG. 6 below, it can be confirmed that weight increase ratios, weight change, and intake amounts of C57BL/6J Lep ob/ob mice administered the compounds of Examples 35 and 36 according to the method above are significantly decreased, when compared with controls.

Experimental Example 3-7: Weight Loss Effects in Obese Mice (Ob/Ob) Administered Compounds According to Examples 41 and 51

Figure 7:
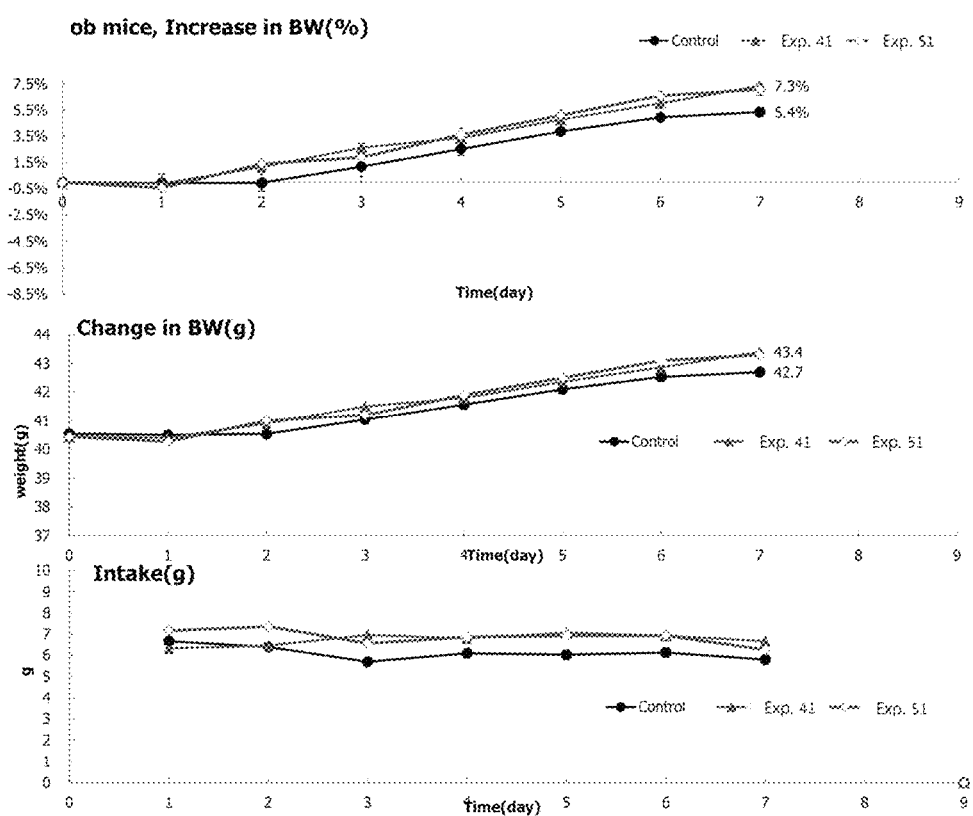
FIG. 7 illustrates graphs representing weight increase ratios, weight change, and intake amounts in obese mice (ob/ob) administered a compound according to Example 41, a compound according to Example 51, and a control administered in Experimental Example 3-7.

Experiments were performed under the same conditions as in Experimental Example 3-1 except that 6.5 week-old C57BL/6J Lep ob/ob mice having genetic obesity characteristics available from ORIENTBIO were prepared, the compounds according to Examples 41 and 51 were administered to three C57BL/6J Lep ob/ob mice in an amount of 150 mg/kg, 150 mg/kg of 0.1% SLS was administered to each of three C57BL/6J Lep ob/ob mice as controls, and experiments were performed for a total of seven days. Weight increase ratios, weight change, and intake amounts depending on administration time were measured and results are illustrated in FIG. 7 below.

As illustrated in graphs of FIG. 7 below, it can be confirmed that weight increase ratios, weight change, and intake amounts of C57BL/6J Lep ob/ob mice administered the compounds of Examples 41 and 51 according to the method above are significantly decreased in some sections, when compared with controls.

Experimental Example 3-8: Weight Loss Effects in Obese Mice (Ob/Ob) Administered Compound According to Example 42

Figure 8:
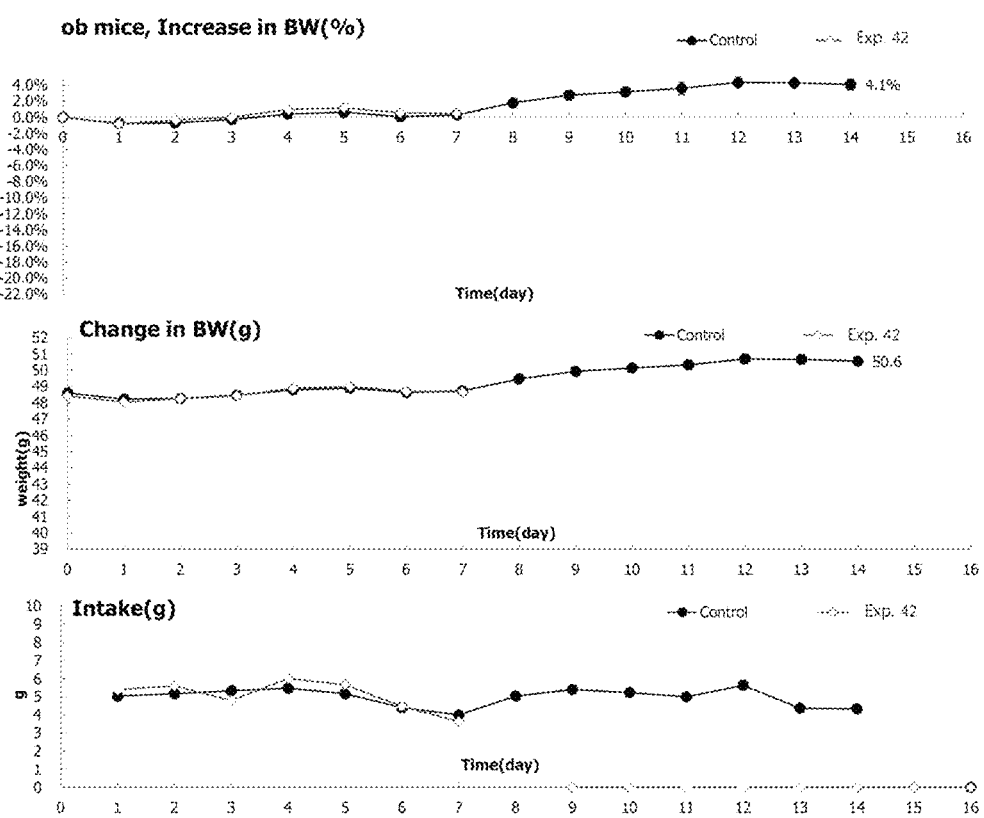
FIG. 8 illustrates graphs representing weight increase ratios, weight change, and intake amounts in obese mice (ob/ob) administered a compound according to Example 42 and a control administered in Experimental Example 3-8.

Experiments were performed under the same conditions as in Experimental Example 3-1 except that 9.5 week-old C57BL/6J Lep ob/ob mice having genetic obesity characteristics available from ORIENTBIO were prepared, the compound according to Example 42 was administered to three C57BL/6J Lep ob/ob mice in an amount of 150 mg/kg and 150 mg/kg of 0.1% SLS was administered to each of three C57BL/6J Lep ob/ob mice as controls. Weight increase ratios, weight change, and intake amounts depending on administration time were measured and results are illustrated in FIG. 8 below.

As illustrated in graphs of FIG. 8 below, it can be confirmed that weight increase ratios, weight change, and intake amounts of C57BL/6J Lep ob/ob mice administered the compound of Example 42 according to the method above are significantly decreased in some sections, when compared with controls.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A compound represented by Formula (1) below or a pharmaceutically acceptable salt, hydrate, solvate, prodrug, tautomer, enantiomer, or pharmaceutically acceptable diastereomer thereof:

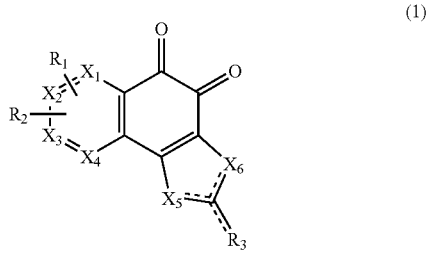

(1)

wherein $R_1$ and $R_2$ are each independently hydrogen, a halogen, hydroxyl, substituted or unsubstituted C1-C20 alkoxy, substituted or unsubstituted C1-C10 alkyl, substituted or unsubstituted C4-C10 aryl, substituted or unsubstituted C4-C10 aryloxy, substituted or unsubstituted C2-C10 heteroaryl, —$NO_2$, —$NR'_1R'_2$, —$NR'_1$ (CO(O)R'$_2$), —$NR'_1$ (C(O)NR'$_1R'_2$), —CO(O)R'$_1$, —C(O)NR'$_1R'_2$, —CN, —SO(O)R'$_1$, —SO(O)NR'$_1R'_2$, —NR'$_1$ (SO(O)R'$_2$), —CSNR'$_1R'_2$, or $R_1$ and $R_2$ form a ring structure of substituted or unsubstituted C4-C10 aryl through coupling or a ring structure of substituted or unsubstituted C2-C10 heteroaryl, where R'$_1$ and R'$_2$ are each independently hydrogen, substituted or unsubstituted C1-C6 alkyl, substituted or unsubstituted C3-C8 cycloalkyl, substituted or unsubstituted C4-C10 aryl, substituted or unsubstituted C4-C10 aryloxy, substituted or unsubstituted C1-C8 heteroaryl, substituted or unsubstituted —(CR"$_1$R"$_2$)m'-C4-C10 aryl, substituted or unsubstituted —(CR"$_1$R"$_2$)m'-C4-C10 heteroaryl or substituted or unsubstituted NR"$_1$R"$_2$; where R"$_1$ and R"$_2$ are each independently hydrogen, or C1-C3 alkyl, or R"$_1$ and R"$_2$ form a ring structure of substituted or unsubstituted C4-C10 aryl through coupling;

$R_3$ is hydrogen, oxygen, a halogen, unsubstituted branched C3-C10 alkyl, substituted or unsubstituted C2-C20 alkene, substituted or unsubstituted C3-C8 cycloalkyl, substituted or unsubstituted C2-C8 heterocycloalkyl, substituted or unsubstituted C4-C10 aryl, substituted or unsubstituted C4-C10 aryloxy, substituted or unsubstituted C1-C10 heteroaryl, substituted or unsubstituted —(CR'$_5$R'$_6$)$_m$—C4-C10 aryl, substituted or unsubstituted —(CR'$_5$R'$_6$)$_m$—C4-C10 aryloxy, substituted or unsubstituted —(CR'$_5$R'$_6$)$_m$—C1-C10 heteroaryl, substituted or unsubstituted —(CR'$_5$R'$_6$)$_m$—NR'$_3$R'$_4$, substituted or unsubstituted —(CR'$_5$R'$_6$)$_m$—C2-C10 heterocycloalkyl, substituted or unsubstituted —(CR'$_5$R'$_6$)$_m$—OR'$_3$, substituted or unsubstituted —(CR'$_5$R'$_6$)$_m$(O)COR'$_3$, —CO(O)R'$_3$, —CONR'$_3$R'$_4$, —NR'$_3$R'$_4$, —NR'$_3$(C(O)R'$_4$);

where R'$_3$ and R'$_4$ are each independently hydrogen, substituted or unsubstituted C1-C6 alkyl or unsubstituted C3-C8 cycloalkyl, substituted or unsubstituted C4-C10 aryl, substituted or unsubstituted —(CR'$_5$R'$_6$)$_m$—C4-C10 aryl, substituted or unsubstituted —(CR'$_5$R'$_6$)$_m$—C4-C10 aryloxy, substituted or unsubstituted —(CR'$_5$R'$_6$)$_m$—C1-C10 heteroaryl, —CO(O)R'''$_3$, or R'$_3$ and R'$_4$ form a ring structure of substituted or unsubstituted C2-C10 heterocycloalkyl or substituted or unsubstituted C1-C10 heteroaryl through coupling;

R'$_5$ and R'$_6$ are each independently hydrogen or C1-C3 alkyl; and R'''$_3$ is C1-C6 alkyl;

wherein a substituted group is at least one selected from the group consisting of hydroxy, a nitro group, a halogen, C1-C10 alkyl, C2-C10 alkenyl, C2-C10 alkynyl, C1-C10 alkoxy, C1-C10 alkoxycarbonyl, C3-C8 cycloalkyl, C2-C8 heterocycloalkyl, C4-C10 aryl, and C2-C10 heteroaryl;

$X_1$, $X_2$, $X_3$ and $X_4$ are each independently C(H), CO, or N (R"$_3$);

$X_6$ is O when $X_5$ is N (R"$_4$) and $X_6$ is N (R"$_4$) when $X_5$ is O;

where R"$_3$ and R"$_4$ are each independently hydrogen, substituted or unsubstituted C1-C6 alkyl, C1-C6 alkoxy, or substituted or unsubstituted —(CH$_2$)$_n$—C4-C6 aryl, and the substituted group is at least one selected from the group consisting of hydroxy, a halogen, and C1-C5 alkyl;

m, m', and n are each independently a natural number of 1 to 4;

a heteroatom is at least one selected from N, O, and S; and
" ~~~ " means a single bond or a double bond.

2. The compound or the pharmaceutically acceptable salt, hydrate, solvate, prodrug, tautomer, enantiomer, or pharmaceutically acceptable diastereomer thereof according to claim 1, wherein $X_1$, and $X_2$ are each independently C(H), CO, or N(R$_3$"), where R$_3$" is hydrogen or C1-C3 alkyl; and $X_3$ and $X_4$ are each independently C(H) or N.

3. The compound or the pharmaceutically acceptable salt, hydrate, solvate, prodrug, tautomer, enantiomer, or pharmaceutically acceptable diastereomer thereof according to claim 2, wherein $X_1$ is C(H), N, NH, or NCH$_3$;

$X_2$ is C(H) or CO; and $X_3$ and $X_4$ are each independently C(H) or N.

4. The compound or the pharmaceutically acceptable salt, hydrate, solvate, prodrug, tautomer, enantiomer, or pharmaceutically acceptable diastereomer thereof according to claim 1, wherein $R_1$ and $R_2$ are each independently hydrogen, F, Cl, —OCH$_3$, —OCH$_2$CH$_3$, —O(CH$_2$)$_2$CH$_3$, —CH$_3$, —NO$_2$, —NH$_2$, —N(CH$_3$)$_2$, —NHCOCH$_3$, —NHCOC$_3$H$_5$, —NHCOC$_3$H$_7$, or —CN or —OH.

5. The compound or the pharmaceutically acceptable salt, hydrate, solvate, prodrug, tautomer, enantiomer, or pharmaceutically acceptable diastereomer thereof according to claim 1, wherein $R_3$ is hydrogen, isopropyl, isobutyl, t-butyl, neopentyl, substituted or unsubstituted C4-C8 aryl, substituted or unsubstituted C4-C8 aryloxy, substituted or unsubstituted C1-C8 heteroaryl, substituted or unsubstituted —(CR'$_5$R'$_6$)$_m$—OR'$_3$, substituted or unsubstituted —(CR'$_5$R'$_6$)$_m$—OCOR'$_3$, or substituted or unsubstituted —(CR'$_5$R'$_6$)$_m$—NR'$_3$R'$_4$; where R'$_3$ and R'$_4$ are each independently hydrogen, substituted or unsubstituted C1-C5 alkyl, or substituted or unsubstituted C4-C10 aryl, or R'$_3$ and R'$_4$ forms a ring structure of substituted or unsubstituted C4-C10 heterocycloalkyl or substituted or unsubstituted C1-C6 heteroaryl through coupling;

R'$_5$ and R'$_6$ are each independently hydrogen or C1-C3 alkyl;

a substituted group is at least one selected from the group consisting of hydroxy, a halogen, C1-C10 alkyl, C2-C10 alkenyl, C2-C10 alkynyl, C1-C10 alkoxy, C1-C10 alkoxycarbonyl, C3-C8 cycloalkyl, C2-C8 heterocycloalkyl, C4-C10 aryl, and C5-C10 heteroaryl;

a heteroatom is at least one selected from N, O, and S; and m is a natural number of 1 to 4.

6. The compound or the pharmaceutically acceptable salt, hydrate, solvate, prodrug, tautomer, enantiomer, or pharmaceutically acceptable diastereomer thereof according to claim 5, wherein $R_3$ is isopropyl, isobutyl, t-butyl, neopentyl, substituted or unsubstituted phenyl, substituted or unsubstituted —$(CR'_5R'_6)_m$—$OR'_3$, or substituted or unsubstituted —$(CHR'_5)_m$—$NF_3F_4$, where $R'_3$ and $R'_4$ are each independently hydrogen, methyl, ethyl, propyl, or substituted or unsubstituted C4-C10 aryl, or $R'_3$ and $R'_4$ form a ring structure of substituted or unsubstituted C4-C6 heterocycloalkyl through coupling;

$R'_5$ is hydrogen or methyl;

a substituted group is at least one selected from the group consisting of a halogen, C1-C3 alkyl, and C1-C3 alkoxy;

a heteroatom is at least one selected from N, O, and S; and m is a natural number of 1 to 2.

7. The compound or the pharmaceutically acceptable salt, hydrate, solvate, prodrug, tautomer, enantiomer, or pharmaceutically acceptable diastereomer thereof according to claim 5, wherein $R_3$ is isopropyl, t-butyl, phenyl, phenyl substituted with fluorine, —$CH_2OCOCH_3$—$CH_2N(CH_3)_2$, substituted or unsubstituted —$CH_2NCH_3C_6H_5$, substituted or unsubstituted —$CH_2NHC_6H_5$

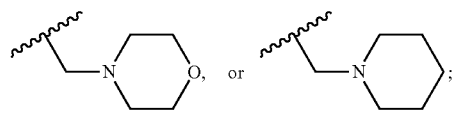 [SMILES: *CN1CCOCC1 ; *CN1CCCCC1]

and the substituted group is at least one selected from the group consisting of a halogen, methyl and methoxy.

8. The compound or the pharmaceutically acceptable salt, hydrate, solvate, prodrug, tautomer, enantiomer, or pharmaceutically acceptable diastereomer thereof according to claim 1, wherein $R''_4$ is hydrogen, C1-C3 alkyl, substituted or unsubstituted —$CH_2$—C4-C6 aryl, wherein a substituted group is a halogen.

9. The compound or the pharmaceutically acceptable salt, hydrate, solvate, prodrug, tautomer, enantiomer, or pharmaceutically acceptable diastereomer thereof according to claim 1, wherein the compound of Formula (1) is one of compounds below:

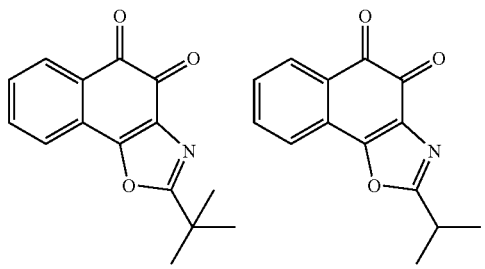

-continued

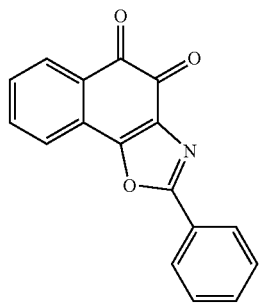

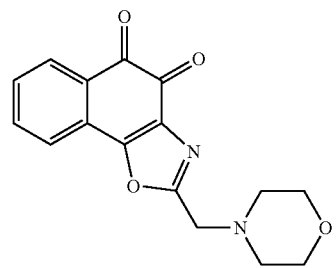

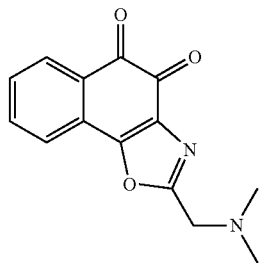

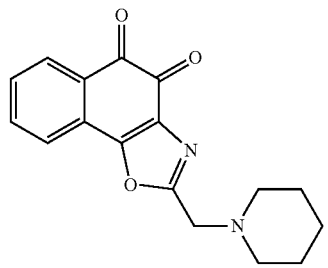

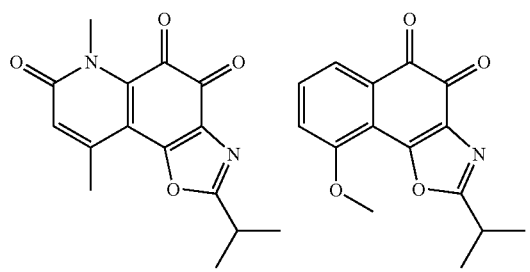

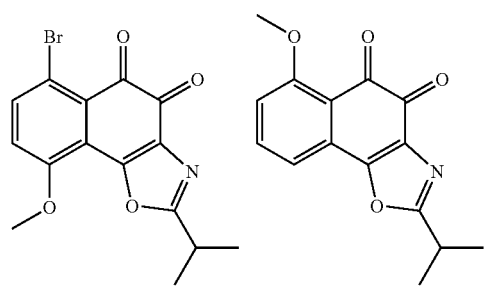

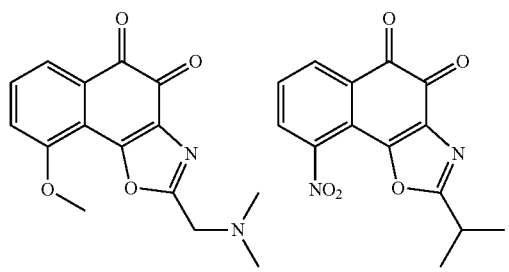
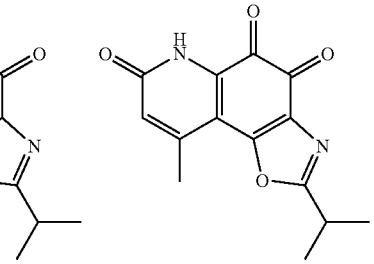
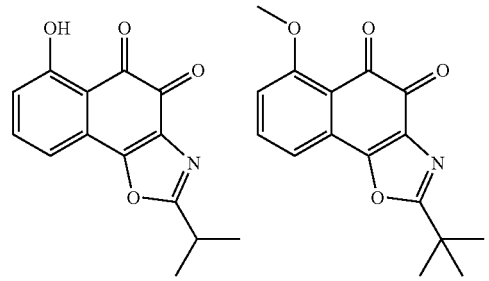
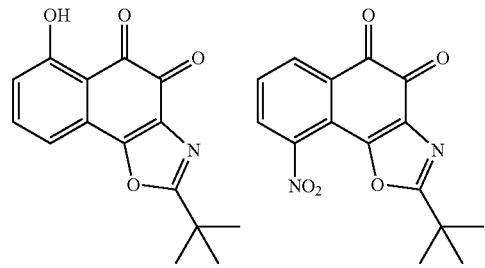
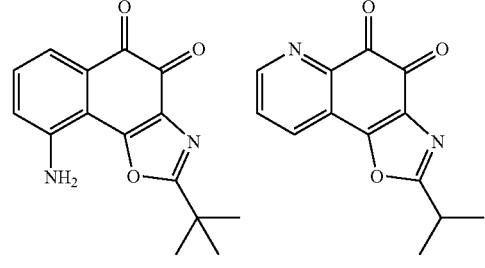
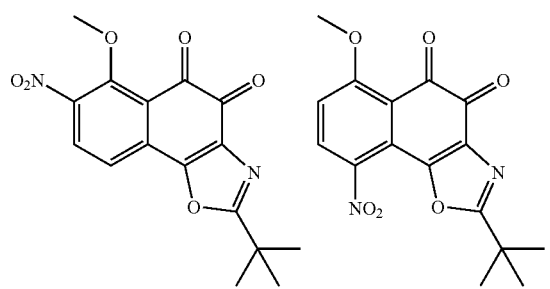
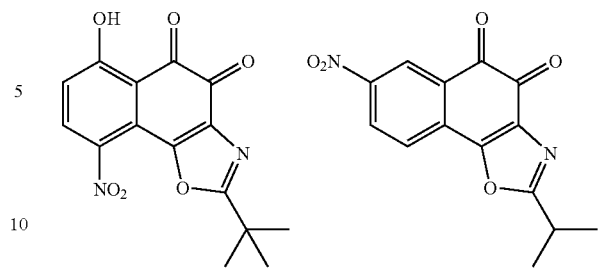
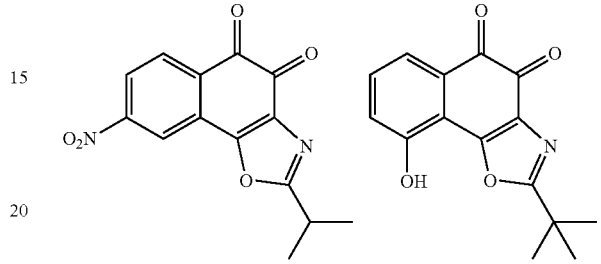
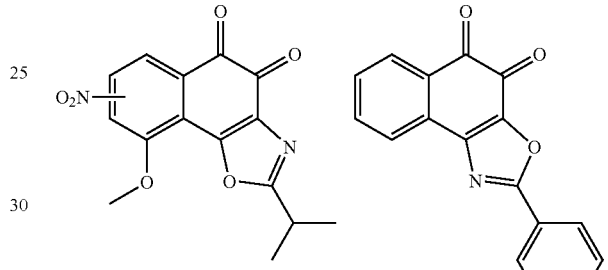
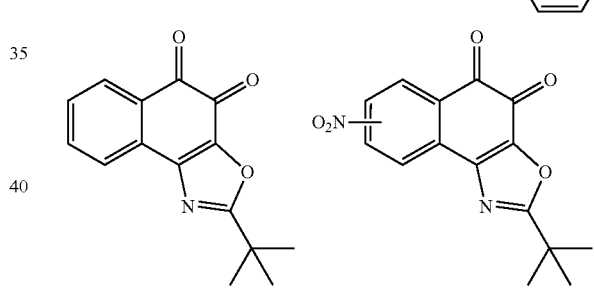
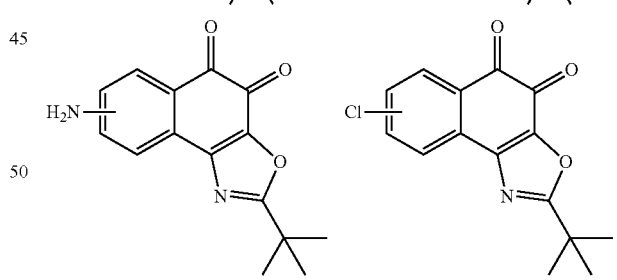
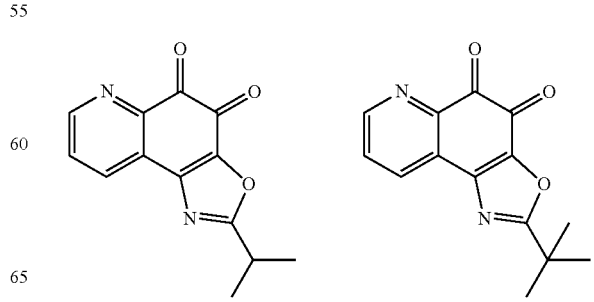

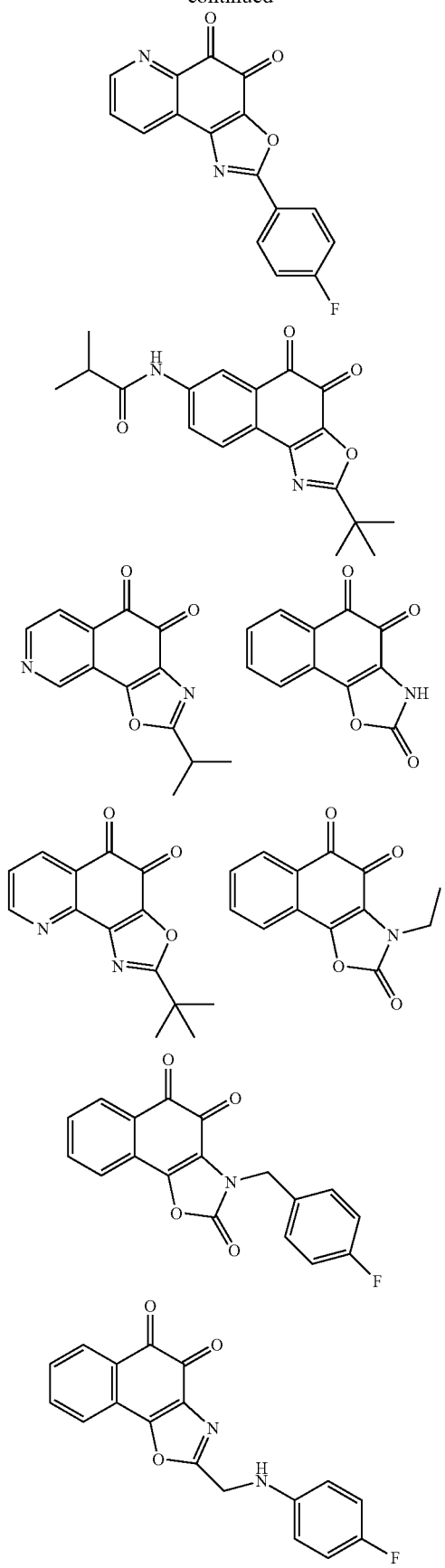
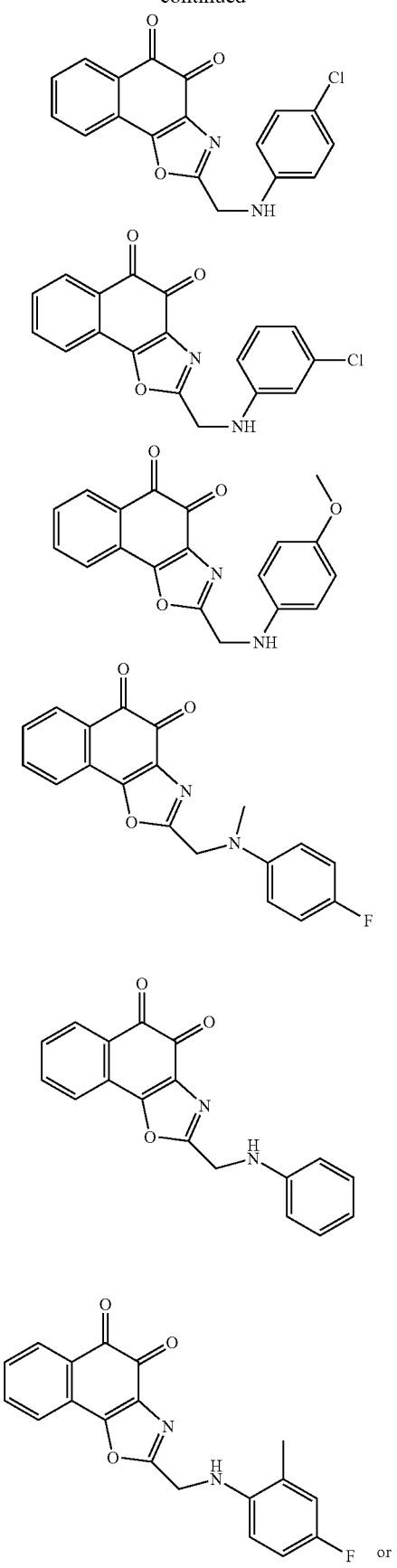

-continued

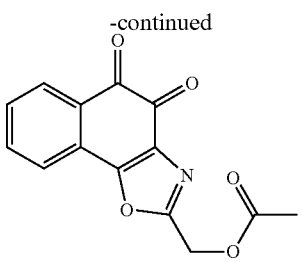

10. A method of preparing the compound of Formula (1) according to claim 1, the method comprising:
A) introducing —$NH_2$ to a compound of Formula (2) below;
B) reacting the compound generated in the introducing (A) with $R_3COH$, $R_3X$ or 4-nitrophenyl chloroformate under acidic conditions or reacting with $R_3COH$ or $R_3X$ under acidic conditions after reacting MX; and
C) oxidizing the compound generated in the reacting (B) or oxidizing the compound generated in the reacting (B) after reacting under acidic conditions:

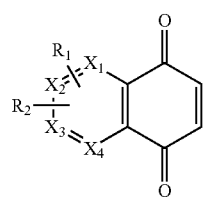

(2)

wherein $X_1$ to $X_4$ and $R_1$ to $R_3$ are the same as defined in Formula (1), M is Cu, Al, or B, and X is a halogen.

11. The method according to claim 10, wherein, in the introducing (A), the compound of Formula (2) and O-benzylhydroxylamine hydrochloride or $NaN_3$ are reacted to introduce —$NH_2$.

12. The method according to claim 10, further comprising reacting the compound generated in the oxidizing (C) and MX' or R"$_4$X',
wherein M is Cu, Al, or B; X' is a halogen; and R"$_4$ is the same as defined in Formula (1).

13. The method according to claim 10, further comprising (D) reacting the compound generated in the oxidizing (C) with $HNO_3$ to introduce —$NO_2$.

14. A method of preparing the compound of Formula (1) according to claim 1, the method comprising:
a) introducing —$NH_2$ to the compound of Formula (2);
b) reacting the compound generated in the introducing (a) with $(R_8O)_2CH(CH_2)_nX$ under acidic conditions; and
c) oxidizing the compound generated in the reacting (b) and then reacting with $R_9R_{10}NH$ or $R'_3COOK$, or reacting the compound generated in the reacting (b) with $R_9R_{10}NH$ and then oxidizing,
wherein $R_8$ is C1-C3 alkyl;
$R_9$ and $R_{10}$ are each independently hydrogen, C1-C3 alkyl, substituted or unsubstituted phenyl, or $R_9$ and $R_{10}$ forms a ring structure of C4-C6 heterocycloalkyl through coupling, wherein a heteroatom is at least one selected from the group consisting of N, O, and S and a substituted group is at least one selected from a halogen, C1-C3 alkyl and C1-C3 alkoxy;

$R'_3$ is the same as defined Formula (1);
X is a halogen; and
n' is an integer of 0 to 4.

15. A method of preparing the compound of Formula (1) according to claim 1, the method further comprising:
A') introducing —$NO_2$ to the compound of Formula (4) below through $HNO_3$ reaction;
B') reducing the compound generated in the introducing (A') or reducing after reacting with $R_6X''$; and
C') reacting the compound generated in the reducing (B') and the compound generated in the introducing (A) with $R_3COH$ under acidic conditions and then oxidizing,

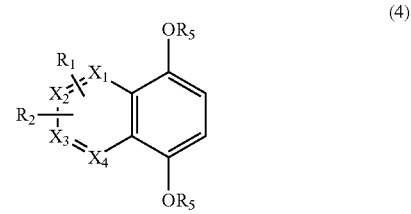

(4)

wherein $X_1$ to $X_4$ and $R_1$ to $R_3$ are the same as defined in Formula (1); $R_5$ and $R_6$ each are C1-C5 alkyl; and X" is a halogen.

16. A method of preparing the compound of Formula (1) according to claim 1, the method comprising:
1) reacting the compound of Formula (5) below with $R_7NH_2$; and
2) oxidizing the compound generated in the reacting (1),

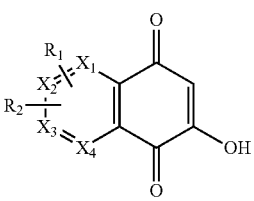

(5)

wherein $X_1$ to $X_4$ and $R_1$ to $R_3$ are the same as defined in Formula (1); and $R_7$ is C1-C5 alkyl or benzyl.

17. The method according to claim 16, further comprising (3) introducing $NO_2$ to the compound generated in the oxidizing (2).

18. The method according to claim 17, further comprising (4) hydrogenating the compound generated in the introducing (3).

19. The method according to claim 18, further comprising (5) reacting the compound generated in the hydrogenating (4) with CuX''', where X''' is a halogen or CN.

20. The method according to claim 18, further comprising (4-1) reacting the compound generated in the hydrogenating (4) with $R_3COCl$, where $R_3$ is the same as defined in claim 1.

21. A method of preparing the compound of Formula (1) according to claim 1, the method comprising:
(1') alkylating the compound of Formula (6) below, and then reducing $NO_2$ to $NH_2$ through reduction and introducing a halogenation group; and
(2') reacting the compound generated in the alkylating (1') with $R_3COCl$;

(3') cyclizing the compound generated in reacting (2') and then hydrogenating; and
(4') oxidizing the compound generated in the cyclizing (3'),

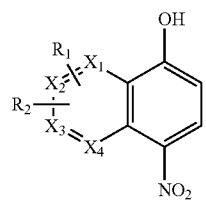

(6)

wherein $X_1$ to $X_4$ and $R_1$ to $R_3$ are the same as defined in Formula (1).

22. The method according to claim 21, further comprising (2'-1) reacting the compound generated in the reacting (2') with a metal halide and alkylating between the reacting (2') and cyclizing (3').

23. A pharmaceutical composition comprising (a) a therapeutically effective amount of the compound of Formula (1) according to claim 1 and/or a pharmaceutically acceptable salt, hydrate, solvate, tautomer, enantiomer, and/or pharmaceutically acceptable diastereomer thereof; and (b) a pharmaceutically acceptable carrier, diluent, or vehicle, or a combination thereof.

24. A method of treating metabolic syndromes using a therapeutically effective amount of the compound of Formula (1) according to claim 1 or a pharmaceutically acceptable salt, hydrate, solvate, tautomer, enantiomer, or pharmaceutically acceptable diastereomer thereof.

* * * * *